(12) United States Patent
Rovani, Jr. et al.

(10) Patent No.: US 10,662,384 B2
(45) Date of Patent: May 26, 2020

(54) METHODS FOR ANALYZING HYDROCARBONS AND HYDROCARBON BLENDS FOR CHEMICAL COMPOSITIONS

(71) Applicant: The University of Wyoming Research Corporation, Laramie, WY (US)

(72) Inventors: Joseph F. Rovani, Jr., Laramie, WY (US); Jeramie Joseph Adams, Laramie, WY (US); Ryan Bradley Boysen, Laramie, WY (US); Jean-Pascal Planche, Laramie, WY (US); Nicholas David Bolton, Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 52 days.

(21) Appl. No.: 16/183,649

(22) Filed: Nov. 7, 2018

(65) Prior Publication Data

US 2019/0106639 A1 Apr. 11, 2019

Related U.S. Application Data

(63) Continuation-in-part of application No. 15/167,766, filed on May 27, 2016, now Pat. No. 10,221,363,
(Continued)

(51) Int. Cl.
| | | |
|---|---|---|
| *C10G 53/08* | (2006.01) | |
| *C10G 25/00* | (2006.01) | |
| *G01N 33/28* | (2006.01) | |
| *G01N 30/46* | (2006.01) | |
| *B01J 20/281* | (2006.01) | |
| *B01J 20/283* | (2006.01) | |
| *B01J 20/284* | (2006.01) | |
| *G01N 30/14* | (2006.01) | |
| *B01D 15/00* | (2006.01) | |
| *C10G 25/12* | (2006.01) | |
| *B01J 20/287* | (2006.01) | |
| *B01J 20/286* | (2006.01) | |
| *B01D 15/26* | (2006.01) | |

(Continued)

(52) U.S. Cl.
CPC ........... *C10G 25/003* (2013.01); *B01D 15/00* (2013.01); *B01D 15/265* (2013.01); *B01J 20/281* (2013.01); *B01J 20/283* (2013.01); *B01J 20/284* (2013.01); *B01J 20/286* (2013.01); *B01J 20/287* (2013.01); *C10G 25/12* (2013.01); *C10G 53/08* (2013.01); *G01N 30/14* (2013.01); *G01N 30/461* (2013.01); *G01N 30/468* (2013.01); *G01N 33/2823* (2013.01); *C10G 2400/30* (2013.01); *G01N 33/2835* (2013.01); *G01N 2030/027* (2013.01); *G01N 2030/085* (2013.01); *G01N 2030/143* (2013.01); *G01N 2030/8854* (2013.01)

(58) Field of Classification Search
CPC ...... C10G 25/004; C10G 25/12; C10G 53/08; G01N 30/461; G01N 30/468; G01N 33/28; G01N 33/2823; G01N 2030/027
See application file for complete search history.

(56) References Cited

U.S. PATENT DOCUMENTS

| 4,493,765 A | 1/1985 | Long et al. |
| 4,628,204 A | 12/1986 | Maes |

(Continued)

FOREIGN PATENT DOCUMENTS

| EP | 400989 A | 5/1990 |
| WO | 0077120 A2 | 12/2000 |

(Continued)

OTHER PUBLICATIONS

Parallel U.S. Appl. No. 13/243,782, Office action dated Jun. 27, 2012. 9 pages.
Parallel U.S. Appl. No. 13/243,782, Notice of Allowance dated Aug. 3, 2012. 9 pages.
Ovalles, C. et al. Predicting Reactivity of Feedstocks to Hydroprocessing by Using Asphaltene Characterization Techniques. Prepr. Pap.-Am. Chem. Soc., Div. Energy Fuels Chem. 2012, 57(2), 763. 3 pages.
Rogel, E. et al. Sediment Formation in Residue Hydroconversion Processes and Its Correlation to Asphaltene Behavior. Prepr. Pap.-Am. Chem. Soc., Div. Energy Fuels Chem. 2012, 57(2), 745.

(Continued)

*Primary Examiner* — Renee Robinson
(74) *Attorney, Agent, or Firm* — Santangelo Law Offices, P.C.

(57) ABSTRACT

The present invention is generally related to the analysis of chemical compositions of hydrocarbons and hydrocarbon blends. This method applies specifically to the problem of analyzing extremely complex hydrocarbon-containing mixtures when the number and diversity of molecules makes it impossible to realistically identify and quantify them individually in a reasonable timeframe and cost. The advantage to this method over prior art is the ability to separate and identify chemical constituents and solvent fractions based on their solvent-solubility characteristics, their high performance liquid chromatographic (HPLC) adsorption and desorption behaviors, and their interactions with stationary phases; and subsequently identify and quantify them at least partially using various combinations of non-destructive HPLC, destructive HPLC, and stand-alone detectors presently not routinely used for HPLC but reconfigured to obtain spectra on the fly. This analytical method is especially useful for, but not limited to, asphalt binders and asphalt binder blends, modified asphalts, asphalt modifiers, asphalt additives, polymer-modified asphalts, asphalts containing rejuvenators and softening agents, asphalts containing recycled products, aged asphalts, and air-blown asphalts, which may contain wide varieties of different types of additives and chemistries, and forensic applications, and environmental pollutant identification.

55 Claims, 33 Drawing Sheets

Related U.S. Application Data which is a continuation of application No. 13/237,568, filed on Sep. 20, 2011, now Pat. No. 9,353,317.

(60) Provisional application No. 62/582,808, filed on Nov. 7, 2017.

(51) Int. Cl.
  *G01N 30/08* (2006.01)
  *G01N 30/88* (2006.01)
  *G01N 30/02* (2006.01)

(56) References Cited

U.S. PATENT DOCUMENTS

| | | |
|---|---|---|
| 4,634,680 A | 1/1987 | Kingsley |
| 4,865,741 A | 9/1989 | Nolte |
| 4,988,446 A | 1/1991 | Haberman |
| 4,990,773 A | 2/1991 | Supernaw et al. |
| 5,092,983 A | 3/1992 | Eppig et al. |
| 5,266,800 A | 11/1993 | Mullins |
| 5,381,002 A | 1/1995 | Morrow et al. |
| 5,424,959 A | 6/1995 | Reyes et al. |
| 5,574,215 A | 11/1996 | Bunger et al. |
| 5,861,228 A | 1/1999 | Descales et al. |
| 5,969,237 A | 10/1999 | Jones et al. |
| 6,773,921 B1 | 8/2004 | Schabron et al. |
| 7,875,464 B2 | 1/2011 | Schabron et al. |
| 8,241,920 B2 | 8/2012 | Schabron et al. |
| 8,273,581 B2 | 9/2012 | Schabron et al. |
| 8,367,425 B1 | 2/2013 | Schabron et al. |
| 8,492,154 B1 | 7/2013 | Schabron et al. |
| 8,530,240 B1 | 9/2013 | Schabron et al. |
| 8,628,970 B1 | 1/2014 | Schabron et al. |
| 9,353,317 B2 | 5/2016 | Schabron et al. |
| 2003/0211621 A1 | 11/2003 | Rovani et al. |
| 2007/0048874 A1 | 3/2007 | Schabron et al. |
| 2011/0062058 A1 | 3/2011 | Rogel et al. |
| 2011/0066441 A1 | 3/2011 | Ovalles et al. |
| 2011/0120950 A1 | 5/2011 | Schabron et al. |
| 2012/0016168 A1 | 1/2012 | Schabron et al. |
| 2012/0160015 A1 | 6/2012 | Ovalles et al. |

FOREIGN PATENT DOCUMENTS

| | | |
|---|---|---|
| WO | 0077120 A3 | 12/2000 |
| WO | 02063292 A1 | 8/2002 |
| WO | 03096011 A1 | 11/2003 |
| WO | 2011032123 A2 | 3/2011 |
| WO | 2011032125 A2 | 3/2011 |
| WO | 2011038125 A2 | 3/2011 |
| WO | 2011113017 A2 | 9/2011 |
| WO | 2011/127044 | 2/2012 |
| WO | WO2011/127044 | 2/2012 |

OTHER PUBLICATIONS

Schabron, J.F. Use of the Asphaltene Determinator ™ Method to Monitor Vacuum Residue Stability to Improve Refinery Distillation Efficiency, 2011.
Parallel U.S. Appl. No. 13/490,307; Office action dated Oct. 4, 2012. 10 pages.
McLean J. B. et al. Reactivity Screening of Feedstocks for Catgalytic Coal/Oil Co-Processing, Sep. 1986, http://web.anl.gov/PCS/acsfuel/preprint%20archive/Files/31_4_ANAHEIM_09-86_0169.pdf. 12 pages.
Mariaca-DomAnguez et al. "Reactivity of Fluid Catalytic Cracking Feedstocks as a Function of Reactive Hydrogen Content", Petroleum Science and Technology, 2004, vol. 22, Issue 1-2, pp. 13-29.
Johnson and Moyse, "Pretreatment of resid FCC feedstocks", Jul. 2004, http://www.digitalrefining.com/article/1000161.
Parallel U.S. Appl. No. 12/970,535, Notice of Allowance dated Jun. 8, 2012. 8 pages.
Baker, C. A. et al. A new chromatographic procedure and its application to high polymers, J. Chem. Soc., 1956, 2352-2362.
Parallel U.S. Appl. No. 13/600,039; Office action dated Nov. 19, 2012. 24 pages.
Parallel U.S. Appl. No. 13/490,316; Notice of Allowance dated Dec. 10, 2012.
Barman, B.N.; Crude Oil: Liquid Chromatography; 2000; Academic Press. 47 pages.
"Energy and Environmental Profile of the US Petroleum Refining Industry," 1988, Prepared by Energetics Inc. for U.S. Department of Energy Office of Industrial Technologies. 124 pages.
"Standard Test Method for Molecular Weight (Relative Molecular Mass) of Hydrocarbons by Thermoelectric Measurement of Vapor Pressure," ASTM Designation: D 2503-82 (Reapproved 1997), 871-873.
Andersen, S.I. et al., 1991, "Aggregation of Asphaltenes as Determined by Calorimetry," Journal of Colloid and Interface Science, 142, 497-502, 1991.
Barton, A.F., 1974, "Solubility Parameters," Chemical Reviews, 75 (6), 731-753.
Bodusynski, M.M. et al., 1982, Separation of Solvent-Refined Coal into Solvent-Derived Fractions, Analytical Chemistry, 54, 372-375.
Burrell, H., 1955, Solubility Parameters. Interchemical Review, 3-16, 32-46.
Carrier, H. et al; Acoustic method for measuring asphaltene flocculation in crude oil, Journal of Petroleum Science and Engineering, pp. 111-117.
Cartz, L., ch. 3, Ultrasonic Testing, Nondestructive Testing, 1995, pp. 81-98.
Del Bianco, A. et al., 1993, Thermal Cracking of Petroleum Residues 1. Kinetic Analysis of the Reaction. Fuel, 72 (1). 81-85.
Heithaus, J.J., 1962, Measurement and Significance of Asphaltene Peptization، Journal of the Institute of Petroleum 48 (458), 45-53.
Hildebrand, J.H. et al., 1970, Regular and Related Solutions؇ Van Nostrand Reinhold, NY, pp. 24-27, pp. 152-153, pp. 212-215.
Jones et al. Development of an ultrasonic oil stability monitor for the assessment of asphaltene aggregation in hydrocarbon streams, Proceed. Intern. Conf. Mitigat. Heat Exch. Foul. Econ. Envir. Implic. Banff, AB, Canada, Jul. 1999, 84-94.
Long, R.B. et al., 1989, Studies in Petroleum Composition؇ Revue de Institute Francais du Petrole, abstract.
Long, R.B., 1979, Chemistry of Asphaltenes. Preprints, Div. Petroleum Chemistry, American Chemical Society, 24, 891-901.
Magaril, R.Z. et al., 1968, Study of the Mechanism of Coke Formation in the Cracking of Petroleum Resins, International Chemical Engineering 8 (4), 727.
McClements, D.J., Ultrasonic Measurements in Particle Size Analysis, University of Massachusetts, Amherst, USA, Encyclopedia of Analytical Chemistry (Applications, Theory and Instrumentation) pp. 1-8.
Pal R. et al., 1989, Viscosity/Concentration Relationships for Emulsions. Journal of Rheology, 33 (7), 1021-1045.
Pauli, A.T. 1996, Asphalt Compatibility Testing Using the Automated Heithaus Titration Test؇ Preprints, Division of Fuel Chemistry, American Chemical Society, 41 (4), 1276-1281.
Pauli, A.T. et al., 1998, Relationships Between Asphaltenes, Heithaus Compatibility Parameters, and Asphalt Viscosity. Petrol. Science and Technology, 16 (9&10), 1125-1147.
Pauli, A.T. et al., Stability and Compatibility Testing of Petroleum and Asphalt ؇ American Laboratory, Sep. 2003, 2 pages.
Phillips, C.R, et al. 1985, Kinetic Models for the Thermal Cracking of Athabaska Bitumen, Fuel 64(5), 678-691.
Scatchard, G. 1931, Equilibria in Non-Electrolyte Solutions in Relation to the Vapor Pressure and Densities of the Components؇ Chemical Reviews, 321-333.
Schabron, J.F. et al. Coking indexes using the Heithaus titration and asphaltene solubilitl, Preprints American Chemical Society, Division of Petroleum Chemistry (1999), 44(2), 187-189.
Schabron, J.F. et al., 1998, The Solubility and Three-Dimensional Structure of Asphaltenes. Petroleum Science and Technology, 16 (3-4), 361-376.

(56) References Cited

OTHER PUBLICATIONS

Schabron, J.F. et al., 1999 Petroleum Residua Solubility Polarity Map: Stability Studies of Residua Pyrolysis☀ Department of Energy Report under contract # DE-FC26-98FT40322 Task, 1.2, 24 pages.
Schabron, J.F. et al., 2000 Deposition from Heavy Oils. Department of Energy Report under contract # DE-FC26-98F140322, 35 pages.
Schabron, J.F. et al., 2001b, Molecular Weight Polarity Map for Residua Pyrolysis, Fuel, 80 (4), 529-537.
Schabron, J.F. et al., 2001c, Non-Pyrolytic Heat Induced Deposition from Heavy Oils, Fuel, 80 (7) 919-928.
Schabron, J.F., et al., 2002b, Residua Coke Formation Predictability Maps, Fuel, 81 (17) 2227-2240.
Schabron, J.F. et al., 2001a, Predicting Coke Formation Tendencies, Fuel, 80 (10) 1435-1446.
Schabron, J.F. et al., 2002, Characterization of Residua During Pyrolysis, Preprints, Div. of Petroleum Chemistry, American Chemical Society, 47 (1), 17-21.
Schabron, J.F. et al., 1993, The Characterization of Petroleum Residua. U.S. Dept of Energy Report under contract # DE-FC21-86MC110761, 68 pages.
Schabron, J.F. et al., 2002, Thermal Analysis for Monitoring Incipient Coke Formatio■, US Department of Energy Report DE/FG36/01G011018, 18 pages.
Schabron, J.F. et al , 2002, Coke Formation Process Model for Petroleum Refining Efficiency Improvemen▼, US Department of Energy Report under contract # DE/FG36/01G011018, 40 pages.
Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322. 46 pages.
Singh, I.D., V. Kothiyal, V. Ramaswamy, and R. Krishna, 1990, Characteristic Changes of Asphaltenes During Visbreaking of North Gujarat Short Residue. Fuel, 69 (3), 289-292.
Small, P.A., 1953, Some Factors Affecting the Solubility of Polymers☀ Journal of Applied Chemistry, 71-80.
Snyder, L.R., 1968, Principles of Adsorption Chromatography. Marcel Dekker, Inc., New York, 206-210.
U.S. Appl. No. 60/711,599, filed Aug. 25, 2005.
Wiehe, I.A., 1993, A Phase-Separation Kinetic Model for Coke Formation, Ind. Eng. Chem. Res., 32 (11), 244× 2454.
Wiehe, I.A., 1996, Two-Dimensional Solubility Parameter Mapping of Heavy Oils☀ Fuel Science and Technology International, 14 (1&2), 289-312.
Bodusynski, M.S. et al., 1987, "Composition of heavy petroleums: 1. molecular weight, hydrogen deficiency, and heteroatom concentration as a function of atmospheric equivalent boiling point up to 1400 degrees F" Energy & Fuels, 1, 2-11.
Schabron, J.F., et al., 2006, "Initial studies using ultrasonic spectroscopy for monitoring changes in residua with pyrolysis," Fuel 85, 2093-2105.
Chiantore, Oscar and Simonelli, Alessandra, "Precipitation-redissolution Liquid Chromatography of Styrene-ethyl Acrylate Copolymers," Polymer Engineering and Science, Aug. 1999, vol. 39 No. 8, p. 1383-1388.
Cortell, Jessica M. et al., "Infulence of Vine Vigor on Grape (*Vitis vinifera* L. Cv. Pino Noir) Anthrocyanins. 2. Anthocyanins and Pigmented Polymers in Wine," J. Agric. Food Chem. 2007, 55, p. 6585-6595.
Aske, Narve et al.; "Determination of Saturate, Aromatic, Resin, and Asphaltenic (SARA) Components in Crude Oils by Means of Infrared and Near-Infrared Spectroscopy," Energy & Fuels, 2001, 15, 1304-1312.
Corbett, L.W., "Composition of Asphalt Based on Generic Fractionation, Using Solvent Deasphaltening, Elution-Adsorption Chromatography, and Densimetric Characterization," Analytical Chemistry, p. 576-579.
McCarthy, James E. et al.; "EPA's Regulation of Coal-Fired Power: Is a "Train Wreck" Coming?", Congressional Research Service, CRS Report for Congress, Aug. 8, 2011, 7-5700, R41914. 50 pages.

"Standard Test Method for n-Heptane Insulbles1", Designation: D 3279-97 (Reapproved 2001).
Parallel U.S. Appl. No. 13/243,782, Office action dated Jun. 27, 2012.
Parallel U.S. Appl. No. 13/243,782, Notice of Allowance dated Aug. 3, 2012.
Ovalles, C. et al. Predicting Reactivity of Feedstocks to Hydroprocessing by Using Asphaltene Characterization Techniques. Prepr. Pap.-Am. Chem. Soc., Div. Energy Fuels Chem. 2012, 57(2), 763.
Parallel U.S. Appl. No. 13/490,307; Office action dated Oct. 4, 2012.
McLean J. B. et al. Reactivity Screening of Feedstocks for Catgalytic Coal/Oil Co-Processing, Sep. 1986, http://web.anl.gov/PCS/acsfuel/preprint%20archive/Files/31_4_ANAHEIM_09-86_0169.pdf.
Parallel U.S. Appl. No. 12/970,535, Notice of Allowance dated Jun. 8, 2012.
Parallel U.S. Appl. No. 13/600,039; Office action dated Nov. 19, 2012.
Barman, B.N.; Crude Oil: Liquid Chromatography; 2000; Academic Press.
"Energy and Environmental Profile of the US Petroleum Refining Industry," 1988, Prepared by Energetics Inc. for U.S. Department of Energy Office of Industrial Technologies, pp. 4-5, 27, 33, 49 and 62-63.
Burrell, H., 1955, Solubility Parameters╲ Interchemical Review, 3-16.
Cartz, L., ch. 3, Ultrasonic Testin✱, Nondestructive Testing, 1995, pp. 81-98.
Del Bianco, A. et al., 1993, Thermal Cracking of Petroleum Residues 1. Kinetic Analysis of the Reaction. Fuel, 72 (1), 7× 80.
Heithaus, J.J., 1962, Measurement and Significance of Asphaltene Peptization Journal of the Institute of Petroleum 48 (458), 45-53.
Hildebrand, J.H. et al., 1970, Regular and Related Solutions☀ Van Nostrand Reinhold, NY, pp. 24-27, pp. 152-153, pp. 212-215.
Jones et al. Development of an ultrasonic oil stability monitor for the assessment of asphaltene aggregation in hydrocarbon stream▲, Proceed. Intern. Conf. Mitigat. Heat Exch. Foul. Econ. Envir. Implic. Banff, AB, Canada, Jul. 1999, 84-94.
Long, R.B. et al., 1989, Studies in Petroleum Composition☀ Revue de ● Institute Francais du Petrole, abstract.
Long, R.B., 1979, The Concept of Asphaltenes Preprints, Div. Petroleum Chemistry, American Chemical Society, 24, 891-901.
McClements, D.J., Ultrasonic Measurements in Particle Size Analysi▲, University of Massachusetts, Amherst, USA, Encyclopedia of Analytical Chemistry (Applications, Theory and Instrumentation) pp. 5581-5587.
Pauli, A.T. 1996, Asphalt Compatibility Testing Using the Automated Heithaus Titration Test☀ Preprints, Division of Fuel Chemistry, American Chemical Society, 41 (4), 1276-1281.
Pauli, A.T. et al., Stability and Compatibility Testing of Petroleum and Asphalt☀ American Laboratory, Sep. 2003, 2 pages.
Scatchard, G. 1931, Equilibria in Non-Electrolyte Solutions in Relation to the Vapor Pressure and Densities of the Components ☀ Chemical Reviews, 321-333.
Schabron, J.F. et al., 1998, The Solubility and Three-Dimensional Structure of Asphaltenes☀ Petroleum Science and Technology, 16 (3-4), 361-376.
Schabron, J.F. et al., 1999 Petroleum Residua Solubility Parameter/Polarity Map: Stability Studies of Residua Pyrolysis☀ Department of Energy Report under contract # DE-FC26-98FT40322 Task, 1.2, 24 pages.
Schabron, J.F. et al., 2000 Deposition from Heavy Oils☀ Department of Energy Report under contract # DE-FC26-98FT40322, 35 pages.
Schabron, J.F. et al., 2002a, Characterization of Residua During Pyrolysis, Preprints, Div. of Petroleum Chemistry, American Chemical Society, 47 (1), 17-21.
Schabron, J.F. et al., 1993, The Characterization of Petroleum Residua ☀ U.S. Dept of Energy Report under contract # DE-FC21-86MC110761, 68 pages.

(56) References Cited

OTHER PUBLICATIONS

Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322.

Singh, I.D., V. Kothiyal, V. Ramaswamy, and R. Krishna, 1990, Characteristic Changes of Asphaltenes During Visbreaking of North Gujarat Short Residue. Fuel, 69 (3), 28 ♣ 292.

Small, P.A., 1953, Some Factors Affecting the Solubility of Polymers ⅋ Journal of Applied Chemistry, 71-80.

Snyder, L.R., 1968, Principles of Adsorption Chromatography ⅋ Marcel Dekker, Inc., New York, 206-210.

U.S. Appl. No. 60/711,599, filed Aug. 25, 2005, entitled Rapid Determination of Asphaltenes and the Cyclohexane Soluble Portion of Asphaltenes by Automated On-Column Precipitation and Re-Dissolution; Specification 24 pages, Drawings 8 pages.

Wiehe, I.A., 1996, Two-Dimensional Solubility Parameter Mapping of Heavy Oils Fuel Science and Technology International, 14 (1&2), 289-312.

Boduszynski, M.S. et al., 1987, Composition of heavy petroleums: 1. molecular weight, hydrogen deficiency, and heteroatom concentration as a function of atmospheric equivalent boiling point up to 1400 degrees F' Energy & Fuels, 1, 2-11.

Corbett, L.W., "Composition of Asphalt Based on Generic Fractionation, Using Solvent Deasphaltening, Elution-Adsorption Chromatography, and Densimetric Characterization," Analytical Chemistry, p. 576.

McCarthy, James E. et al.; "Ea's Regulation of Coal-Fired Power: Is a "Train Wreck" Coming?", Congressional Research Service, CRS Report for Congress, Aug. 8, 2011, 7-5700, R41914.

E. Rogel et al., "Asphaltene Stability in Crude Oil and Petroleum Materials by Solubility Profile Analysis," Energy and Fuel, 24 (8), pp. 4369-4374 (2010) (Published on Web Jul. 28, 2010).

F.P. Burke et al., "Liquid Column Fractionation: A Method of Solvent Fractionation of Coal Liquefication and Petroleum Products," Fuel, vol. 58, pp. 539-541 (1979).

F.K. Schweighart et al., "Development of SRC-I Product Analysis. vol. 2. Evaluation of Analytical Techniques for SRC-I Characterization, Recycle Solvent Studies, and Product Fractionation Studies," published Sep. 1, 1983.

M.M. Boduszynski, "Composition of Heavy Petroleums. 1. Molecular Weight, Hydrogen Deficiency, and Heteroatom Concentration as a Function of Atmospheric Equivalent Boiling Point up to 1400 F (760 C)," Energy & Fuels, vol. 1, No. 1, pp. 2-11 (1987).

M.M. Boduszynski et al, "Separation of Solvent0Refined Coal into Solvent-Derived Fractions," Analyical Chemistry, vol. 54, pp. 372-375 (1982).

Ovalles, C. et al. Characterization of Heavy Crude Oils, Their Fractions, and Hydrovisbroken Products by the Asphaltene Solubility Fraction Method, dx.doi.org/10.1021/ef201499f | Energy Fuels 2012, 26, 549-556, Published: Dec. 7, 2011.

Lopez-Linares, F. et al. Adsorption of Athabasca Vacuum Residues and Their Visbroken Products over Macroporous Solids: Influence of Their Molecular Characteristics, dx.doi.org/10.1021/ef201047z | Energy Fuels 2011, 25, 4049-4054, Published Aug. 17, 2011.

Rogel, E., Asphaltene Chemical Characterization as a Function of Solubility: Effects on Stability and Aggregation, dx.doi.org/10.1021/ef2013979 | Energy Fuels, Published Nov. 7, 2011.

Schabron, J. F. et al. The Waxphaltene Determinator Method for Automated Precipitation and Re-Dissolution of Wax and Asphaltene Components, Energy Fuels, Article ASAP, DOI: 10.1021/ef300184s, Feb. 27, 2012.

Parallel U.S. Appl. No. 12/970,535, Office action dated Mar. 2, 2011.

Parallel U.S. Appl. No. 12/970,535, Office action dated Oct. 7, 2011.

Parallel U.S. Appl. No. 12/970,535, Office action dated Jan. 12, 2012.

Parallel U.S. Appl. No. 13/243,782, Office action dated Mar. 23, 2012.

Schabron, J. F. et al., Asphaltene Determinator Method for Automated On-Column Precipitation and Redissolution of Pericondensed Aromatic Asphaltene Components. Energy Fuels 2010, 24, 5984-5996.

Standard Test Method for Separation of Asphalt into Four Fractions. Designation: D4124-09. 383-390.

U.S. Appl. No. 13/237,568, filed Sep. 20, 2011. First Named Inventor: John F. Schabron.

"Standard Test Method for Separation of Asphalt into Four Fractions1," ASTM International, Designation D4124-09.

"Energy and Environmental Profile of the US Petroleum Refining Industry," 1988, Prepared by Energetics Inc. for U.S. Department of Energy Office of Industrial Technologies.

Schabron, J.F., et al., "Asphaltene Determinator Method for Automated On-Column Precipitation and Redissolution of Pericondensed Aromatic Asphaltene Components," Energy Fuels 2010, 24, 5984-5996, DOI: 10.102/ef100822f.

Fan, T. et al., "Rapid and Accurate SARA Analysis of Medium Gravity Crude Oils," Energy & Fuels 2002, 16, 1571-1575.

Schabron, J.F., et al., "On-column precipitation and re-dissolution of asphaltenes in petroleum residua," Fuel 87 (2008) 165-176.

Grizzle, Patrick L, et al., "Automated Liquid Chromatographic Compound Class Grou-Type Separation of Crude Oils and Bitumens Using Chemically Bonded Aminosilane," Anal. Chem. 1986, 58, 2389-2396.

Jewell, D.M. et al., "Ion-Exchange, Coordination, and Adsorption Chromatographic Separation of Heavy-End Petroleum Distillates," Laramie Energy Research Center, Analytical Chemistry, vol. 44, No. 8, Jul. 1972, p. 1391.

Jiang, C et al., "TLC-FID (Iatroscan) analysis of heavy oil and tar sand samples," Organic Geochemistry 39 (2008) 1210-1214.

Karlsen, D.A. et al., "Analysis of petroleum fractions by TLC-FID: applications to petroleum reservoir description," Org. Geochem. vol. 17, No. 5, pp. 603-617, 1991.

Kharrat, D.A. et al., "Issues with Comparing SARA Methodologies," Energy & Fuels 2007, 21, 3618-3621.

Masson, J-F et al., "Dynamics of Bitumen Fractions by Thin-Layer Chromatography/Flame Ionization Detection," Energy & Fuels 2001, 15, 955-960.

Radke, M et al., "Preparative Hydrocarbon Group Type Determination by Automated Medium Pressure Liquid Chromatography," Anal. Chem. 1980, 52, 406-411.

Schabron, J.F. et al.; "Petroleum Processing Efficiency Improvement," Topical Report, May 2011.

Wiehe, Irwin A. et al.; "The Oil Compatibility Model and Crude Oil Incompatibility," Energy & Fuels 2000, 14, 56-59.

Fan, Z et al.; "Challenges in Processing Bitumens and Heavy Oils," Prepr. Pap.-Am. Chem. Soc., Div. Petr. Chem. 2009, 54 (1), 4.

"Canada regulator approves Enbridge diluent Line," Reuters, Business & Financial News, Feb. 19, 2008, Calgary, Alberta.

"Opportunity Crudes Report II: Technologies and Strategies for Meeting Evolving Market and Environmental Challenges," Hydrocarbon Publishing Company, an updated and expanded study of the 2006 report titled "Opportunity Crudes: Technical Challenges and Economic Benefits.".

USPTO Office Action for U.S. Appl. No. 11/510,491 dated Dec. 9, 2010.

USPTO Office Action for U.S. Appl. No. 11/510,491 dated Sep. 3, 2010.

USPTO Office Action for U.S. Appl. No. 11/510,491 dated Jul. 13, 2009.

USPTO Office Action for U.S. Appl. No. 11/510,491 dated Mar. 30, 2010.

USPTO Office Action for U.S. Appl. No. 11/510,491 dated Mar. 2, 2011.

http://www.specialchem4adhesives.com/resources, Determining Critical Surface Tension of Solid Substrates, printed Sep. 13, 2011, 3 pages.

Energy Information Administration/Capacity Report 2001.

Robinson, P. R., Petroleum Processing Overview, Practical Advances in Petroleum Processing 2006:1-78.

(56) References Cited

OTHER PUBLICATIONS

Rogel, E. et al. Asphaltene Stability in Processed Samples using Solubility Profile Analysis, Prepr. Pap.-Am. Chem. Soc. Div. Pet. Chem. 2011, 56(1), 3.

Ovalles, C. et al. Characterization and Preparative Separation of Heavy Crude Oils, their fractions and thermally Cracked Products by the Asphaltene solubility Frations Method, Prepr.-Am. Chem Soc. Div. Pet. Chem. 2011, 56(1), 8.

Schabron J. F. et al., Total Pericondensed Aromatic (TPA) Determination as an Alternative to Gravimetric Asphaltenes, Prepr. Pap.-Am. Chem. Soc. Div. Pet. Chem. 20011, 56(1), 38.

Rogel, E. et al. Determination of Asphaltenes in Crude Oil and Petroleum Products by the on Column Precipitation Method, Energy Fuels 2009, 23, 4515-4521.

Al-Muhareb et al., Characterization of Petroleum Asphaltenes by Size Exclusion Chromatography, UV-fluorescence and Mass Spectrometry, Petroleum Science and Technology, London, UK, 2007.

Steffens et al., Application of Fluorescence to the Study of Crude Petroleum, Springer Science+Business Media, LLC, Brazil, Dec. 14, 2009.

Cho et al., Application of Saturates, Aromatics, Resins, and Asphaltenes Crude Oil Fractionation for Detailed Chemical Characterization of Heavy Crude Oils by Fourier Transform Ion Cyclotron Resonance Mass Spectrometry Equipped with Atmospheric Pressure Photoionization, ACS Publications, Korea, 2012.

Abou-Hatab, Substituent Effects on the Absorption and Fluorescence Properties of Anthracene, The Journal of Physical Chemistry, Philadelphia, Pennsylvania, Princeton, New Jersey, Jan. 19, 2017.

Yarranton et al., Regular Solution Based Approach to Modeling Asphaltene Precipitation from Native and Reacted Oils: Part 2, Molecular Weight, Density, and Solubility Paremeter of Saturates, Aromatics, and Resins, Elsevier Ltd., Canada, Netherlads, Nov. 19, 2017.

Hussein, Characterization of Petroleum Crude Oils using Laser Induced Fluorescence, Journal of Petroleum & Environmental Biotechnology, Cairo, Egypt, 2015.

Sylvia et al., Durability Study: Field Aging of conventional and Polymer Modified Binders, TRB 2010 Annual Meeting CD-ROM, France, Switzerland, Jul. 31, 2009.

McKay et al., Flourescence Spectroscopy in the Characterization of High-Boiling Petroleum Distillates, Laramie Energy Research Center, Bureau of Mines, U.S. Dept. of the Interior, Laramie, Wyoming.

McCann et al., Instrumental Method Suitable for the Detection of Polymers in Asphalt Binders, Transportation Research Board, Atlanta, Georgia, Laramie, Wyoming, Jul. 20, 2007.

Karpicz et al., Laser Flourosensor for Oil Spot Detection, Institute of Physics, Vilnius, Lithuania.

Ryder, Analysis of Crude Petroleum Oils Using Flourescence Spectroscopy, Department of Chemistry, and National Centre for Biomedical Engineering Science, National University of Ireland—Galway, Galway, Ireland.

Related U.S. Appl. No. 11/510,491, Notice of Allowance dated Nov. 17, 2010.

Related U.S. Appl. No. 13/490,316; Office action dated Aug. 3, 2012.

Agilent Technologies 1260 Infinity Variable Wavelength Detector Manual G1314-90013, Rev. C, Nov. 2013.

Agilent Technologies 1260 Infinity Diode Array and Multiple Wavelength Detector Manual G1315-90015 Rev. C, Jul. 2018.

Wavelength Standards for the Near-Infrared Spectral Region, Apr. 1, 2007, Spectroscopy, vol. 23, Issue 4.

The U.S.'s Most Commonly Recycled Material? Asphalt Pavements http://www.asphaltpavement.org/index.php?option=com_content &view=article&id=1146:the-u-s-s-most-commonly-recycled-material-asphalt-pavements&Itemid=767.

Effects of aging on the properties of asphalt, P.E.YuhongWang,, KechengZhao, CharlesGlover.

LingChen,YongWen, DanChong, ChichunHu, Construction and Building Materials, vol. 80, Apr. 2015.

Influence of six rejuvenators on the performance properties of Reclaimed Asphalt Pavement (RAP) binder and 100% recycled asphalt mixtures, Martins Zaumanis, Rajib Mallick,Lily Poulikakis, Rober Frank, Construction and Building Materials, vol. 71, Nov. 2014.

SHRP-A-645, SHRP Materials Reference Library: Asphalt Cements: A Concise Data Compilation David R. Jones, IV, Asphalt Research Program, The University of Texas at Austin.

The Use of Spectrophotometry UV-Vis for the Study of Porphyrins, Rita Giovannetti, University of Camerino, Chemistry Section of School of Environmental Sciences, Camerino, Italy.

Abou-Hatab, S., V. A. Spata, and S. Matsika. 2017. "Subsituent Effects on the Absorption and Fluorescnce Properties of Antrhacene." Journal of Phyical Chemistry A 1213-1222.

Al-hajji, A., and O. R. Koseoglu. 2016. Characterization of Crude Oil and Its Fractions by Fluorescence Spectroscopy Analysis. International Patent 2016/111956.

Al-Muhareb, E., T. J. Morgan, A. A. Herod, and R. Kandiyoti. 2007. "Characterization of Petroleum Asphaltenes by Size Exlusion Chromotography, UV-fluorescence and Mass Spectrometry." Petroleum Science and Technolgy 81-91.

Groenzin, H., O. C. Mullins, S. Eser, J. Mathews, M.-G. Yang, and D. Jones. 2003. "Molecular Size of Asphaltene Solubility Fracitons." Energy Fuels 498-503.

Karpicz, R., A. Dementjev, Z. Kuprionis, S. Pakalnis, R. Westphal, R. Reuter, and V. Gulbinas. 2005. "Laser Fluorosensor for Oil Spot Detection." Lithuanian Journal of Physics 213-218.

M. Zander, M. W. Haenel. 1990. "Regularities in the Fluoescence Spectra of Coal-tar Pitch Fractions." Fuel 1206-1207.

Mullins, O. C. 1999. "Optical Interrogation of Aromatic Moieties in Crude Oils and Asphaltenes." In Structures and Dynamics of Asphaltenes, by E. Y. Sheu O. C. Mullins, 21-77. New York: Plenum Press.

Scott R., and L. Montanari. 1998. "Molecular Structure and Intermolecular Interaction of Asphaltenes by FT-IR, NMR, EPR." In Structure and Dynamics of Asphaltenes, by O. C. Mullins and Eric Y. Sheu, 93-95. New York: Plenum Press.

Petersen J.C., Quantitative Functional Group Analysis of Asphalts Using Differential Infrared Spectrometry and Selective Chemical Reactions—Theory and Application, Transportation Research Record, 1986;1096:1.

J. Lamontagne, P. Dumas, V. Mouillet, J. Kister, Comparison by Fourier transform infrared (FTIR) spectroscopy of different ageing techniques: application to road bitumens, Fuel 80 (2001) 483-488.

V. Mouillet, J. Lamontagne, F. Durrieu, J-P. Planche, L. Lapalu, "Infrared microscopy investigation of oxidation and phase evolution in bitumen modified with polymers", Fuel 87 (2008) 1270-1280.

Recycling of polyethylene terephthalate (PET) plastic bottle wastes in bituminous asphaltic concrete Adebayo Olatunbosun Sojobi1*, Stephen Emeka Nwobodo1 and Oluwasegun James Aladegboye1, Cogent Engineering (2016), 3: 1133480.

Brûlé B, Migliori F., 1983, Application de la chromatographie sur gel perméable à la caractérisation de bitumes routiers et de leur susceptibilité au vieillissement artificiel. Bulletin de Liaison Laboratoire des Ponts Chaussées; 128:107-20.

Haley, G. A., 1975, Changes in chemical composition of Kuwait short residue during air blowing. Analytical Chemistry, 47 (14): 2432-2437.

Spectra Analysis, Fully-Automated HPLC-FTIR Detection System, https://www.laboratoryequipment.com/news/2010/10/fully-automated-hplc-flir-detection-system, Oct. 19, 2010.

Wilt et al., Determination of Asphaltenes in Petroleum Crude Oils by Fourier Transform Infrared Spectroscopy, Marathon-Ashland Petroleum L.L.C., Kentucky.

Aske et al., Determination of Saturate, Aromatic, Resin, and Asphaltenic (SARA) Components in Crude Oils by Means of Infrared and Near-Infrared Spectroscopy, The Norwegian University of Science and Technology, Trondheim, Norway Jun. 29, 2001.

Melendez et al., Prediction of the Sara analysis of Colombian crude oils using ATR-FTIR spectroscopy and chemometric methods, Elsevier B.V., Columbia, 2012.

(56) References Cited

OTHER PUBLICATIONS

Andersen, Separation of Asphalteness by Polarity Using Liquid-Liquid Extraction, Petroleum Science and Technology, Lyngby, Denmark, 1997.
Riveros et al., Determination of Asphaltene and Resin Content in Venezuelan Crude Oils by Using Fluorescence Spectroscopy and Partial Least Squares Regression, Energy & Fuels, Venezuela, 2006.
Ai-Muhareb et al., Characterization of Petroleum Asphaltenes by Size Exclusion Chromatography, UV-fluorescence and Mass Spectrometry, Petroleum Science and Technology, London, UK, 2007.
Lehrer et al., Gel Permeation Chromatography of Asphalts and Asphaltenes, Die Makromolekulare Chemie, 1965.
Leontaritis et al., Fast Crude-Oil Heavy-Component Characterization Using Combination of ASTM, HPLC, and GPC Methods, Journal of Petroleum Science and Engineering, Netherlands, 1989.
Acevedo et al., Molecular weight properties of asphaltenes calculated from GPC data for octylated asphaltenes, Elsevier Science, LTD, Great Britian, 1998.
Trejo et al., Characterization of Asphaltenes from Hydrotreated Products by SEC, LDMS, MALDI, NMR, and XRD, American Chemical Society, May 31, 2007.
Dong et al., Size-Exclusion Chromatography of Asphaltenes: An Experimental Comparison of Commonly Used Approaches, Springer-Verlag, 2013.
Akmaz et al., The Structural Characterization of Saturate, Aromatic, Resin, and Asphaltene Fractions of Batiraman Crude Oil, Petroleum Science and Technology, Jan. 2011.
Leon et al., Determination of Molecular Weight of Vacuum Residue and their Sara Fractions, Ciencia, Tecnología y Futuro, Columbia, 2010.
Andersen, Concentration Effects in HPLC-SEC Analysis of Petroleum Asphaltenes Journal of Liquid Chromatography & Related Technologies, Denmark, Sep. 23, 2006.
Andersen et al., Asphaltene Precipitation and incipient Flocculation in Mixed Solvents, Danish Natural Science Research Council, Denmark.
Acevedo et al., Asphaltenes and resins from the basin, INTEVEP, S.A., Venezuela, Nov. 7, 1984.
Andersen, et al., Asphaltene Precipitation and Incipient Flocculation in Mixed Solvents, Danish Natural Science Research Council and Western Research Institute, Copenhage, Denmark, Laramie, WY.
Andersen, Concentration Effects in HPLC-SEC Analysis of Petroleum Asphaltenes, Journal of Liquid Chromatography & Related Technologies, Lyngby, Denmark, Sep. 23, 2006.
Acevedo et al., Asphaltenes and resins from the basin, Universidad Central de Venezuela, Facultad de Ciencias, Venezuela, Nov. 7, 1984.
Carr et al., Glossary of HPLC/LC Separation Terms, LCGC North America, North America, Feb. 1, 2008.
Altgelt et al., GPC Separation and Integrated Structural Analysis of Petroleum Heavy Ends, Separation Science, Richmond, CA, 1970.
Bishara, A New Approach for the Determination of MSD of Asphalt Cement Using HPGPC, Fuel Science & Technology International, Topeka, KS, 1992.
Branthaver, Binder Characterization and Evaluation vol. 2: Chemistry, Strategic Highway Research Program, National Research Council, Washington, DC, Nov. 1993.
Brule et al., Relationships Between Composition, Structure, and Properties of Road Asphalts: State of Research at the French Public Works Central Laboratory, Transportation Research Record.
Carbognani, Fast Monitoring of C20-C160 Crude Oil Alkanes by Size-Exclusion Chromatography-Evaporative Light Scattering Detection Performed with Silica Columns, Journal of Chromatography, Venezuela, 1997.
Dreessen et al., Durability Study: Field Aging of Conventional and Polymer Modified Binders, Total RM, Laboratory of traffic facilities, Switzerland, France, Jul. 31, 2009.
Haley, Changes in Chemical Composition of a Kuwait Short Residue during Air Blowing, School of Highway Engineering, University of New South Wales, Kensington, Australia, Dec. 1975.
Jennings et al., HP-GPC Analysis of Asphalt Fractions in the Study of Molecular Self-Assembly in Asphalt, Department of Chemistry and Biochemistry, Gaines Hall, Montana State University, Bozeman, MT.
Kim, et al., Use of GPC Chromatograms to Characterize Aged Asphalt Cements, J. Mater. Civ. Eng., 1993.
Le Guem et al., Physico-Chemical Analysis of Five Hard Bitumens: Identification of Chemical Species and Molecular Organization Before and After Artificial Aging, Elsevier Ltd., France, Apr. 29, 2010.
Lesueur, The Colloidal Structure of Bitumen: Consequences on the Rheology and on the Mechanisms of Bitumen Modification, Eurovia España, Pol. Ind. Villapark—Avda Quitapesares, Madrid, Spain, Sep. 9, 2008.
McCann et al., Instrumental Method Suitable for the Detection of Polymers in Asphalt Binders, U.S. Forest Service, Region 8—Engineering, Western Research Institute, Georgia, Wyoming, Jul. 20, 2007.
Pribanic et al., Use of a Multiwavelength UV-VIS Detector with HP-GPC to Give a Three-Dimensional View of Bituminous Materials, Transportation Research Record, France, Montana.
Redelius et al., Relation Between Bitumen Chemistry and Performance, Elsevier Ltd., 2014.
Schabron et al., Molecular Weight Polarity Map for Residua Pyrolysis, Elsevier Science Ltd., Laramie, WY, Jun. 9, 2000.
Wahhab et al., Prediction of Asphalt Rheological Properties Using HP-GPC, Journal of Materials in Civil engineering, Feb. 1999.
Vo-Dinh, Multicomponent Analysis by Synchronous Luminescence Spectrometry, Analytical Chemistry, Oak Ridge, Tennessee, Mar. 1978.
Zander et al., Regularities in the fluorescence spectra of coal-tar pitch fractionsCastrop-Rauxel, FRG, Miilheim a.d. Ruhr, FRG, May 16, 1990.
Kershaw, Fluorescence Spectroscopic Studies of Mesophase Formation, Fuel, Victoria, Australia, Oct. 18, 1994.
Groenzin et al., Asphaltene Molecular Size and Structure, J. Phys. Chem., Ridgefield, Connecticut, Jul. 27, 1999.
Groenzin et al., Molecular Size and Structure of Asphaltenes from Various Sources, Energy & Fuels, Ridgefield, Connecticut, Feb. 10, 2000.
Buenrostro-Gonzalez et al., The Overriding Chemical Principles that Define Asphaltenes, Energy & Fuels, Ridgefield, Connecticut, Apr. 10, 2001.
Ancheyta et al., Extraction and Characterization of Asphaltenes from Different Crude Oils and Solvents, Energy & Fuels, Mexico, Dec. 21, 2001.
Ryder, Quantitative Analysis of Crude Oils by Fluorescence Lifetime and Steady State Measurements using 380-nm Excitation, Society for Applied Spectroscopy, Galway, Ireland, 2002.
Groenzin, Molecular Size of Asphaltene Solubility Fractions, Energy & Fuels, University Park, Pennsylvania, Sep. 26, 2001.
Buch, Molecular Size of Asphaltene Fractions Obtained from Residuum Hydrotreatment, Elsevier Science Ltd., Lyngby, Denmark, Mexico, Dec. 12, 2002.
Riveros, Determination of Asphaltene and Resin Content in Venezuelan Crude Oils by Using Fluorescence Spectroscopy and Partial Least Squares Regression, Energy & Fuels, Caracas, Venezuela, Oct. 14, 2005.
Badre, Molecular Size and Weight of Asphaltene and Asphaltene Solubility Fractions from Coals, Crude Oils and Bitumen, Elsevier Science Ltd., Ridgefield, CT, Sendai, Japan, May 31, 2005.
Schneider et al., Asphaltene Molecular Size by Fluorescence Correlation Spectroscopy, Energy & Fuels, Cambridge, Massachusetts, Terre Haute, Indiana, Jun. 20, 2007.

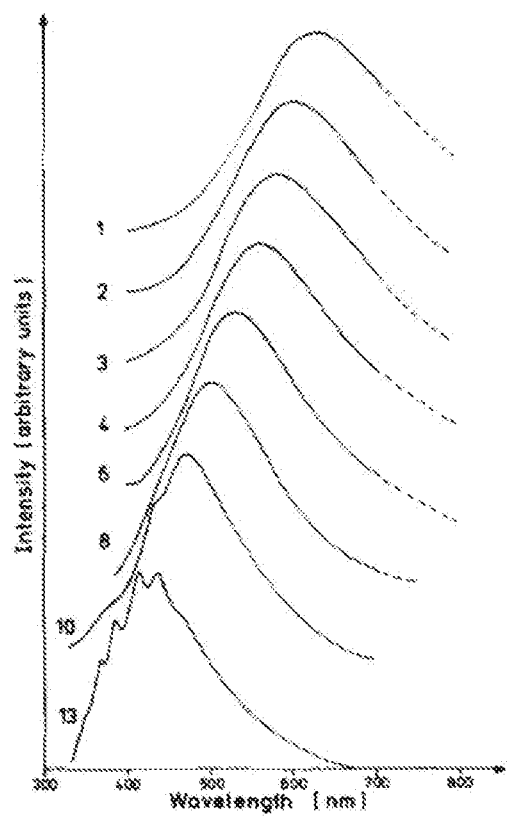 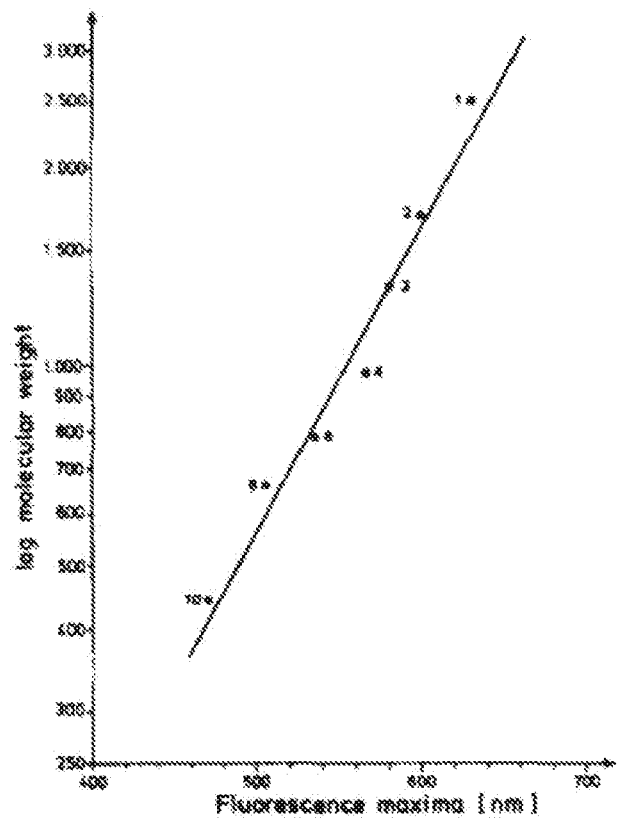
Fig. 16A
Fig. 16B

METHODS FOR ANALYZING HYDROCARBONS AND HYDROCARBON BLENDS FOR CHEMICAL COMPOSITIONS

This application claims priority to US Provisional App. No. 62/582,808 filed Nov. 7, 2017, and is a continuation-in-part application of application Ser. No. 15/167,766, filed May 27, 2016, which is a continuation of U.S. application Ser. No. 13/237,568, filed Sep. 20, 2011, each of said applications and patents incorporated herein in its entirety by reference.

GOVERNMENT LICENSE RIGHTS

This invention was made with government support under FHWA Contract DTFH61-07-D-00005 awarded by the U.S. Department of Transportation. The government has certain rights in the invention, including "march-in" rights, as provided for by the terms of U.S. Department of Transportation under FHWA Contract DTFH61-07-D-00005.

BACKGROUND OF THE INVENTION

Knowing the chemical composition of hydrocarbons (including but not limited to petroleum oils and asphaltic materials) is critical in applications such as improving the performance of bituminous roadways, bridges, roofs or other infrastructure, as well as improving refining and oil production efficiency or even in forensic applications such as the identification of the nature of pollutants in case of environmental catastrophes like oil spillage, or the nature of defective products in case of early asphalt pavement failures, to name a few. Certain embodiments of the inventive technology disclosed herein combine innovative features that provide a comprehensive, automated separation of oils in a manner that has not yet been achieved. This separation provides quantitative information about the relative amounts of several fractions using automated, normal phase chromatography coupled with a novel solubility-based separation of asphaltenes, saturates, naphthenes, two subfractions of aromatics, polars (resins), and three solubility subfractions of asphaltenes. The generated data provide valuable insight into compositional differences between different oils and asphalt binders, and various additives, polymers or modifiers, the internal chemical changes which occur due to aging or processing, modification, blending, and processing generally. The results can be used in establishing compatibility, blending, formulating, modifying and for predictive modeling, process control, and improving processing efficiency and yield, inter alia.

Adsorption Chromatography Petroleum Separations:

Separating a material into its constituent parts is often necessary in defining its composition. Separations of oils using normal phase chromatography have been around for several decades. One early version of such type of analysis was developed by Corbett who separated asphalts into saturate, naphthene aromatic, polar aromatic and asphaltene fractions.

A similar procedure was described by Jewel et al., in which crude oil or asphalt was separated into saturate, aromatic, resin, and asphaltene (SARA) fractions.

Using well known procedures, before these separations can be performed, the oils are usually first separated into two solubility classes by a gravimetric separation utilizing a low polarity hydrocarbon solvent such as isooctane, pentane, or heptane. The soluble material is by definition called the maltenes or petrolenes. The insoluble material is, by definition, called asphaltenes. The gravimetric asphaltenes/maltenes separation typically takes 24 hours. The chromatographic separation of maltenes takes another day. Certain conventional techniques to separate the maltenes employ gravimetric open-column normal-phase adsorption chromatography using polar stationary phases such as activated silica gel or activated aluminum oxide. If the asphaltenes are to be further separated gravimetrically into two solubility subfractions such as cyclohexane soluble and cyclohexane insoluble, it may take an additional day.

Again, using conventional methods, the maltenes are often separated into three fractions by normal-phase liquid chromatography: saturates, aromatics, and resins/polars. The saturates fractions consist of both linear, branched and naphthenic fully saturated organic molecules of low polarity containing carbon and hydrogen and essentially no heteroatoms.

A molecule in the aromatics fraction contains mainly carbon and hydrogen, possibly some thiophenic sulfur, few if any heteroatoms, and is distinct from the saturate fraction by containing one or more aromatic rings. The resins and asphaltenes fractions both contain many aromatic rings including highly colored pericondensed aromatic structures, with many polar substituents.

Rod Chromatography:

Approaches for SARA separation can be divided into two main groups. The first method that has been widely utilized uses a technique known as thin-layer chromatography (TLC), and when combined with flame ionization detection (FID) becomes semi-automated. This is known as the Iatroscan method in which capillary thin layer chromatography is conducted with whole oils on silica or alumina rods as a stationary phase, followed by evaporating the elution solvent and then slowly passing the rods through the flame of a flame ionization detector to provide information on the relative amounts of the fractional zones on the rod. The Iatroscan system typically elutes the fractions in a sequence of solvents consisting of a linear alkane, cyclohexane, toluene, and dichloromethane: methanol mixtures. However, the Iatroscan method has severe drawbacks including variable response factors for the different fractions, relatively high amounts of polar compounds retained near the spot location on the TLC rod, and aromatics grouping together to act like resins during separation. The separation is not very repeatable and there is a chronic problem with the strongly adsorbed, asphaltene material which does not migrate up the rod.

Column Chromatography:

The second type of method requires initial precipitation of the asphaltenes by dissolving the sample in an excess of an alkane before further separation of the maltenes into the saturate, aromatic, and resin (SAR) fractions by liquid chromatography. Typical methods for the asphaltene separations are described in ASTM D3279, ASTMD4124 or similar. Many variations of the SAR separation have been developed using amino, cyano, or alumina columns including several automated or semi-automated methods utilizing high performance liquid chromatography (HPLC).

Radke et al. described a semi-automated, medium pressure liquid chromatography system to separate maltenes involving three analytical columns and three pre-columns in which the pre-columns had to be re-packed between each injection. Variations for automated separations of the maltenes are typically performed using silica gel derivatized with aminopropyl or cyano functional groups. These typically do not provide fully resolved separations of saturates and aromatics and irreversible adsorption occurs on the columns due to resins and soluble asphaltene-type component molecules. A published version of an HPLC SARA method in the laboratory that uses chemically bonded aminosilane stationary phase for an automated SAR separation of crude oil maltenes has been evaluated and, while the authors claim that it also works on bituminous material, no data were presented to support this assertion and attempts to desorb the most polar fractions of asphalt from their system were unsuccessful, resulting in poor recovery and fouling of the column. Fan and Buckley developed a method that used two aminosilane columns. However, HPLC SARA methods that use chemically bonded aminosilane stationary phase of crude oil maltenes result in fouling of the column because of irreversible adsorption of resins. While their system appears to work well for crude oils, the most polar components of the resins fraction of asphalt became irreversibly bonded to the column. Further, the saturates and aromatics fractions are not completely separated in the Fan and Buckley system. It was evident that a new system was needed for asphalt and heavy oils that performs the SAR separation without fouling the column and that allows full recovery of the resins fraction.

This inventive technology, in embodiments, is a SARA (saturates, aromatics, resins and asphaltenes) procedure that involves a novel combination of two modes of separation/analysis—an asphaltenic mode (which may be non-chromatographic and, instead, solubility based) and an adsorption chromatography mode dedicated to the separation and/or analysis of saturates and possibly also aromatics and resins—for hydrocarbons such as, e.g., bitumen and oils, including but not limited to petroleum oils, asphalt, coal liquids and shale oils.

The new techniques and capabilities provide more powerful methods to analyze extremely complex hydrocarbon blends. Unlike prior art, which separate hydrocarbon blends into very generic composition fractions, this new method allows much finer separation of compounds in multiple dimensions according to the following (in exemplary, non-exhaustive manner): their solubility parameters, their solubility elution behaviors, their chromatographic adsorption behaviors, their chromatographic desorption behaviors, their molecular weights, and their responses to varieties of configurations of detectors arranged to obtain chemical information and measurement of chemical moieties.

The SAR-AD (SARA) separation is greatly expanded to include additional detection capabilities for improved chemical compound analysis including quantitative applications, and the separation capability is broadened to include a chromatographic application to determine the molecular weight profiles of the analyzed samples, as described further below.

BRIEF DESCRIPTION OF THE FIGURES

All figure descriptions below may apply to at least one embodiment of the inventive technology.

FIG. 16A shows a graph representing shows the fluorescence emission spectra of SEC fractions coal tar numbered in order of decreasing MW. Figure taken from (M. Zander 1990).

FIG. 16B shows a graph representing the correlation of the log of the molecular weight determined by vapor pressure osmometry to the maximum of the emission spectra. Figure taken from M. Zander 1990.

SUMMARY OF THE INVENTION

Figure 1:
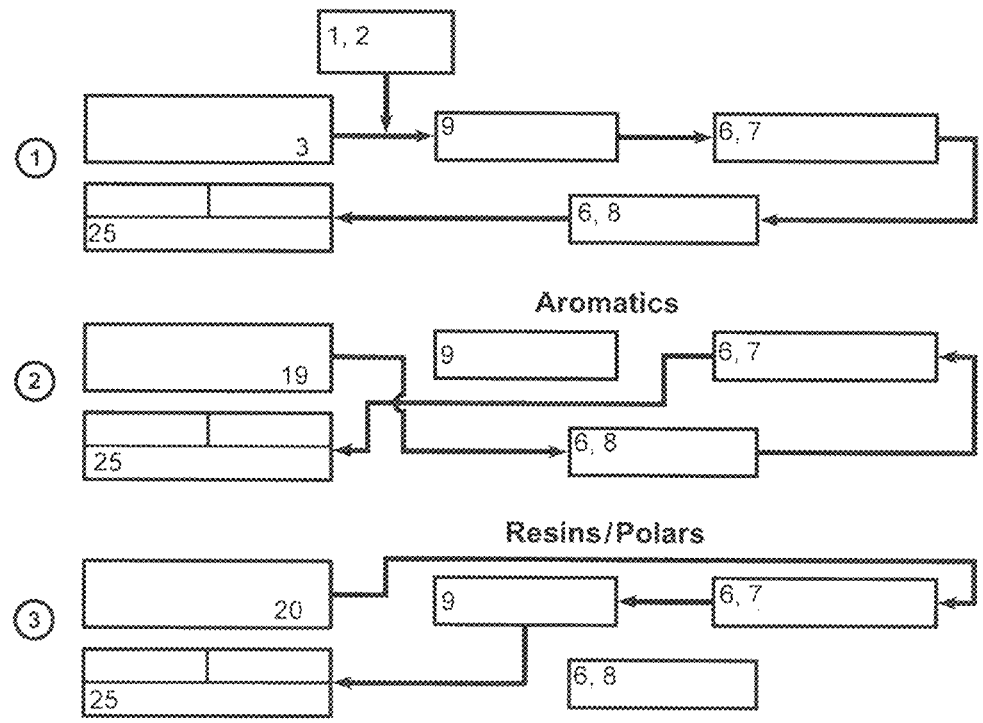
FIG. 1 shows a flow diagram for at least one embodiment of automated SAR separation of maltenes.

U.S. Pat. No. 9,353,317, describing a SAR (saturates, aromatics, resins)-AD system (SARA) and SAR system, inter alia, incorporated herein in its entirety, is a basis of sorts for this inventive technology. Inventive improvements disclosed in this application include additional chromatographic techniques and detection capabilities to greatly increase the amount of meaningful chemical information that can be obtained.

One primary novelty of particular SAR (SAR alone, or SARA) embodiments of the inventive technology disclosed herein is the use of non-porous high surface energy material to reversibly adsorb the most polar resins (and or the most aromatic polar fractions) from maltenes using a liquid chromatography system. The less polar materials can then pass through one or more subsequent columns packed with amino, cyano, silica or alumina stationary phases to separate the saturates, aromatics and remaining resin fractions. This invention is intended to include separation of any hydrocarbon including petroleum material such as residua, bitumen, crude oil, processed materials or products, asphalt, or non-petroleum materials such as additives or rejuvenators, and oil using a column packed with glass beads or other non-porous, high surface energy, typically non-polar surface packing such as metals or ceramics to reversibly adsorb the most highly active pericondensed aromatic resins material prior to any subsequent columns or separation schemes. Additional features involving enhanced detection and/or SEC analysis render the SARA system particularly useful in characterizing hydrocarbon components.

Aspects of the inventive technology may involve a novel combination of a solubility based asphaltene component fractionating and analysis method and an adsorption chromatography method for fractionating and analyzing saturate, aromatics and resins components of an input hydrocarbon.

The inventive technology may involve, in particular embodiments, novel use of a non-porous, high surface energy stationary phase to adsorb, in reversible fashion, the most polar component of a resins fraction of an input hydrocarbon when a mobile phase is passed over the stationary phase. Such reversible adsorption prevents irreversibly adsorption of such components on active stationary phase(s) downflow of the non-porous, high surface energy stationary phase, thereby conserving stationary phase costs and increasing resolution of resins elutions, and accuracy of hydrocarbon component results. Aspects of the inventive technology may also involve a novel combination of a solubility based asphaltene component fractionating and analysis method and an adsorption chromatography method for separating and/or analyzing saturate, aromatics and resins components of an input hydrocarbon, in addition to comprehensive detection, and SEC based detection.

One advantage of at least one embodiment of the inventive technology is increased accuracy in results relative to amounts of constituents of an input hydrocarbon.

One advantage of at least one embodiment of the inventive technology is an increase in distillate yield of a hydrocarbon that is analyzed (or, more particularly, a sample thereof that is analyzed). Such increase may stem from an enhanced or increased accuracy of results.

One advantage of at least one embodiment of the inventive technology stems from an ability to reuse a stationary phase over a plurality of "runs" through the separator apparatus (each run perhaps separating/analyzing a different hydrocarbon sample) without compromising accuracy of results of second or following "run(s)". Of course, such a capability may result in significant cost savings, as explained further herein.

One advantage of at least one embodiment of the inventive technology is an increase in speed of analysis. Indeed, using certain embodiments of the inventive technology disclosed herein, time from input of a hydrocarbon sample to be analyzed to elution, analysis, and/or generation of results may be less than that found in conventional methods.

One advantage of at least one embodiment of the inventive technology is a reduction in polluting emissions (given a certain distillate yield or a certain hydrocarbon input to be processed).

The present invention, in particular embodiments, generally relates to a significant and unexpected improvement of the specialized WRI fully-automated saturates, aromatics, resins-Asphaltene Determinator™ (SAR-AD) analysis through coupling the solvent based separations with destructive and non-destructive detectors, and the application of this improvement to analyze extremely complex hydrocarbons, particularly to analyze blends with additives and modifiers in a very broad terms.

The novel SAR-AD separation can now be coupled with a single or series of non-destructive detectors virtually anywhere in the system; detectors include but are not necessarily limited to:

Various spectroscopic techniques like Infrared, including Fourier-transform infrared (FTIR) and near infrared (NIR), multiple-wavelength detectors (MWD), variable-wavelength detectors (VWD), diode-array detection (DAD, also known as photo-diode array or PDA), fluorescence detection (FD), and refractive index detection (RID).

After column eluent/eluate has been directed to the non-destructive detectors, the novel SAR-AD separation can be coupled with destructive detectors such as:

Evaporative light scattering detection (ELSD) and intrinsic viscosity detection.

Additionally, the novel SAR-AD separation can now be designed to accommodate additional separation capabilities such as:

Various chromatographic techniques such as gel permeation chromatography (GPC, also known as size exclusion chromatography or SEC).

The various non-destructive and destructive method detectors can in turn be combined at various stages of the separation or of the detection to optimize and expand the availability of chemical information, to provide qualitative information such as the presence or absence of chemical moieties or additives, to provide quantitation of various chemical compounds and additives, and to determine the types of compounds indigenously present or subsequently added to complex hydrocarbon mixtures including, but not limited to, asphalt (bitumen) blends which may or may not contain a number of broadly-classified additives.

This newly improved SAR-AD method is called "SAR-AD Second Generation".

The results of the detection can be subsequently analyzed using any deconvolution or chemometrics software and including but not limited to, those based on neural networks, partial least squares, principal component analysis or the ExpliFit™ multi linear regression software from WRI which is especially useful for applications where insufficient observations are available compared to the number of independent measurement variables available. These chemometric software can be used for the identification and quantification of the molecule families and for the determination of mathematical relationships between analytical these chemical measurements themselves coming from the SAR-AD second generation, and further between chemical measurements and physical measurements.

One advantage of at least one embodiment of the inventive technology is generation of results from a SEC analysis system that includes a SEC column and a detector coupled to eluate to measure the eluate therefrom. Such results may provide information regarding a hydrocarbon, e.g., maltenes constituent makeup, that are improved relative to any known methods because of the absence of asphaltenes (which are prone to associate or agglomerate and therefore affect the accuracy and reliability of the SEC results) from the input to (and output from) the SEC column.

One advantage of at least one embodiment of the inventive technology is the generation of data afforded by the provision of detector(s) anywhere in the SAR, or SAR-AD system.

Other advantages of the inventive technology, in embodiments, may be as disclosed elsewhere in this specification, including the figures.

BRIEF DESCRIPTION OF THE PREFERRED EMBODIMENTS

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments are not meant to limit the breadth of other more encompassing claims that may be made where such may be only one of several methods or embodiments which could be employed in a broader claim or the like.

Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

In embodiments able to quantify asphaltenic constituents, one component of the combined separation is an automated solubility separation in which asphaltenes are precipitated within a ground polytetrafluoroethylene (PTFE)-packed column. This may be referred to as the Asphaltene Determinator (AD) separation, and may be as described in U.S. Pat. No. 7,875,464 (perhaps supplemented by disclosure herein), incorporated herein in its entirety. In the second component, the material which is not precipitated may be passed onto a series of adsorption chromatographic columns by normal-phase adsorption liquid chromatography for separation into saturates, aromatics, and resins/polars (SAR) components. The SAR (saturates, asphaltenes and resins) separation may utilize three separate adsorption chromatography columns packed with different sorbents. The first column may be packed with high surface energy, non-porous material to reversibly adsorb the very polar and highly aromatic resins materials to keep them from adsorbing irreversibly on the second (and perhaps the third) column. This packing can include a stationary phase such as glass beads, metal particles, ceramics, or other materials (perhaps generally, non-porous, high surface energy materials). The second column may be packed with a weakly adsorbing stationary phase (e.g., an activity reduced stationary phase) such as deactivated silica or amino or cyano functional groups bonded to a silica matrix (e.g., possibly to adsorb resins that pass through the first column). The third column may be a highly active, stationary phase such as activated silica or alumina (perhaps an activity enhanced stationary phase), e.g., to separate the aromatic components from the saturated hydrocarbon components. Flow switching and solvent switching valves may be used to provide a separation sequence in which the highly activated stationary phase is not "activity-reduced" (deactivated) during or between separations, allowing for repeated separations without requiring the stationary phases to be changed or discarded between runs. In a step separate from the adsorption chromatography separation of the maltenes, and perhaps after such adsorption chromatography steps are complete, the precipitated asphaltene material on the PTFE column may be re-dissolved using one or more asphaltene solvents (i.e. solvents able to dissolve at least a portion of the precipitated asphaltenes) to provide a solubility distribution profile of the asphaltene material. The result is a combined automated SAR separation coupled with the automated AD (Asphaltene Determinator) separation to provide a comprehensive characterization of materials. In certain embodiments, detectors may be placed anywhere in the system to, e.g., measure a response for any of the column eluates/flows. In certain embodiments, a SEC (size exclusion chromatography) column, may be configured (e.g., positioned, arranged and connected) so as to receive, e.g., maltenic, asphaltene-free eluate from the inert stationary phase column (a detector may be coupled to its eluate). Eyeball symbols used in the drawings show which flows/eluates may be detected; note that two or more flows may be detected using only one detector (via, e.g., flow direction, valving) termed a shared detector.

The SARA (saturates, aromatics, resins and asphaltenes), aka SAR-AD, procedure may involve a novel combination of two modes—an asphaltenic mode (which may be non-chromatographic and instead, solubility based), and an adsorption chromatography mode dedicated to the separation and/or analysis of saturates and possibly also aromatics and resins—for separation/analysis of oils including but not limited to petroleum oils, bitumen, asphalt, coal liquids and shale oils. In embodiments that resolve asphaltenic constituents, an initial step may be an automated solubility separation in which asphaltenes are precipitated within a ground polytetrafluoroethylene (PTFE)-packed column using a non-polar solvent, perhaps as disclosed in U.S. Pat. No. 7,875,464, or as disclosed herein (said patent incorporated herein in its entirety). In the second component, the material which is not precipitated in the first step may be passed onto a series of adsorption chromatographic columns for separation by normal-phase, adsorption, liquid chromatography into saturates, aromatics, and resins/polar aromatics (SAR) or other similar (e.g., naphthenic polar) components. The SAR separation may utilize three separate adsorption chromatography columns packed with different sorbents.

It is of general note that additional detail, e.g., regarding experimental setup and experimental results, inter alia, can be found in any of the SAR applications and patents incorporated herein, e.g., U.S. Pat. No. 9,353,317. Further, while certain description herein may focus on the use of the inventive technology in analysis, it should be understood that batch type processes are part of the inventive technology disclosed herein.

A substance, such as a hydrocarbon 1 (whether it be any of a variety of hydrocarbons, including but not limited to oils from fossil, biological or synthetic sources, or derived from biological/renewable oil sources (such as biomass), or oil shale, or even coal (perhaps using a Fischer Tropsch process), may be established or entrained into (and as part of) a first solvent mobile phase 3 via any well known manners (injection, for example). A hydrocarbon may be, as but a few examples, oil, crude oil, a constituent of oil (e.g., maltenes 2), bitumen, binder, light oil, heavy oil, dilbit (diluted bitumen), opportunity crudes such as heavy sour grades, oils and bitumen, extra heavy oil, high TAN crudes, asphalts, coal products, whether diluted in solvent solution or not. A mobile phase is that which is flowed through at least part of the apparatus, over one or more stationary phases. As such, the term mobile phase, before injection of a hydrocarbon, may be a solvent (e.g., heptane, in one example), but then, after injection, the same mobile phase may be that solvent with a hydrocarbon (e.g., a hydrocarbon sample) dissolved therein, or perhaps with substances desorbed or precipitated therein (and of course with substances removed therefrom).

The inert stationary phase 5 (in embodiments with a stationary phase), may be a substantially inert stationary phase, such that any reactivity is only, at the very most, de minimis (i.e., such that any reactivity does not unacceptably affect operational functionality). Typically, it may be nonpolar, and be very low friction. Adsorption to or within the inert stationary phase typically does not occur. An example of sufficiently inert stationary phase media include polytetrafluoroethylene (typically ground or rendered into particles (e.g., beads or smaller) in some manner). Saturates or other constituent components of oil (such as aromatics, resins, and asphaltenes) may be eluted (whether because, as may be the case for saturates, they are not adsorbed onto any stationary phase, or because, as may be the case with aromatics, resins or asphaltenes, they are desorbed from a stationary phase after being adsorbed onto that stationary phase (or, as is the case with asphaltenes, dissolved after being precipitated within a stationary phase). When a component of a hydrocarbon is eluted, it may come out of the column, existing in solution with the mobile phase, and pass through the apparatus to, e.g., an analyzer. Components of a hydrocarbon (e.g., saturates, aromatics, resins and asphaltenes, including subfractions thereof) may be as defined herein, or may have a common, well understood meaning to one of ordinary skill in the relevant art; additional information may be found in the Wiehe and Kennedy reference (cited in the information disclosure statement filed herewith, all of said references incorporated herein in their entirety), in addition to other incorporated, cited references.

Active sorbents 6 (e.g., porous active sorbents such as the active alumina and active silica stationary phases) can be activity reduced (or simply active, if the steps to reduce activity are not performed on the sorbent). Porous as used in this context may imply a porosity that is at or above the lowest porosity (volume of voids over total volume) that still allows for the adsorption intended; its precise value may change depending on the stationary phase used and/or the mobile phase passed over the stationary phase. Typically, an active sorbent will have been heated to remove surface water (e.g., heated to above 100 deg C. but below 500 deg C., or above 110 deg C. to 600 deg. C.). An activity reduced sorbent 7 (e.g., a weakly adsorbing stationary phase such as one including activity reduced silica or alumina), perhaps referred to conventionally as a deactivated sorbent, while still a type of active sorbent, may only be sufficiently active to adsorb resins (that may pass through the non-porous, high surface energy medium (e.g., glass bead stationary phase)), but sufficiently inactive so as to not adsorb aromatics, nor irreversibly adsorb the resins that it does adsorb. Non-porous in this context may imply a porosity that is at or below the highest porosity that still prevents adsorption as intended; its precise value may change depending on the stationary phase used and/or the mobile phase passed over the stationary phase. Activity of the activity reduced stationary phases may have been reduced by exposure of the sorbent (perhaps after the drying operation indicated above) to water or alcohol (perhaps in the form of the methylene chloride:methanol solvent mobile phase). Certain activity reduced stationary phases may be sufficiently inactive without such drying or deactivation procedures. Active stationary phases that have not undergone the deactivation process (such stationary phases may be conventionally referred to as activated media, such as activated alumina or activated silica, which may have only undergone a heat-induced drying), may be, but are not necessarily, referred to as activity enhanced stationary phases 8. Certain active stationary phases may even be a combination of activity enhanced and activity reduced stationary phases. Typically, the active stationary phase is porous, at least more porous than any non-porous, high surface energy stationary phase 8 such as glass beads, or metal or ceramic particles. It is of note that the need for an activity reduced column (e.g., a weakly adsorbing stationary phase) may be eliminated if the non-porous, high surface energy stationary phase has enough non-porous, high surface energy stationary phase (to eliminate the need for the activity reduced column). Further, while silica and/or alumina may be preferred active, porous stationary phases (whether activity reduced (conventionally referred to as deactivated), or activity enhanced (conventionally referred to as activated)), other normal phase chromatography sorbents may suffice, including but not limited to those with aluminum oxide, clay, bonded amino or cyano silica surfaces.

It is of note that the methods, and apparatus, described herein may be only separation methods or apparatus (where the goal is not to analyze a hydrocarbon relative to its constituent fractions, but instead to separate at least one constituent fraction thereof), or they may be only analysis methods (where the goal is not separation of at least one constituent fraction from a hydrocarbon, but rather analysis of a hydrocarbon, such as analysis of percentage composition of one or more of its constituent fractions), or they may be both (analysis and separation). In the case of analysis methods, even where, because a certain constituent of the input hydrocarbon is non-existent (e.g., there are no aromatics or resins), actual eluted amounts are zero, in such a situation, it is still said that the particular constituent that is intended to elute is in fact eluted (it's just that zero amount of it elutes). Diesel fuel, for example, may not have any resins (only saturates and aromatics).

As to the term "fluidic communication", it is of note that "A" can be in fluidic communication (whether controllable or otherwise) with "B" even if there's a non-conduit flow element (e.g., a stationary phase container) between the two. This stems from the fact that flow can, of course, pass through several flow elements (e.g., a stationary phase container(s)), before reaching a downstream flow element. The term container as used herein is a broad term, and includes but certainly is not limited to columnar containers. Generally, fluidic communication implies an ability of a fluid, at least at certain times (where any control devices that may impact that flow are adjusted to allow such flow), to flow from one component to another (via, e.g., any conduit such as tubes or piping). Further, more particularly relative to control of flow (i.e., where two or more components are in controllable fluidic communication), a valve change even several stationary phases upflow from a flow element can divert flow from that downflow flow element. As such, such "remote" flow components can be in controllable fluidic communication. Control of a fluid flow generally implies some sort of device or apparatus (flow control valve 10, such as a flow switching or solvent switching valve, as but two examples) that can allow for flow shut off, flow diversion, flow reduction, flow redirection, and/or flow increase, e.g. A flow switching valve may be a single valve that alone accomplishes a flow switch (e.g., from one mobile phase source to another, whether gradually or in step-wise fashion, and/or redirects that new flow to a different stationary phase container), or it may be one of two or more valves that together accomplish an intended flow switch (e.g., as where one valve shuts off flow from a mobile phase source and, either at that time or later, another valve opens flow from a different mobile phase source). Further, fluidic communication includes, but does not require, controllable fluidic communication, and fluidic communication does not require fluid flow at all times (because controlled fluidic communication can prevent such fluidic communication if, for example, a valve is switched to redirect flow). As to flow control componentry that serves to isolate a flow component (e.g., a stationary phase container such as columnar container), component A may be isolated from components B and C as long as flow through components B or C doesn't go through component A.

Additionally, as mentioned, switching from one mobile phase to another (a gradient) may be done either gradually with a gradual gradient or in step-wise (more abrupt) gradient fashion. Flow control componentry may be used to accomplish the intended transition. Of course, where a gradual change is desired, shutting off the earlier mobile phase and opening up the later mobile phase may occur more slowly than when a step-wise, abrupt change is desired. Steps involving flow of mobile phase don't mandate any particular transition, but instead include all possibilities given the indicated flow (e.g., from abrupt transition to very gradual transition, including gradients in between the two).

Of course, an important part of one aspect of the inventive technology is the use of a non-porous, high surface energy stationary phase 9 that is upflow of an activity enhanced stationary phase 8. Such may keep the most polar, aromatic resins materials away from the activity enhanced normal phase sorbent 8. The most polar, aromatic resins materials adsorbed onto the non-porous, high surface energy stationary phase are adsorbed reversibly (they can be desorbed easily from the non-porous, high surface energy stationary phase), whereas they would adsorb irreversibly on the activity enhanced porous stationary phase (i.e., such that they could not be desorbed therefrom), but for the non-porous, high surface energy stationary phase.

In particular embodiments of the inventive technology, flow componentry (e.g., valves) that causes resins desorbing mobile phase bypass of a highly activated stationary phase (see step 3 of FIGS. 1 and 3) may be used to prevent deactivation of that highly activated stationary phase. Such may allow for re-use of that stationary phase, or at least obviate a labor intensive, costly "re-activating" step for that stationary phase for it to be used during another run of the apparatus on a different hydrocarbon sample.

A main advantage of certain aspects of the inventive technology is that the apparatus/methods afford complete, and automated, resolution of the saturates and aromatics fractions. Other embodiments, supplemented with asphaltene fractioning steps and components (see FIGS. 3-6), resolve one or more of the asphaltene fraction, or resolves the entire asphaltene fraction upon providing compositional information thereabout. Further, one or more of the column packings (i.e., stationary phase media) used in the inventive technology may be less expensive than those typically used by conventional composition analysis schemes (such as very expensive aminopropyl bonded silica, a column of which costs approximately $800-$1000). The silica usable in the inventive method, and the glass beads and PTFE, are much less expensive. Further, conventional schemes often offer only non-resolved, or incompletely resolved, overlapping constituent peaks (e.g., saturates and aromatics peaks may overlap).

In particular embodiments, when there is no interest in characterizing an asphaltene portion of a hydrocarbon (see, e.g., FIGS. 1 and 2), maltenes in solution 2 may be injected into the first solvent mobile phase (from a first solvent source such as a first solvent container of a first solvent). The maltenes (the component of oil that is left after all or substantially all asphaltenes are removed, as by the conventionally known gravimetric precipitation and filtration asphaltene removal method) may thus be dissolved in a low polarity solvent (pentane, heptane, hexane, isooctane as but a few examples), perhaps as a result of the procedure that generates them, and then injected (in solution) into the first mobile phase 3 (which also may be a low polarity solvent such as pentane, heptane, hexane, isooctane as but a few examples). These two solvents may, but need not, be identical. At times, the oil of interest may have so little asphaltenes to start out with that the maltene generation procedure may be skipped; it may then possibly be input in undiluted form (presuming it is not overly viscous). For example, a light crude oil with relatively few asphaltenes could possibly be injected directly, without dilution by a strong solvent. It is of note that the term maltenes 2 (or any other component of oil) can be used in reference to pure maltenes (i.e., undiluted maltenes, with no solvent added), or maltenes in solution (i.e., as dissolved in a solvent, such as low polarity solvent). It is further of note that any of the apparatus may, as should be understood, during operation thereof, further comprise a mobile phase (e.g., a solvent mobile phase) running through the flow conduits of the apparatus; such mobile phase, of course, may have dissolved therein a hydrocarbon; the mobile phase may also have a desorbed hydrocarbon component (saturates, aromatics, resins desorbed from certain stationary phases) or asphaltenes dissolved therein.

Continuing, when there is no interest in characterizing an asphaltene portion of a hydrocarbon, the asphaltenes (when there are asphaltenes) may have first been removed from the original hydrocarbon, leaving maltenes (also deemed a type of hydrocarbon) (see FIG. 1). Again, this may be done using a well-known procedure (e.g., gravimetric precipitation and filtration), or even using a precipitant solvent. Then, in particular embodiments, a portion of the heptane soluble material (maltenes) in solution may then be injected into the first mobile phase so that it is brought in contact with the non-porous, high surface energy 9 column (e.g., glass bead stationary phase) and columns(s) with active stationary phase 6 (activity enhanced stationary phase 8 and possibly also an activity reduced stationary phase 7). Typically, the only precipitation seen in this scheme is the preliminary, a-columnar (without a column, or without a stationary phase) gravimetric precipitation and filtration of the asphaltenes (to create the maltenes). Reversible chromatographic adsorption of the highly aromatic and polar resins materials on the non-porous, high surface energy column precludes the adsorption of these same materials on the active (typically porous, whether activity enhanced or activity reduced) stationary phase(s) of the column(s) that are downflow (such adsorption would be a highly undesired reversible adsorption, requiring an expensive and time consuming replacement of such active (typically porous) stationary phases). Indeed, at least one aspect of the inventive technology involves successive use, for a different hydrocarbon sample, of a particular bulk quantity of one or more stationary phases (i.e., the very same particles of activity reduced silica, as but one example). Successive solvent mobile phases of increasing solvent strength may be added, with flow control valve(s) being used to bypass particular stationary phases (as particularly described elsewhere in this specification). Separately eluted components (after saturates) may be aromatics and resins.

The SAR/SARA separation of asphalt binders was finally enabled by the innovative use of a column filled with glass beads placed before the normal phase separation columns to remove the most pericondensed aromatic asphaltene-like molecules from the maltenes (which do not precipitate with asphaltenes). These molecules can then later be desorbed from the glass beads (or other non-porous glass, ceramic, or metal surfaces) using a solvent stronger than heptane. This is important because it is these components which typically, irreversibly adsorb onto normal phase sorbents that are based on silica gel with or without chemical modification, and aluminum oxide. This has been a hindrance to the successful, long term operation of automated SAR separations since a stationary phase with strongly adsorbed components must be discarded after each use because of the components that cannot be desorbed with a strong solvent. Another problem stems from the fact that strong solvents usually deactivate silica or alumina stationary phases such that such deactivated stationary phases are no longer able to fully separate saturates and aromatics. This requires that such stationary phases be discarded and changed frequently. The use of flow components such as switch(es) and/or valve(s) can, in certain embodiments, keep the third mobile phase 20 (e.g., $CH_2Cl_2$:MeOH) off of the activity enhanced stationary phase and prevent it from deactivating such stationary phase.

As mentioned, when there is an interest in using a fully automated, single hydrocarbon sample input procedure to characterize the asphaltenic component of a hydrocarbon, an input that has not had asphaltenes removed therefrom would typically be injected into the first mobile phase. In such case, a relatively strong solvent (e.g., chlorobenzene) that can dissolve the whole sample 12 and keep the asphaltenes in solution may be used to dilute the hydrocarbon 1 of interest because the oil is too viscous to be injected directly in undiluted form). An example is injection of 20 uL of a 10% (w/v) solution that includes 2 mg of a residuum or asphalt binder (bitumen). Even where an undiluted hydrocarbon is diluted in a solvent, and that solution is then input into a mobile phase, it is still said that a hydrocarbon is input into that mobile phase. If the oil were sufficiently non-viscous (sufficiently liquid), then a direct injection of 2 mg may suffice. After injection of the hydrocarbon (via controllable hydrocarbon input 65, where controllable merely implies an ability to start and stop the input, or merely allow input of a limited amount of hydrocarbon), the first mobile phase, which ideally may be any low polarity solvent (including, of course, a nonpolar solvent) that can precipitate some of the asphaltenes within the inert stationary phase, should suffice. Examples may include but are not limited to: hexane, heptane, isooctane and pentane. While a low polarity first mobile phase (for methods that characterize the asphaltenic fraction) may be preferred, it may not be necessary, as the critical requirement for this solvent is that it precipitates any portion of the sample (e.g., the asphaltenic portion). It is of note that the first mobile phase is preferably an alkane solvent regardless of whether the input hydrocarbon is a maltene or whether it includes asphaltenes. However, when the protocol involves asphaltene separation (for resolution thereof, as shown perhaps in FIGS. 4 and 8), the first mobile phase 3 should additionally be able to precipitate asphaltenes within the inert stationary phase.

Briefly, in certain applications, where there is an interest in using a fully automated, single hydrocarbon sample input procedure to characterize the asphaltenic component of a hydrocarbon (among characterizing other components), a hydrocarbon solution of whole oil 12 (i.e., that includes asphaltenes) in a strong solvent may be injected into a first mobile phase (heptane is one type of such mobile phase; other examples are listed herein) from a first mobile phase source 60. Thereafter, the asphaltenes precipitate within the inert stationary phase 5 (e.g., within the column with substantially inert stationary phase such as PTFE therein). The term "precipitation within a stationary phase", stationary phase container, or column indicates precipitation in the solvent mobile phase (e.g., in heptane) within the pores of the bed of the stationary phase (e.g., PTFE). Such precipitation is non-chromatographic. Steps, and components that follow (other than those related to the inert stationary phase or the asphaltenes themselves, or the use of solvent mobile phases specifically to dissolve precipitated asphaltenes), may be as seen in those embodiments that are not designed to also elute (and possibly also analyze) asphaltenes. The first mobile phase soluble material may continue on to the non-porous, high surface energy stationary phase and the remaining stationary phases (e.g., active stationary phases 6, whether activity reduced 7 or activity enhanced 8 or a combination of the two). Adsorption chromatograph occurs in such containers (e.g., columns). Aliphatic hydrocarbon material (saturates) may pass through all columns and elute first. The activity enhanced column (e.g., activity enhanced, or activated, silica) prevents the aromatics from eluting with the saturates (because the aromatics are adsorbed, reversibly, onto the activity enhanced column). The non-porous, high surface energy stationary phase 9 (e.g., glass bead) and any activity reduced stationary phase column 7 (e.g., activity reduced silica or activity reduced alumina, as but two examples), adsorb the resins material (perhaps referred to elsewhere herein as polars material). The most aromatic and polar resins materials are reversibly adsorbed onto the non-porous, high surface energy stationary phase instead of irreversibly adsorbed onto any of the active stationary phases (whether activity reduced or activity enhanced) that are downflow of it. Flow control valve(s) 10 may then be used to isolate the first column (the inert material column, which may preferably include PTFE) and the non-porous, high surface energy column. A second solvent mobile phase 19 (e.g., toluene or similar, which is stronger than the first solvent mobile phase), from a second solvent source 61, may then be backflushed through the active columns, but not the non-porous, high surface energy column, nor the inert stationary phase column; this backflush elutes aromatics. It is of note that any backflush or backflow of a mobile phase over a stationary phase typically involves backflow through that container (e.g., column), as where the flow direction through the column (e.g., of the second and third mobile phase) is opposite the flow direction of the first mobile phase through the column. While FIGS. 2 and 4-6 don't show such backflow (indeed, they show forward flow through the stationary phases), they do show a reversed order of flow of the second and third mobile phases as compared with the first mobile phase (for example, the second mobile phase hits the activity enhanced stationary phase before it hits the activity reduced stationary phase). During such reversed order of flow of the second or third mobile phases, either forward or back flow through the individual stationary phases is possible in embodiments of the inventive technology. Then, using a flow control valve(s), a third solvent mobile phase 20 (methylene chloride: methanol, chloroform:methanol, methylene chloride:ethanol, trichloroethane:methanol, cyclohexanone:methanol, as but a few examples), from a third solvent source 62, which is stronger than the second (and first) solvent mobile phases, may then be backflushed through the non-porous, high surface energy column and any activity reduced stationary phase that may be used, but not through the activity enhanced stationary phase (because the alcohol, e.g., methanol, would deactivate it), nor through the inert stationary phase. This elutes the polars (resins) that were adsorbed onto the non-porous, high surface energy column and any activity reduced stationary phase that may be used (perhaps resulting in two resins peaks).

Such columns—the non-porous, high surface energy stationary phase column, the activity enhanced stationary phase column, and any activity reduced stationary phase column that may be used—are then isolated using flow control valve(s), and the asphaltenes (or a portion thereof) of the inert stationary phase column (e.g., PTFE column) that were earlier precipitated within the inert column are dissolved using at least one asphaltene solvent. It is of particular note that the term asphaltene solvent is a solvent that can dissolve one or more asphaltenic components (i.e., at least a portion of asphaltenes) of a hydrocarbon. In order to gain more information on the compositions of different asphaltenes, solvents of increasing strength may be used. For example, a first asphaltene solvent mobile phase, from a first asphaltene solvent mobile phase source 22 (for the asphaltene dissolution stage) may be cyclohexane, with a second asphaltene solvent mobile phase from a second asphaltene solvent mobile phase source 23 being toluene, and a third (from third asphaltene solvent mobile phase source 24) being methylene chloride: methanol, with each dissolving a different asphaltene subfraction, resulting in the passage of this subfraction(s) to analysis componentry, if desired. The asphaltene dissolution protocol may be as disclosed in U.S. Pat. No. 7,875,464. Alternate mobile phases include but are not limited to benzene, xylenes, mixtures of cyclohexane and heptane, mixtures of toluene and heptane, chloroform, cyclohexanone. The result, in particular embodiments, is a fast, accurate method to fully characterize the composition of oils.

It is also of note that at times, only information regarding one constituent fraction of the oil, such as the saturates fraction, may be of interest. In such case, perhaps additional steps and components (e.g., additional mobile phases) that are non-essential to gleaning the desired information may be eliminated from the procedure. Further, regardless of whether the inventive method involves analysis (e.g., compositional determination) of asphaltenes, the need for a weakly adsorbing stationary phase (activity reduced stationary phase) may be obviated if a sufficiently large amount of the non-porous, high surface energy stationary phase is used. If such sufficiently large amount of the non-porous, high surface energy stationary phase is used, in certain applications, the activity reduced stationary phase may possibly be eliminated, resulting in a process that still provides acceptable resolution for the intended application. It is of note that FIGS. 1 and 3 show steps in at least a few embodiments of the inventive technology. As mentioned, depending on the goals of the separation/analysis, certain steps (e.g., the aromatics and resins elution steps (steps 2 and 3 of FIGS. 1 and 3), and the asphaltene elution steps (steps 4-6 of FIG. 3)) may be selectively, perhaps individually, eliminated. Further, depending on the goal(s) of the procedure, certain components may not be required. For example, if there is no interest in resolving an asphaltene component, then the inert stationary phase may not be necessary. If one is interested only in the highly alkyl substituted pericondensed aromatics fraction of the asphaltenes, then the other asphaltene solvents may be eliminated. Also, as mentioned, in applications where there is interest in resolving an asphaltene component, if enough of the inert stationary phase is used, the activity reduced stationary phase may be eliminated. It is also of note that the diagrammatic representations of the SAR and SARA separation and analysis apparatus as shown in FIGS. 2 and 4-6, respectively, each show only one possible way of using flow control valves so as to achieve the flow of the mobile phases as intended (e.g., to their intended stationary phases). Upon presentation of this disclosure, other arrangements could be designed by one of ordinary skill in the relevant art.

As should be understood, aspects of the inventive technology may involve high surface energy materials (e.g., the non-porous, high surface energy media, such as glass beads, of one of the stationary phase columns). Such high surface energy material will have a surface energy (perhaps otherwise known as surface free energy or surface tension) of greater than or equal to 100 mN/m; other types of such material may perhaps have only greater than or equal to 40 mN/m. Generally, high surface energy material implies a surface energy greater than or equal to 40 mN/m. Onto this high surface energy material is adsorbed components of the oil (such as very aromatic material, inter alia) that themselves typically have surface energies that are from about 40-100 mN/m. As to the weakly adsorbing stationary phase (when used), such as activity reduced silica or activity reduced alumina (as but two examples)—in one example it is any stationary phase (such as a porous sorbent) that is activity reduced via exposure of the sorbent (perhaps after a surface drying via heating operation indicated elsewhere in this description) to water or alcohol (perhaps in the form of the methylene chloride:methanol solvent mobile phase). It is also of note that where the viscosity of an input oil is greater than, e.g., 20 cP, there may be a need to dilute such oil with a solvent before injecting it into the first mobile phase.

Often, the purpose of any of the inventive methods disclosed herein is analysis of the input hydrocarbon; typically, that analysis means a characterization in some manner (typically numerically) of one or more of the various constituents of the input hydrocarbon (e.g., saturates, aromatics, resins, naphthenes, asphaltenes, subfractions of polars, and solubility subfractions of asphaltenes, as but a few examples). Often, that characterization relates to the amount of the constituent(s) of interest in the hydrocarbon, whether on a percentage or other basis, where that constituent(s) of interest is eluted from the apparatus. Analysis componentry 25 may include, but is not limited to well-known detectors, such as ELSD (evaporative light scattering detector), optical absorbance (which include UV and visible), refractive index, CAD (charged aerosol detector), and other spectrometers. Information gleaned from analysis can additionally, or instead, aid in assessing compatibility of the oil or hydrocarbon material associated with the input hydrocarbon (e.g., maltenes, or perhaps one containing asphaltenes) conducting predictive modeling, selecting feed (unprocessed hydrocarbon input) for process optimization, and effecting process control. It is also of note that current methods, whether because of unresolved peaks of eluted materials or for other reasons, do not afford the accuracy afforded by the instant inventive technology. Further, high costs associated with non-reusable stationary phases may force some refineries at times to forego any SAR or SARA determination whatsoever. Regardless, refineries (a term that includes but certainly is not limited to laboratories that analyze hydrocarbons) using conventional technologies are processing hydrocarbons with limited information about them (e.g., about coking onset) and their compositional makeup. As such, in order to avoid coke formation, or form only a small amount of coke during processing (or in order to avoid fouling of catalysts and/or heat exchanges, or only cause minimal fouling, or in order to avoid or minimize formation of emulsions in desalters, all during or as a result of processing), relatively conservative processing conditions are used. Indeed, the lack of information about the unprocessed (or partially processed) input hydrocarbon causes process operators to not produce as much end product(s) (e.g., gasoline, fuel oil, lubricating oils, diesel fuel, kerosene, jet fuel, tar, heavy fuel oil and asphalt) as could possibly be produced if they had more accurate, reliable information regarding compositional makeup, and could "push", or further adjust processing conditions (residence time, pressure, temperature, catalyst use, etc.), to produce more product while still avoiding coke formation (or only forming an small amount of coke) or experiencing other undesired outcome (e.g., any or too much fouling, unacceptable amounts of emulsion generation in desalters). The more accurate the information, the more efficient the process is because, e.g., coke onset estimation becomes more accurate as a result. As such, particular embodiments of the inventive technology disclosed herein enable greater end product production—a supplemental end product, or an end product not produced using conventional technology for a given hydrocarbon processor input (refinery input). In this way, carbon dioxide and other undesired emissions (such as SOx, NOx, as but a few examples, all generally termed pollutants) can be reduced for a given production of a hydrocarbon end product (or a supplemental amount of oil can be produced for a certain amount of emissions, or for a given hydrocarbon processing expenditure, or for a given emissions allotment, allowance or expenditure). Such efficiency has obvious cost savings implications and, if a cap and trade scheme is ever legislated, will result in emissions credits associated with this "reduced emissions per produced end product" that, having a monetary value (estimated in 2011 to be from $20/ton to $140/ton, which may indeed change depending on the market conditions), can be traded on the market. Indeed, the owner of the inventive technology claims that market value, in addition to the supplemental oil per hydrocarbon input, or per emissions output afforded upon use of the inventive technology, inter alia.

As an example of calculations that suggest the magnitude of costs savings attributable to the inventive technology based on an estimate of 2.3 million barrels of heavy ends per day of thermal cracking and coker feed that can be produced from distillation operations in the U.S., an industry-wide 1% increase in distillate yield (end product) from safely cutting deeper into a heavy oil during distillation (perhaps a low end, conservative estimate) would result in about 23,000 bpd of supplemental end product, worth approximately $230,000/day, assuming a differential price between residua and distillate of $10/bbl. Further, there would be significant energy savings involved using aspects of the inventive technology, as coking operations use about 166,000-258,000 Btu per barrel of feed (USDOE 1998). For each 1% decrease in thermal cracking and coker feed (near 23,000 barrels per day in 2011, (USEIA 2011)), there would be a potential energy savings of about 3.8-5.9 billion Btu for residua that do not need to be heated for coking, since they will have been recovered in an optimized distillate stream. This also corresponds to a lowering of carbon dioxide from fuel that is not burned in coking operations. Residual fuel used as the heat source produces about 174 pounds of carbon dioxide per million Btu generated. Thus, in the U.S., the reduction in carbon dioxide emissions for each 1% industry-wide distillation efficiency improvement may be about 331-515 tons per day (2011 figures). Given the above-mentioned monetary per ton emissions estimate ($20-$140/ton), at 515 tons/day (188,000 tons/yr), which certainly could increase, market value for avoided $CO_2$ emissions (valued according to market value of traded emission credits) could be $3,760,000/yr up to $26,320,000/yr for each 1% gain in efficiency. So, a 5% efficiency gain would yield $18,800,000 to $131,600,000/yr in $CO_2$ emission value. Of course, actual savings/costs/value could be greater (including the 1% gain); these are merely estimates.

SAR/SARA+Detection: In particular embodiments (see, e.g., Examples 1-4 below), some thing, e.g., an eluate (which may include a fraction, e.g., an asphaltene fraction), may be analyzed. This may involve the step of measuring at least one response (which includes perhaps first obtaining that response) for at least one of such thing(s), e.g., eluate, using at least one detector (where an eluate that may be detected may be indicated with an "eyeball" symbol). Measuring a response (e.g., a refractive index response, as but one of many possible responses) may include measuring a change in response and/or comparing that response to a standard response. Embodiments may further comprise the step of determining the amount of at least one analyte (e.g., a specific compound of interest) of at least one eluate or fraction (or other thing) based on (e.g., via the mathematical or other use of) said at least one response. As such, a detector established to measure a response for an eluate or fraction, e.g., can be mounted according to well-known methods so that it can "detect an analyte" (e.g., via measuring a response that varies depending on, e.g., an amount of that analyte) of that eluate/fraction. Such a detector may thus be "coupled to an eluate." It is also of note that measuring a response for an eluate may include measuring a response for only part of that eluate.

Figure 2:
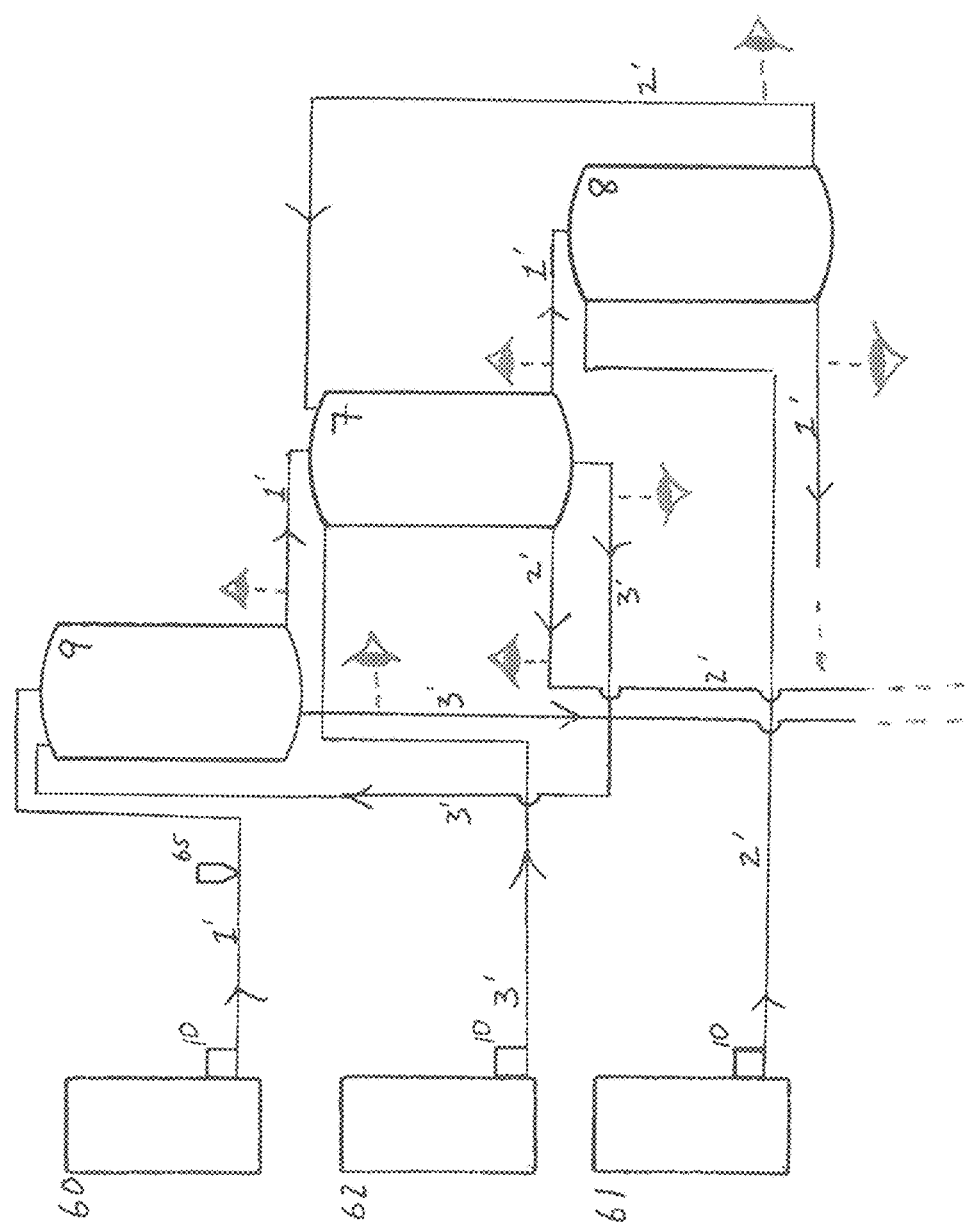
FIG. 2 shows at least one embodiment of an apparatus that is particularly suited for SAR resolution, showing some of the many possible flows/eluates that may be detected (see "eyeball" symbol).
Figure 3:
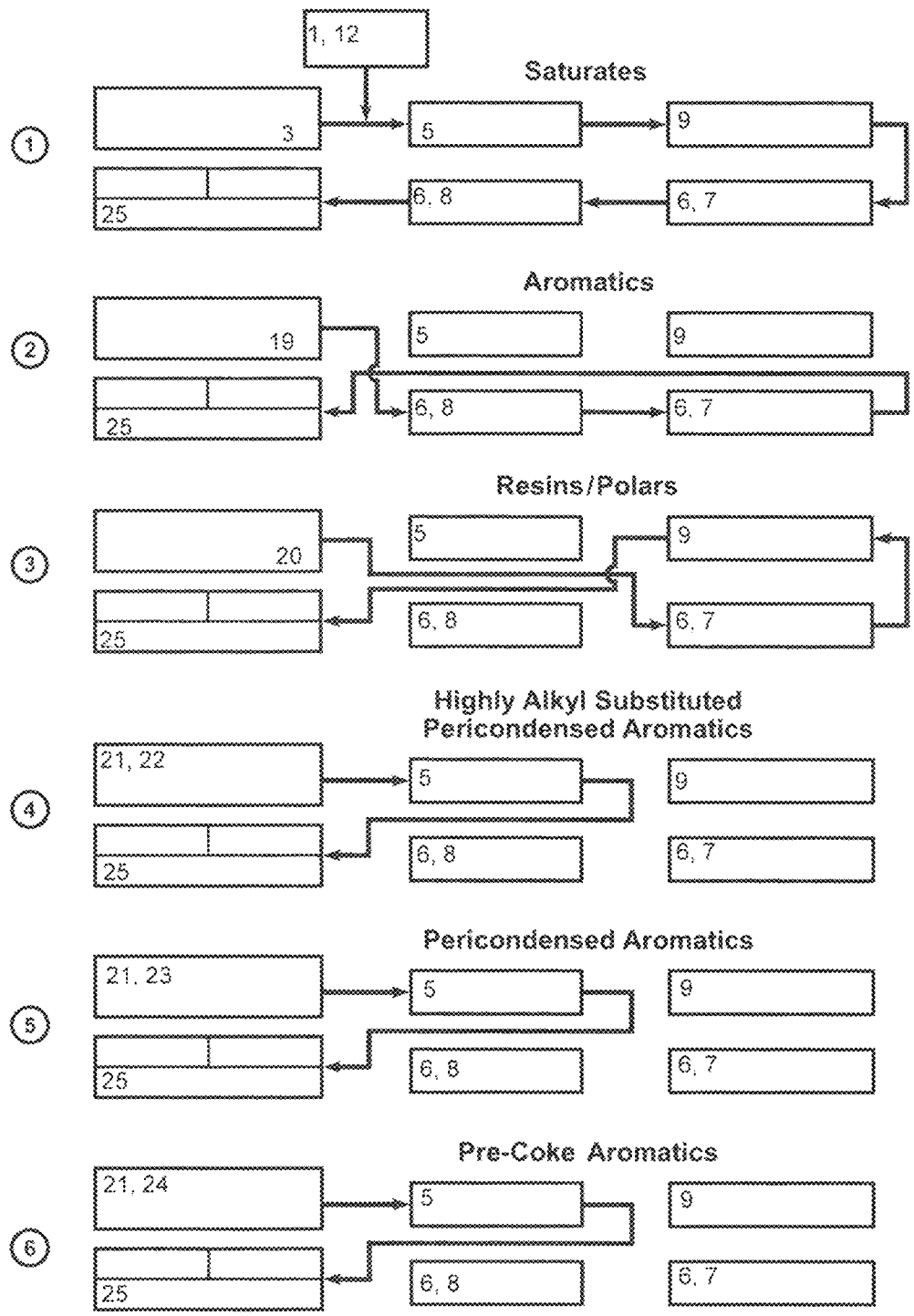
FIG. 3 shows a flow diagram for at least one embodiment of automated SAR separation of maltenes, coupled with an AD (asphaltene determinator) system (i.e., SARA, or SAR-AD).
Figure 4:
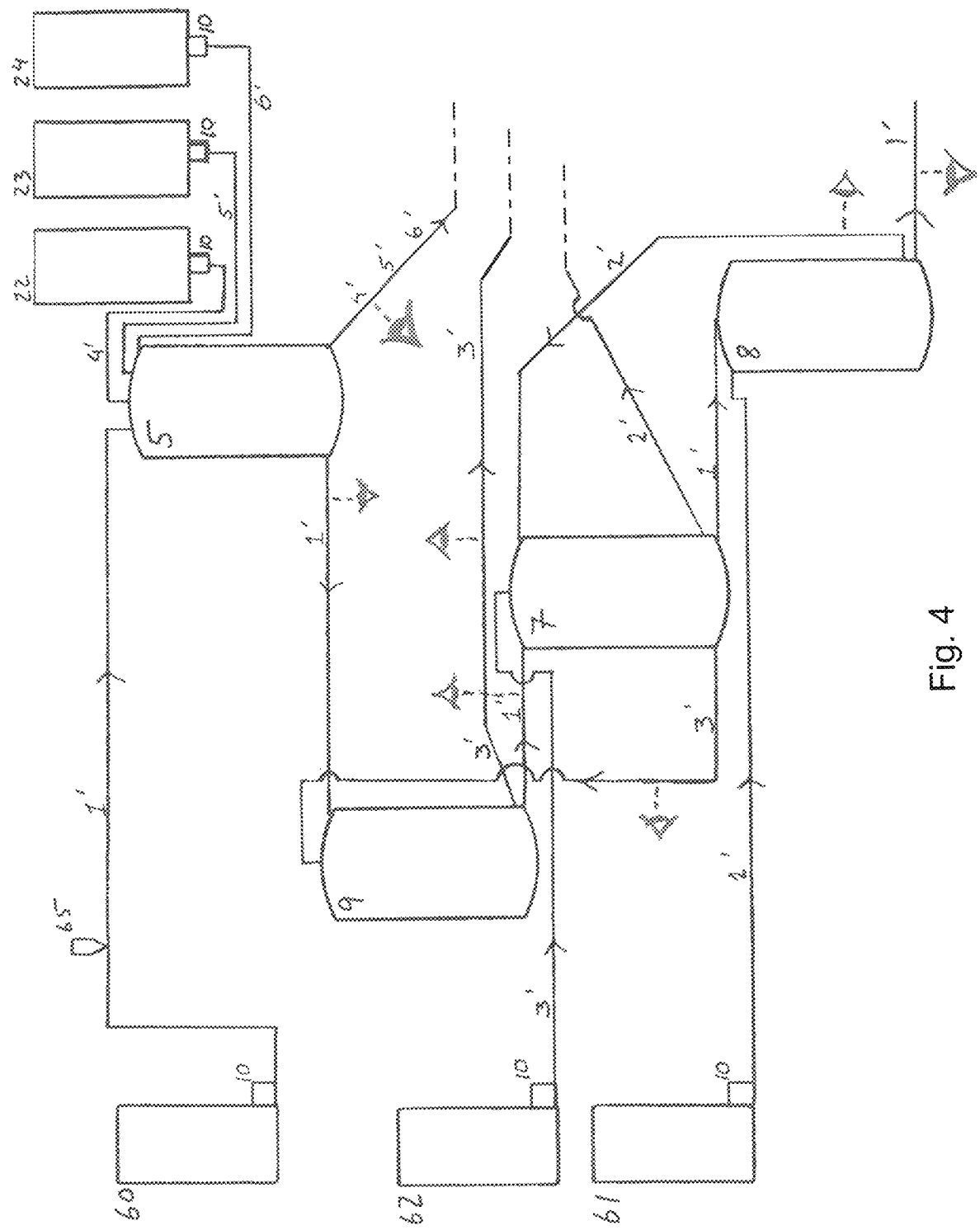
FIG. 4 shows at least one embodiment of an apparatus that is particularly suited for SARA resolution, showing some of the many possible flows/eluates that may be detected.

As shown in exemplary manner in FIGS. 2 and 4, detectors (possible sites shown via "eyeball" symbols) can be placed anywhere in a SAR type flow system in order to analyze any components of the hydrocarbon. Note that, if desired, two or more "eyeball" symbols can be handled by one detector. FIG. 2 (corresponding to the schematic of FIG. 1) shows a more basic system where the entrained hydrocarbon 65 is free of asphaltenes upon its injection into the first solvent mobile phase (e.g., heptane, as but one example). Columns 8, 7, and 9, and steps associated therewith, are as described elsewhere in this application.

FIG. 4 (corresponding to the schematic of FIG. 3) shows a system capable of more thorough analysis, with (substantially chemically) inert stationary phase column 5, and asphaltene solvents (i.e., that are capable of dissolving at least a portion of precipitated asphaltenes). A first eluate (see 1' of FIG. 4, exiting column 5), generated upon passing the hydrocarbon, in first solvent mobile phase over inert stationary phase in presence of that solvent, may then be passed to one or more of columns 9, 7 and 8 as disclosed elsewhere herein. For example, that first eluate may be passed over a non-porous, high surface energy, adsorptive stationary phase (in column 9) (e.g., to reversibly adsorb thereon the highly polar aromatic components of the resins fraction (and possibly also the resins fraction)), thereby generating a second eluate. Note that such reversible adsorption may prevent reversibly adsorbed highly polar aromatics components of the resins fraction (and indeed also the resins fraction if it is indeed adsorbed) onto a porous, active stationary phase. That second eluate may then be passed, e.g., over the porous, active stationary phase, generating a third eluate. It is of note that even where only a portion of the entire eluate is indicated as, e.g., passed over a stationary phase or through a column, or directed via flow lines, that eluate is considered as having been so passed or directed. In order to provide detector-supplied information about the asphaltenes (and/or to clear the asphaltenes from column 5), at least one asphaltene solvent may be passed over the precipitated asphaltenes of the inert stationary phase (e.g., from solvent source 24 alone, or, if part of a successive dissolution procedure, from 22 and 24, or from 22, 23 and 24 (and perhaps others)). Dissolved asphaltenes (perhaps dissolved asphaltenic fractions) may appear in one or more asphaltenic eluates (see flows 4', 5, and 6'). Indeed, whenever substantially all precipitated asphaltenes in a column are dissolved and eluted therefrom, such may occur, e.g., as the result of passing a single strong (asphaltene) solvent (e.g., from source 24 alone), or instead as the result of passing multiple solvents of varying strength (e.g., as part of a successive dissolution procedure to gain information about the fractional composition of the asphaltenes), with the last of the solvents strong enough to dissolve any remaining precipitated asphaltenes. Further, any of a variety of detectors may be used to measure at least one response for at least one of any of such eluates.

Figure 5:
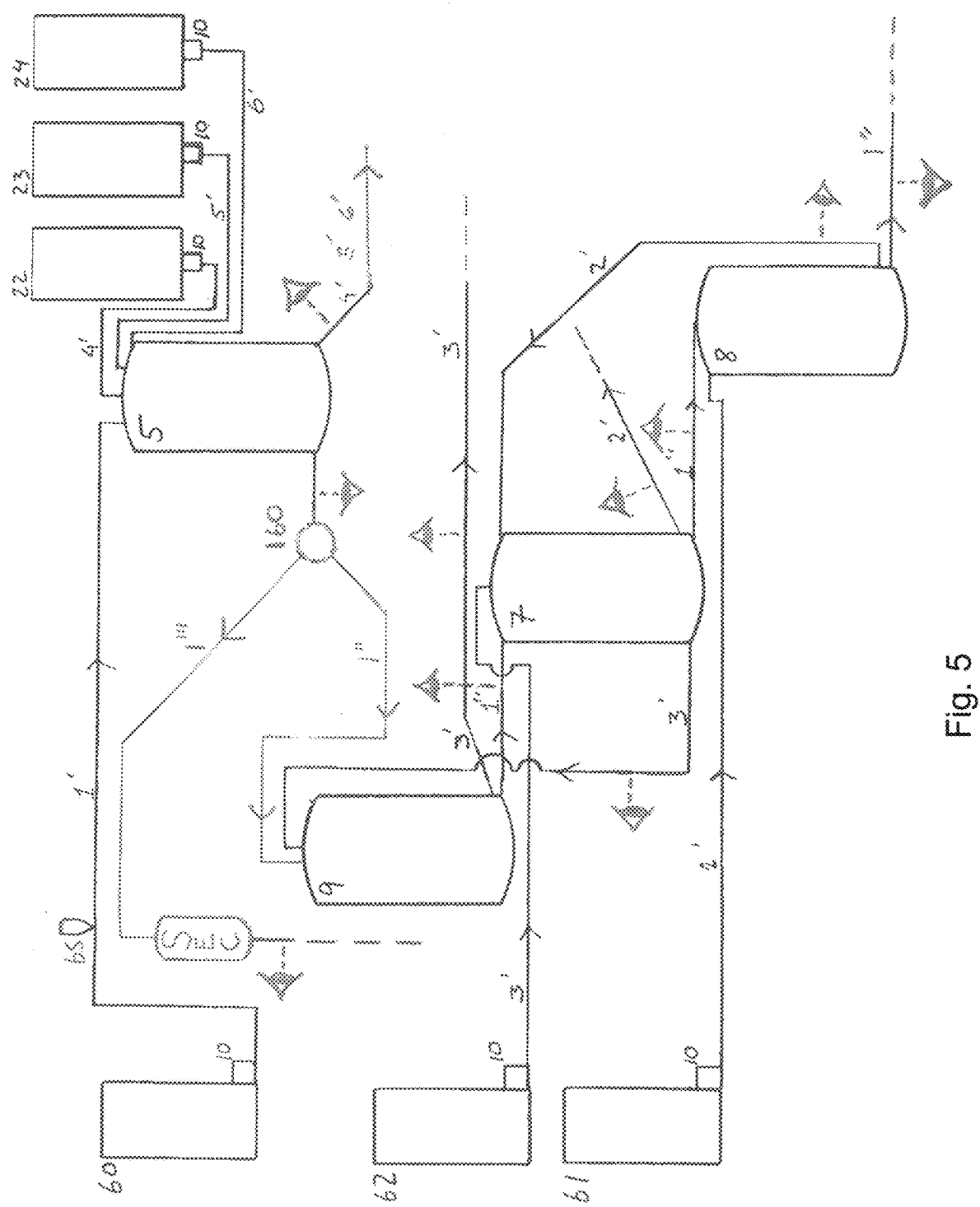
FIG. 5 shows at least one embodiment of an apparatus that is particularly suited for SARA resolution, and a SEC column coupled as a component thereof, and showing some of the many possible flows/eluates that may be detected, and a split flow valve.

SAR/SARA+SEC: FIG. 5 shows a single hydrocarbon (e.g., one portion of a sample) that is entrained into and as part of a first solvent mobile phase (flow 1'), such as flow of a precipitant solvent, though column 5 (i.e., over a (substantially chemically) inert stationary phase), precipitating substantially all of the asphaltenes of that (injected) hydrocarbon so as to generate a first eluate that is free of those precipitated asphaltenes. That eluate is split via flow splitting valve 160 (whether it splits flow 50/50 or in any other proportion), resulting in a first flow 1", which flows to the various columns 9, 7 and 8, in one embodiment, and a second flow 1''', which flows to the SEC column). Both flows 1" and 1''' may provide results that provide information about the maltenes of the input oil sample. First flow, may be passed over a non-porous, high surface energy, adsorptive stationary phase, generating a first flow, second eluate, and subsequently passing that first flow second eluate over a porous, active stationary phase, generating a first flow, third eluate (all steps of the SAR process that appear in FIG. 5 may be as described elsewhere herein in more detail, e.g., as with regard to FIG. 6). During such flow, or at least while it is initiated, the second flow 1''' may be passed through a size exclusion chromatography stationary phase (see SEC column) to generate a second flow, second eluate. At least one detector may be coupled to that eluate to measure at least one response for that second flow, second eluate (generally, a SEC column eluate). Note that the term valve as used anywhere in this application herein is a generally inclusive term, and even includes, e.g., processor or other controlled gating technology at the output of a column. Further, the numbering of eluates is merely used to help identify them as they are defined (e.g., the second flow, second eluate is the eluate of the second flow from the SEC column), and does not necessarily mandate a certain order of occurrence (e.g., there may be an intervening eluate(s) that occurs between a second and third eluate). It is of additional note that the term "substantially" means within 5% of the reference (e.g., within 5% of precipitating all asphaltenes).

Figure 6:
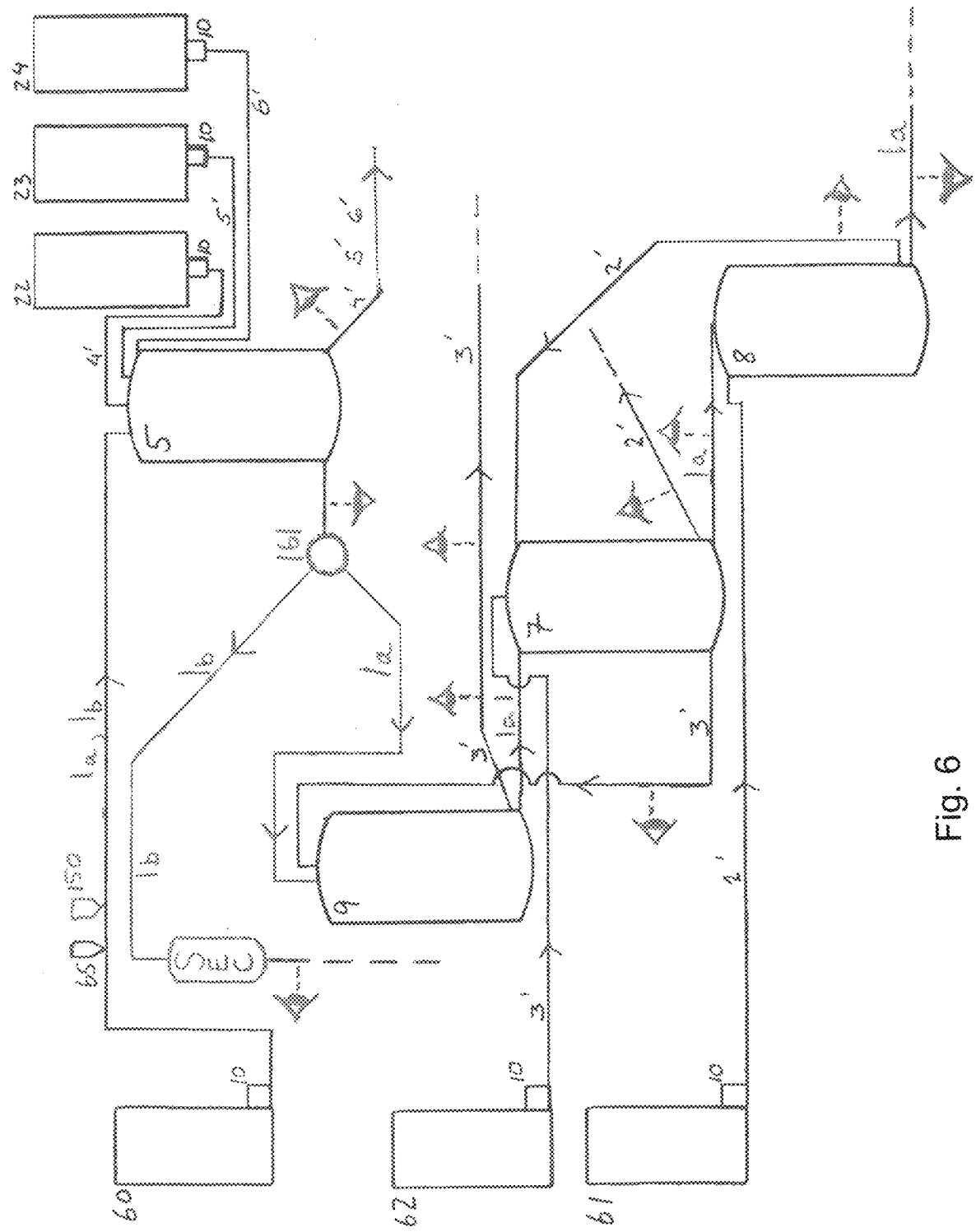
FIG. 6 shows at least one embodiment of an apparatus that is particularly suited for SARA resolution, and a SEC column coupled as a component thereof, and showing some of the many possible flows/eluates that may be detected, and a schematic of a two-way valve (one input and a selected one of two outputs, allowing for direction of flow to either SEC column during the SEA (size exclusion analysis) run of the first solvent mobile phase, or to inert stationary phase column 9 during a SBA (solubility-based analysis) run of the first solvent mobile phase.

FIG. 6 shows a similar system, but one that provides a two-way valve 161 (i.e., with one input and one of two alternatively selectable outputs) and involves two portions 65 and 150 of the same hydrocarbon sample, one portion 65 to be analyzed via solubility based analysis (SBA), such portion termed a SBA portion 65, and the other portion 150 to be analyzed via size exclusion analysis (SEA, involving size exclusion chromatography), such portion termed a SEA portion 150. Either analysis may be performed before the other, but each should pass the hydrocarbon portion (entrained in a first solvent mobile phase) over an inert stationary phase (substantially inert with respect to asphaltenes) that is free of asphaltenes (so, the first-performed analysis should involve, before the other analysis is started, a removal of asphaltenes (e.g., SEA portion precipitated asphaltenes if the SEA was performed first) retained on the inert stationary phase during that earlier performed analysis). Before the latter-performed analysis starts, the valve 161 should be switched (so that it directs flow towards equipment for the SEA (flow 1b after 161) or SBA (flow 1a after 161), whichever is other than the first performed analysis). The "run" of the first solvent mobile phase (a precipitant solvent such as, e.g., heptane) in which the SBA portion (of the hydrocarbon) is entrained is termed the SBA run (1a) of that mobile phase; the "run" of the first solvent mobile phase in which the SEA portion is entrained is termed the SEA run (1b) of that mobile phase. Again, the SBA or the SEA can be performed in any order; indeed, any numerical designation of eluates does not mandate a corresponding temporal order, and is used merely to facilitate identification.

More particularly as to the SBA (e.g., as shown in FIG. 6), it may involve the following: establishing the SBA portion of the hydrocarbon into and as part of a SBA run of a first solvent mobile phase; passing the SBA run of the first solvent mobile phase over an asphaltene-free inert stationary phase; precipitating substantially all of the SBA portion asphaltenes within the inert stationary phase to generate SBA portion precipitated asphaltenes and a first SBA eluate (from the column housing the inert stationary phase) that is free of the precipitated asphaltenes; subsequently passing the first SBA eluate over a non-porous, high surface energy, adsorptive stationary phase to generate a second SBA eluate; subsequently passing the second SBA eluate over the porous, active stationary phase; reversibly adsorbing substantially all of the aromatics fraction onto the porous, active stationary phase to generate a third SBA eluate; and eluting substantially all of the saturates (and possibly the significantly non-polar aromatics) as part of the third SBA eluate. The SBA analysis, particularly when it precedes the SEA analysis, may involve the steps of passing at least one asphaltene solvent over the inert stationary phase to generate at least one SBA portion asphaltenic eluate; and eluting substantially all of the SBA portion precipitated asphaltenes as part of said at least one SBA portion asphaltenic eluate (e.g., through use of asphaltene solvents from source 24, or 24 any one or more of 22 and 23 along paths 6' and any one or more of 4' and 5'), with detector(s) placed along asphaltenic eluate outlet path (see 4', 5', 6' downflow of column 5) in order to measure at least one response (e.g., to analyze the asphaltene fractions of the hydrocarbon). Note that a successive (precipitated asphaltene) dissolution procedure will involve the use of solvent from source 24 and from at least one additional source (e.g., of 22 and 23). Such additional flows of different solvents (e.g., from sources 62 and 61 may flow over any of columns 7, 8 or 9) in, e.g., the manner shown, may be performed where it is desired to obtain additional information about the maltenes (e.g., about the saturates, resins or aromatics components thereof). It is of note that anytime all precipitated asphaltenes are eluted or dissolved, that could be part of a successive dissolution procedure (e.g., using several solvents of increasing strength (e.g., increasing polarity), one after another) or simply achieved via use of a single solvent strong enough to dissolve all asphaltenes by itself. Further, detectors may be coupled to any of the eluates to obtain measurements for that eluate, thereby yielding information about, e.g., the presence/amount of an analyte (including but certainly not limited to resins, aromatics, saturates, asphaltenes, etc.).

More particularly as to the SEA (e.g., as shown in 6), it may involve the following: establishing a SEA portion of the hydrocarbon into and as part of a SEA run of said first solvent mobile phase, the SEA portion of said hydrocarbon including SEA portion asphaltenes and SEA portion maltenes; passing the SEA run of said first solvent mobile phase over the asphaltene-free inert stationary phase; precipitating substantially all of the SEA portion asphaltenes within the inert stationary phase to generate SEA portion precipitated asphaltenes and a SEA first eluate; passing the SEA first eluate through a size exclusion chromatography stationary phase to generate a SEA second eluate (e.g., from a column with that SEC stationary phase); measuring at least one response for the SEA second eluate using at least one detector; passing at least one asphaltene solvent over the inert stationary phase to generate at least one SEA portion asphaltenic eluate; and eluting substantially all of the SEA portion precipitated asphaltenes as part of the at least one SEA portion asphaltenic eluate.

Still referring to FIG. 6, where the SBA analysis is performed first, 150 is injected after 65 is injected, and indeed after precipitated asphaltenes of 65 are cleared from column 5 using, e.g., flow 6' from third asphaltene solvent mobile phase source 24 alone, or indeed after weaker solvents of sources 22 and 23 are used in addition. During flow 1a (i.e., during analysis of maltenes of 65), valve 161 directs all flow towards, e.g., column 9 (and not to SEC column); after the precipitated asphaltenes of 65 are cleared from column 5 (again, using solvent from, e.g., 24, or 24 and 23, or 24, 23 and 22), valve 161 is switched to direct all eluate from column 5 (with maltenes of portion/input 150 dissolved therein) to the SEC column (see flow 1b).

Such alternate processing, using two portions of the same hydrocarbon, one after the other (and after precipitated asphaltenes of the first are cleared from column 5) may avoid the difficulties associated with flow splitting valve 160 (indeed, selecting the best proportional split between the two flows may be difficult), and the roughly simultaneous SBA and SEA of maltenes of the same hydrocarbon portion 65 (see FIG. 5). SBA is achieved at least in part via columns 9, 7 and 8 (see flow 1", which may be followed by flows 2' and 3'), while SEA is achieved at least in part using SEC column (see flow 1'''). Note that FIG. 2 (corresponds with FIG. 1) shows how maltenes can be input directly (see 65) into the first solvent mobile phase in a truncated system that does not show equipment that acts as a site for precipitated asphaltenes (e.g., an inert stationary phase in a column), nor equipment that removes, via dissolution (dissolving) such asphaltenes therefrom. Note also that the disclosure and any and all claims filed or issued in any of the SAR priority applications (e.g., U.S. Pat. No. 9,353,317 and the application that it matured from) are incorporated herein as if set forth explicitly herein.

The results of any SEC analysis (e.g., via a SEC stationary phase (in a vessel) and a detector configured to measure at least one response for an eluate from that vessel) provide information for the various components' molecular size, weight, or volume for the sample that is input into that column (perhaps, e.g., as dissolved in a solvent such as heptane). Example 3 detailed below shows one of many possible manifestations of a SAR-AD+SEC system.

Note that, in keeping with a terminology as used certain priority applications, a mobile phase can be, e.g., a solvent mobile phase where it is "amended" to include a hydrocarbon, components thereof, or to be free of a hydrocarbon or components thereof. This would be understood by one of ordinary skill in the art, without its specific mention, however.

Note that vessels (e.g., columns) can be set in series, parallel, singularly, as multiples, arranged for precipitation, adsorption, size exclusion, etc. Embodiments of the inventive technology may feature, either alone or in combination, isocratic or gradient elution profiles, flow patterns, valves, step-wise or gradual (here defined as being not step-wise) changes to, e.g., the solvent at the pump, and/or gradual and continuous, inter alia. Solvents may be carefully chosen to improve elution capability and for overcoming detector limitations; solvents even can be changed, and even midstream or mid-detection, or at other times, in order to gain additional information regarding, e.g., one or more analytes. Different detectors can be combined in any of several ways, as different combinations may demonstrate different sensitivities to various analyte(s). And, while certain detectors may be best suited for placement after certain vessel(s) (e.g., columns) to detect specific eluate(s), the inventive technology generally, in embodiments, includes the use of detectors placed at various locations to detect analytes of any of a variety of eluate(s). The same may be true for placement of certain vessels, e.g., a size exclusion chromatography column (indeed, while it may be particularly useful (for detection of analytes in its eluate), to place a SEC column immediately after an inert stationary phase column (whether with valving therebetween or not), such column may offer illuminating information (e.g., when eluate therefrom has a detector (e.g., RI detector) coupled thereto) regarding, e.g., mass/volumetric sizes of the various components of that eluate.

Applications of the inventive technology, in embodiments, include but are not limited to: any exemplary applications described elsewhere in this technology, and process control, process refining, refining generally, analysis/review/testing/investigation of catalysts, rejuvenators, REOB (refined engine oil bottoms), additives, modifiers, polymers, contaminants, etc., estimation/prediction of fouling, coking, sediment formation, etc. And generally, embodiments of the inventive technology may manifest in or as a dedicated platform that is specific to a targeted test or analysis, or as a more universal platform with capabilities to achieve a wider analytical scope.

Particular embodiments of the inventive technology may even have application in continuous or batch, scaled up operations. Indeed, particular embodiments may help to improve control such operations.

Applications of the inventive technology also include controls of pollution and forensic analysis. The multi-detection capabilities of the mentioned separation would allow for detection and maturation evaluation of environmentally, possibly accidentally, released petroleum products in aquatic- and land-based environments. For example, but certainly not limited to, oil from oceanic crude oil spills may undergo significant and rapid changes due to air-oxidation and photo-oxidation, among other processes, which may cause crude oils released into the environment to take up a significant amount of oxygen, result in the formation of tar balls which persist in the environment and are difficult to treat and remove from the environment. The increased oxygen uptake in these materials can easily be detected in the change in the SARA fractions (DAD and FD), the associations by SEC, and an increase in carbonyl and sulfoxide functions somewhat similar to aged asphalt binders.

While much of the written description focuses on methods, the inventive technology also includes apparatus, e.g., including but not limited to those shown, perhaps schematically, in the figures. Four Examples Of Analysis Of Hydrocarbon Chemical Compositions That Can Be Determined Using SAR-AD Second Generation:

Four novel approaches for SAR-AD Second Generation are described below.

1. SAR-AD+DAD (Diode Array Detection, also known as Photo Diode Array PDA)

U.S. Pat. No. 9,353,317, generally disclosing technology that may be referred to herein as SAR-AD, makes specific mention of analysis componentry of well-known detectors such as ELSD (evaporative light scattering detector), optical absorbance (which include UV and visible), refractive index, CAD (charged aerosol detector), and other spectrometers.

The type of optical absorbance detector conventionally used in the patented SAR-AD separation is the variable-wavelength detector (VWD). Briefly, the basis of detection for VWD with SAR-AD is that a wavelength between 190 and 600 nm from a single lamp source is selected as a single, fixed wavelength absorbance detector for the entire analysis timeframe. The wavelength commonly accepted as providing the most overall useful information is 500 nm. The resulting profile trace is displayed as absorbance units (y-axis) vs time (x-axis) using absorbance at 500 nm as the basis for detection of any and all compounds present in the separation that absorb visible light at 500 nm.

The new approach shown in this patent application to add significant detection capability is a Diode Array Detector (DAD). Briefly, light from two separate lamps ranging from 190 nm to 950 nm is dispersed by a holographic grating to a diode array arrangement. This allows simultaneous access to all wavelengths and is not confined to a single or fixed wavelength. The wavelengths span UV, Visible, and near-infrared regions of the electromagnetic spectrum. The near-infrared (NIR) spectral region lies approximately at 780 nm and higher, therefore a DAD extends beyond the UV-Visible range (190 nm-780 nm). Unlike VWD, the resulting DAD detection profile is a two-dimensional plot of absorbance units (y-axis) vs. a range of wavelengths (x-axis) for all timeframes, throughout the entire separation. Alternately, and very unlike VWD, the resulting detection profile is also constructed as a three dimensional plot of absorbance units, wavelength, and time: each situated on the three axes of a three dimensional depiction.

The ability of a DAD to detect and identify key compounds separated by SAR-AD is magnified by the SAR-AD separation. SAR-AD separates a whole sample of asphalt, heavy oil, vacuum or atmospheric residuum, petroleum, fossil-source or other sample into discrete fractions based on their chemistries. Whereas it is unlikely that a DAD spectrum that is recorded for a whole petroleum-based sample with the broad and numerous chemical complexities of all compounds present in asphalt binder can be used to identify a key analyte (the signal would be obscured by interferences), the DAD spectra from a SAR-AD fraction has the advantage that the separation serves to concentrate key analyte(s) within a fraction. Having therefore increased the sensitivity and eliminating many interferences, the coupling of SAR-AD with DAD can be used as a novel identification and measurement tool.

The Federal Highway Administration (FHWA) and the national Asphalt Pavement Association report that asphalt is the most commonly recycled product in the United States. Recycled asphalt pavement is commonly called RAP, while recycled asphalt shingles from roofs is commonly called RAS. RAP and RAS recovered from years of use in the field are known to contain asphalt that has undergone significant aging. By use of the term aging, it is understood that the aging is by oxidation (hence the more descriptive term oxidative aging). Highly oxidatively-aged RAP and RAS contains asphalt that is generally harder and more brittle than it's unaged, unoxidized, virgin counterpart(s).

The effect of blending RAP and RAS into virgin asphalt for recycling and reuse for new paving and roofing products therefore often has the outcome of stiffening the overall blend. Identification and measurement of the amounts of RAP and RAS in a reblended asphalt matrix, however, is problematic if not impossible. Although it is well-known that an effect of oxidative aging is often a significant increase in the amounts of asphaltenes, conventional investigative techniques and SARA separations indeed do find higher amounts of asphaltenes, but the oxidized and less-oxidized asphaltenes are difficult to distinguish. In addition, the asphalt market is abundant with softeners, rejuvenators, additives, and modifiers which when added to the reblended product, is reported to have a softening, rejuvenating, or possibly restorative effect on the overall performance.

Figure 7:
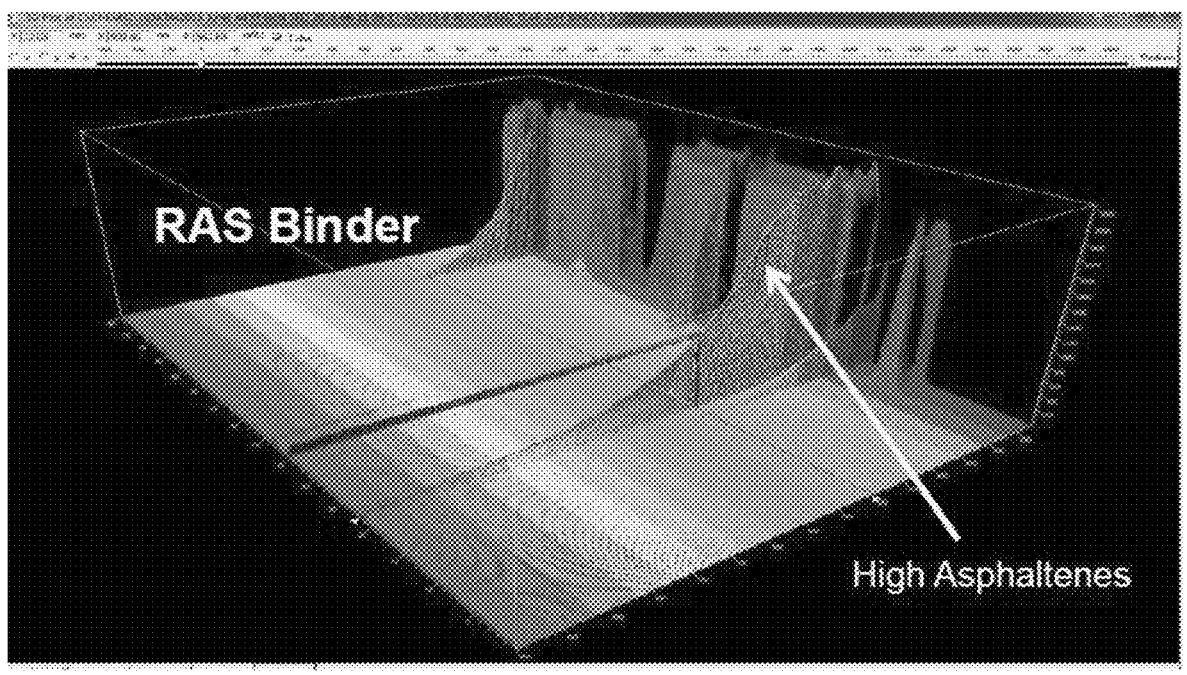
FIG. 7 depicts RAS Binder, High Asphaltenes.

Analysis performed with RAP and RAS products using the new SAR-AD+DAD technique shows that evaluation, characterization, and measurement of RAP, RAS, and reblended matrices is greatly improved over original SAR-AD analysis. FIG. 7 shows a three dimensional plot of the SAR-AD results of a RAS asphalt analyzed using SAR-AD+DAD. FIG. 7 shows runtime on the axis running from the lower middle of the plot towards the left. Wavelength is displayed on the axis running from the lower middle of the plot towards the right. The third axis running from the middle right hand side to the upper right hand side is absorbance. As opposed to conventional analysis that would simply report higher asphaltenes, the presence of oxidatively-aged asphaltenes is observed by DAD as a multiplet that gradually and broadly tails from low wavelengths to high wavelengths. This level of characterization and detail would not be available from a VWD detector.

Figure 8:
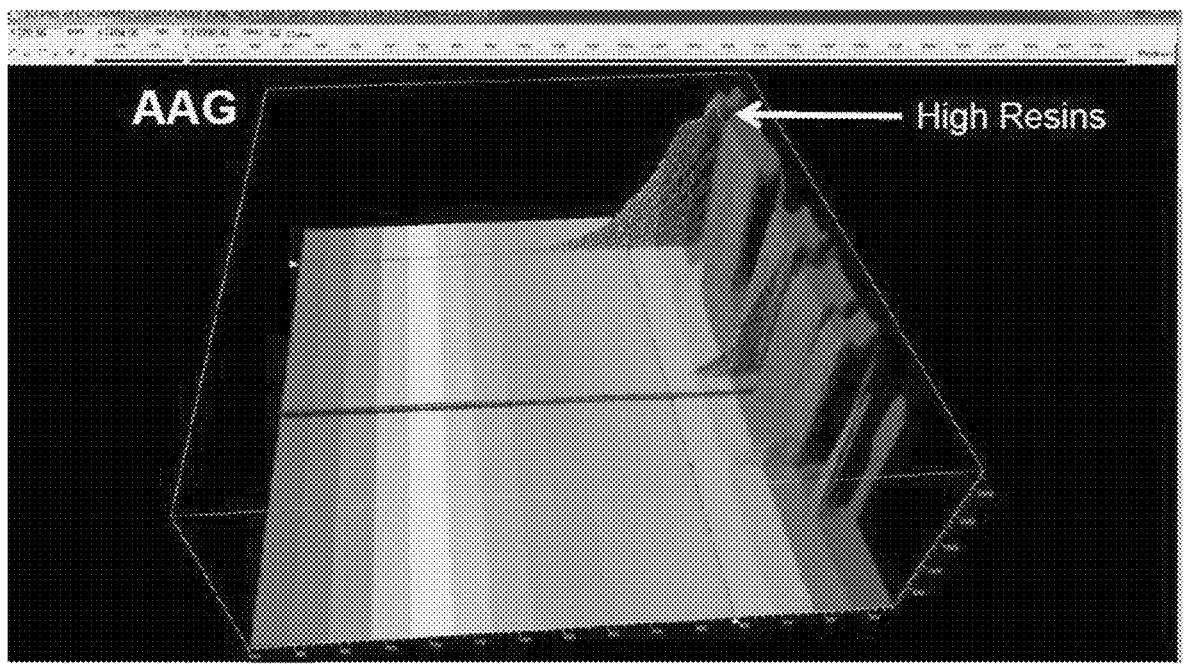
FIG. 8 depicts AAG, High Resins.

An example of an asphalt demonstrating complementary chemical features of the RAS asphalt binder is shown in FIG. 8. This particular SAR-AD+DAD separation is for SHRP (Strategic Highway Research Program) Asphalt AAG, which is a California Valley source. This asphalt is known to contain a relatively low amount of asphaltenes (as opposed to the RAS asphalt shown in FIG. 7). FIG. 8 is turned in a slight clockwise direction, however the axes remain oriented as described for FIG. 7. Not only are the asphaltenes much less observed, but the SAR-AD fraction known as the resins are revealed as the dominating feature of the DAD spectra. Thus it is seen that the DAD can be used as a type of fingerprinting for identification of an asphalt's source.

Figure 9:
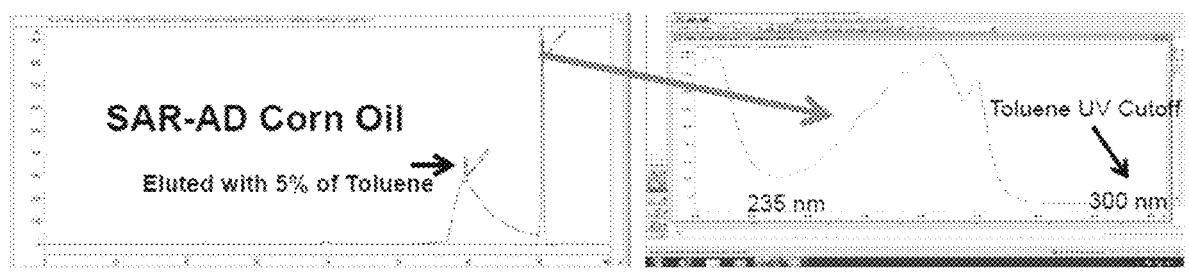
FIG. 9 depicts SAR-AD Corn Oil eluted with 5% of Toluene, Toluene UV cutoff.

It has been noted previously that rejuvenators may be used to soften or restore aged asphalt physical performance characteristics, and bio-based modifiers from agricultural sources have been successfully blended with RAP and evaluated as rejuvenating agents. To demonstrate the utility of the DAD to identify a bio-based product, FIG. 9 shows a SAR-AD+DAD separation of the elution region around the resins fraction. The left side of FIG. 9 shows the profile for the ELSD, which reveals a light-scattering intensity response, but no chemical information about the eluate. The right hand side however is a DAD two-dimensional plot of absorbance vs. the diode-array derived wavelength range showing that the UV-Visible scan can be used to identify this compound as corn oil.

Figure 10:
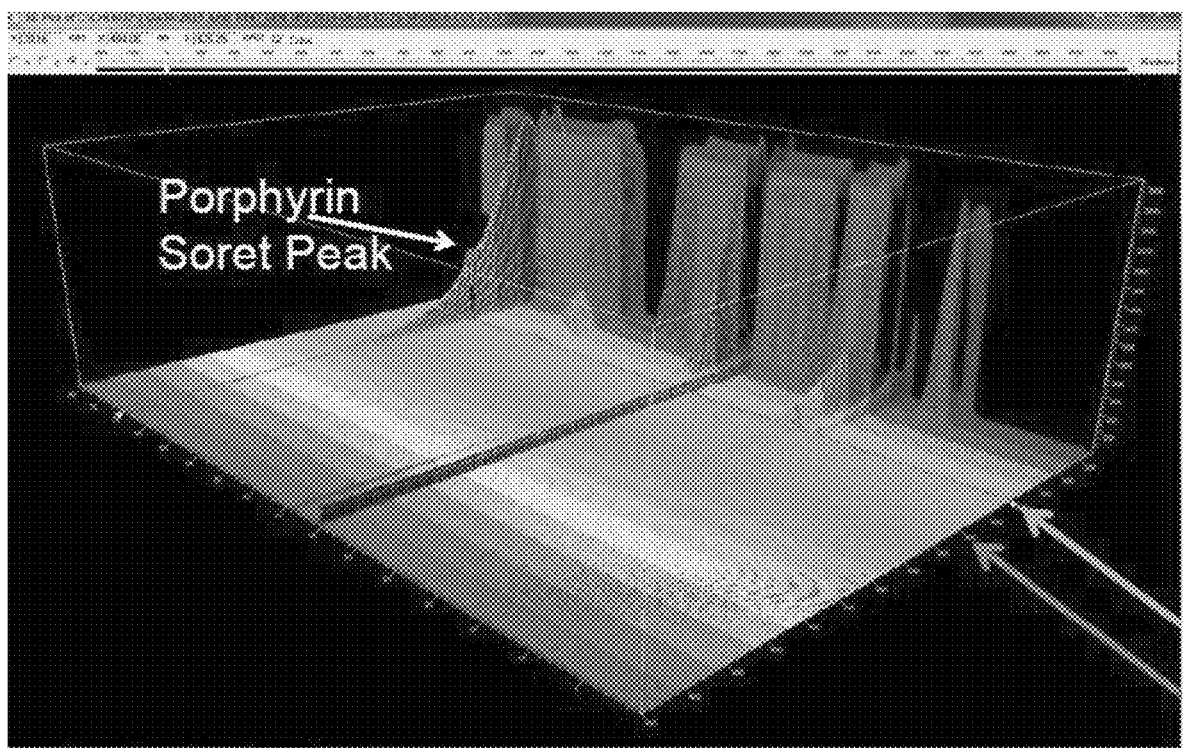
FIG. 10 depicts Porphyrin Soret Peak.

Another example of the usefulness of chemical identification and fingerprinting that can be exploited through use of the SAR-AD+DAD is shown in FIG. 10. This particular asphalt is known to contain compounds known as porphyrins at a relatively significant concentration. The porphyrins are evident in the resins fraction using the DAD. Porphyrins are identifiable by a spectral feature called the Soret absorbance peak at 410 nm (upper arrow of the pair). For purposes of this explanation, the two arrows in FIG. 10. can be used to trace two signals demonstrating what a conventional single, fixed wavelength profile would look like using the typically-used VWD detector rather than the DAD. The lower arrow points to the 500 nm wavelength that is used in the patented SAR-AD separation. A trace from left to right along the 500 nm line indicates that the porphyrin would not be detected using the conventional SAR-AD technique using VWD.

Figure 11:
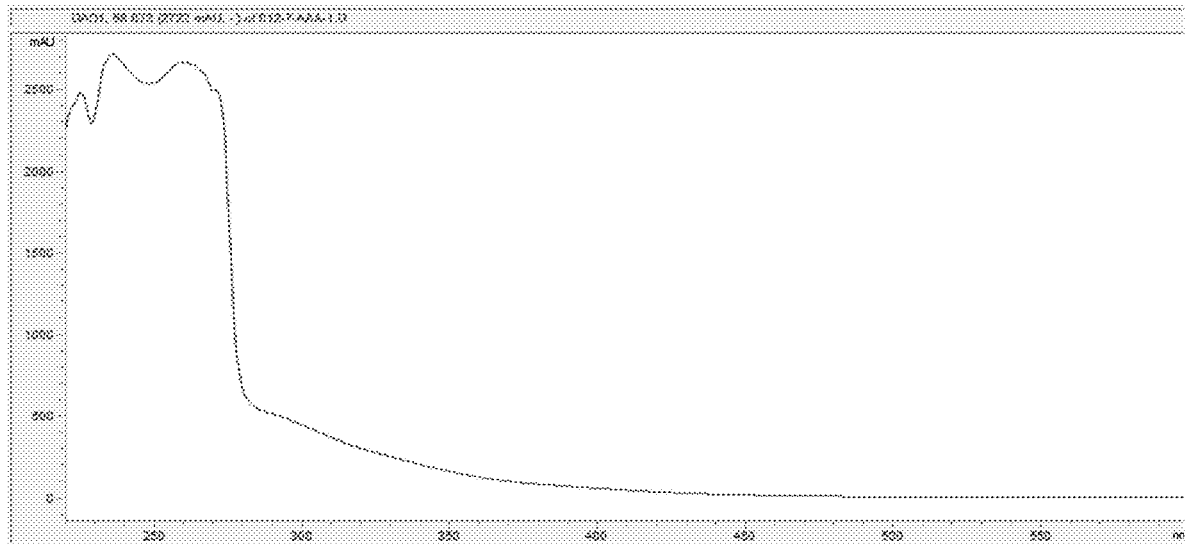
FIG. 11 depicts a two-dimensional plot of absorbance v. wavelength for a relatively simple mix of aromatic compounds in an aromatics fraction.
Figure 12:
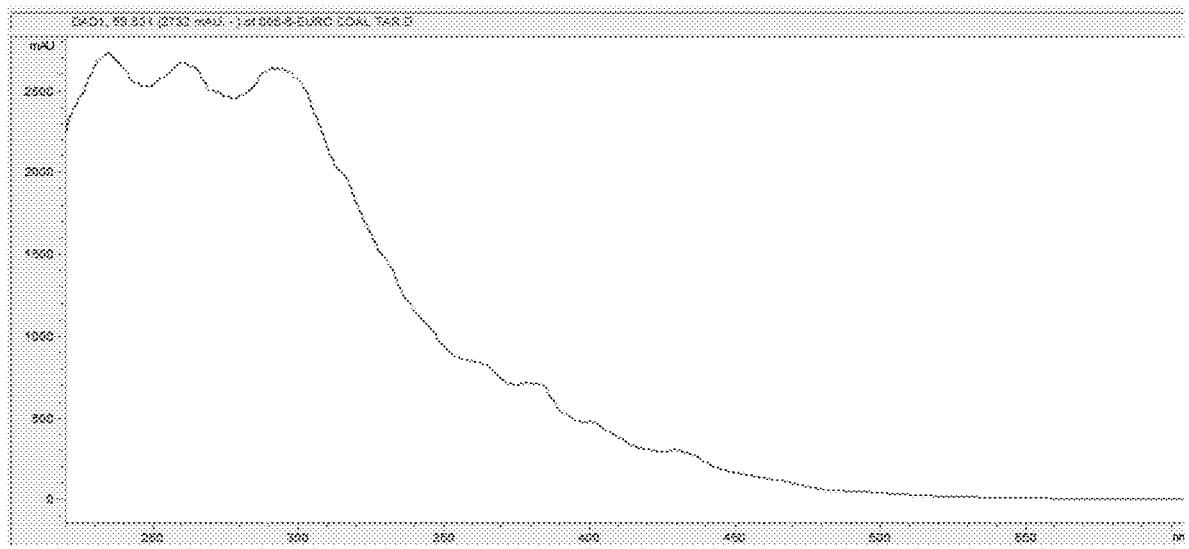
FIG. 12 depicts a two-dimensional plot of absorbance v. wavelength for a complex mixture of aromatics compounds in an aromatics fraction.

A final example of the utility of the DAD used in conjunction with the SAR-AD separation is provided in FIGS. 11 and 12 to show how finely it can be used to show differences in aromatics contents. FIG. 11 shows a two-dimensional plot of absorbance vs. wavelength for the aromatics fraction eluted by 95% heptane/5% toluene in reverse flow from the non-porous, high surface energy adsorptive stationary phase column (e.g., glass bead column), and additional weakly adsorbing stationary phase column (e.g., amino propyl silica, e.g., aminopropyl-functionalized silica gel column) after, e.g., an inert stationary phase column of the SAR-AD for SHRP asphalt AAA. Note that in certain SAR-AD embodiments, the first column after the inert stationary phase column may be glass beads and the next column may be amino propyl silica (APS). Further, in forward flow, elution proceeds from the head of the glass bead columns to the tail of the APS column (still, regardless of which direction flow occurs, an eluate is still generated). FIG. 12 shows identical separation conditions for a coal tar derived type of asphalt material. The complexity of the spectra especially towards higher wavelengths in the coal-tar derived material are due to the many chemically-complex aromatic ring species present. The relative simplicity of the spectra of the more conventional asphalt sample AAA stands in stark contrast to the complexity of the asphalt derived from a fossil source that is not strictly petroleum-based. This insight is not available from single, fixed-wavelength detection.

The real usefulness of the DAD can only be realized after the sample has been first separated using the SAR-AD scheme. Otherwise, detection for examples like those presented above is difficult or not possible for an unfractionated sample, because competing interferences from co-existing compounds and co-existing chemical species interferences would prevent detection that is observed when an analyte is observed in relative isolation like that produced by SAR-AD fractionation.

2. SAR-AD+FD (Fluorescence Detection)

Figure 13:
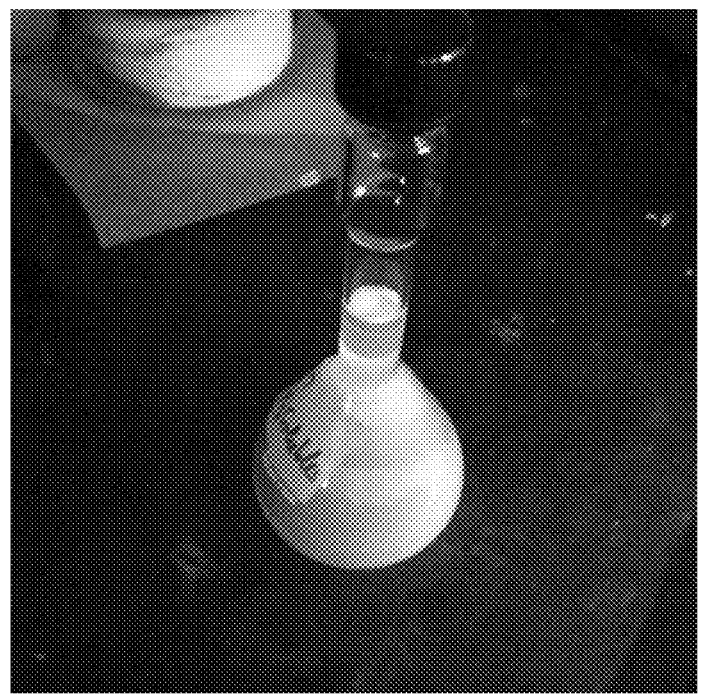
FIG. 13 depicts Visible Fluorescence Exhibited by CyC6-soluble Asphaltenes.

It is well known and reported in the literature that there are indigenous compounds in petroleum products, petroleum crude oil, asphalt, bitumen, heavy oil, etc. that fluoresce. Fluorescence most typically refers to excitation of light in the UV region with release of light at a greater wavelength in the visible region that is observed with the human eye. For example, FIG. 13 shows a photo of the SAR-AD cyclohexane-soluble portion of asphaltenes illuminated by a UV (black) light using a UV wavelength of 350 nm. The photo shows that the cyclohexane-soluble portion of the asphaltenes emits a visible yellow-green color fluorescence (at approximately 565 nm—visible in the photo as the bright white color in the volumetric flask).

Fluorescence is highly sensitive to the chromophore/fluorophore nature of materials within crude oils, bitumen, coal liquids, asphaltenes and other natural or refined hydrocarbon sources. Some limitations occur for heavier aromatic or highly polar species due to intermolecular quenching, which can be overcome by dilution, and/or by intramolecular effects due to the presence of various functional groups. In its most basic form, the wavelength at the maximum of the emission spectra can be used to correlate with the number of fused aromatic rings. This simple analysis can be used to differentiate between different crude oils, different crude oil fractions, different crude oil properties, processing conditions, oil spill identification and the presence of additives.

General trends in the number of fused aromatic cores increasing from 1 ring aromatics to 5 ring aromatics show an increasing red-shift in the emission maximum: benzene (280 nm), naphthalene (320 nm), anthracene (390 nm), tetracene (485 nm) and pentacene (590 nm). (Groenzin and Mullins, Molecular Size and Structure of Asphaltenes from Various Sources 2000) Although there are to be some expected variances in the maximum of emission values depending upon the geometry of the fused rings and number and type of heteroatoms these ranges are good predictor of average aromatic size. This can also be a diagnostic for various oil types or refining products. For instance a gas condensate contains two fluorescence maximums corresponding to one ring aromatics (290 nm) and two ring aromatics (325 nm). (Mullins 1999) At the other extreme of petroleum are the asphaltenes which generally have no emission in the region of 1 or 2 ring aromatics with a small amount of emission occurring for 3 ring aromatics (370 nm) with most asphaltenes having a maximum of emission around 450-550 nm. For non-heteroatom containing aromatic species this range corresponds to 7-11 rings. (Mullins 1999) Addition of heteroatoms of aromatic species tends to shift the emission maximum to the red. (Abou-Hatab, Spata and Matsika 2017)

Figure 14:
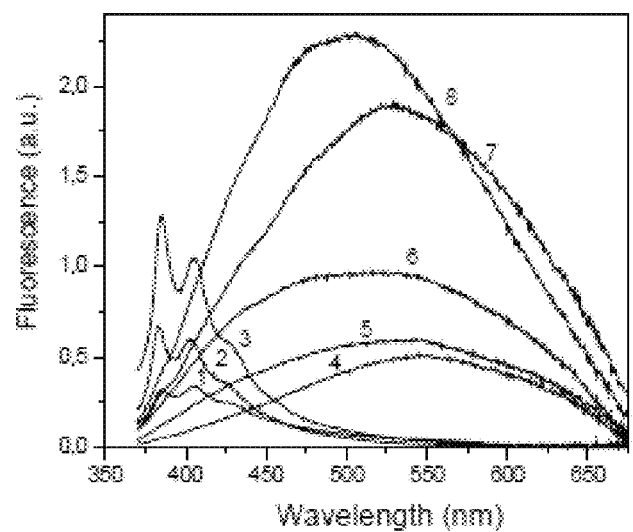
FIG. 14 shows a graph representing Fluorescence emission spectra of some oils and oil products excited at 355 nm. 1—Motor oil, 2—Shell Diala oil, 3—oil SAE 30, 4—Bunker Fuel oil, 5—Arabian medium crude oil, 6—Basra crude oil, 7—German crude oil, 8—Nihian crude oil. Figure taken from Karpicz, 2005.

Utilizing the trends in the emission can allow for distinction between different refining materials and different crude oils as shown in FIG. 14.

Figure 15:
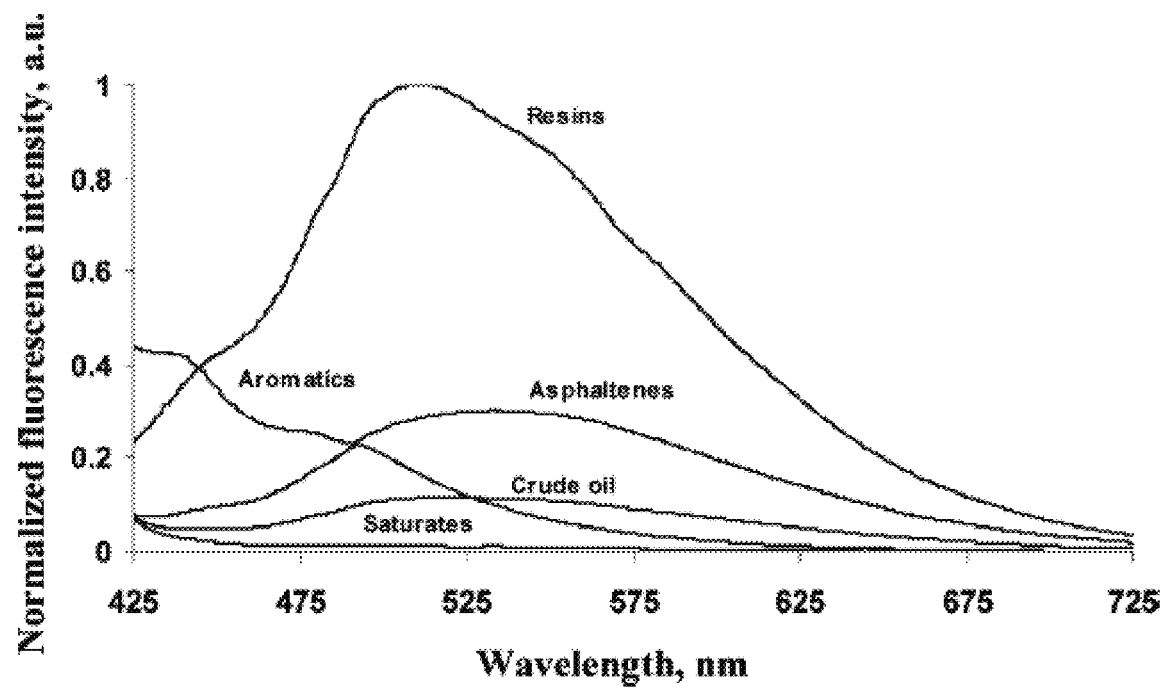
FIG. 15 shows a graph representing Fluorescence spectra of Hamaca crude oil and its SARA fractions. Figure taken from Riveros, et al, 2006.

Significantly more data can be obtained from fluorescence spectra by fractionation of crude oils by SARA methods which helps to understand the aromatic size of the different crude oil fractions as shown in FIG. 15. Several other publications show a significant difference between diagnosing the resins content or differences between resins or deasphalted oils, which are significantly blue-shifted relative to asphaltenes.

Several works have also shown that the fluorescence spectra, and emission maximum, of asphaltenes can distinguish between smaller coal tar asphaltenes and petroleum asphaltenes and differences between asphaltenes from various crude oils sources. (Groenzin and Mullins, Molecular Size and Structure of Asphaltenes from Various Sources 2000) Fluorescence spectroscopy can also be used to differentiate between various severities of thermal treatment during hydrotreating (Vo-Dinh 1978). As thermal treatment increases, the size of the asphaltenes becomes smaller due to cleavage of aliphatic side chains and other carbon-carbon bonds. This reduction in size with thermal treatment results in asphaltenes that become more blue-shifted. (Buch, et al. 2003)

Of particular interest to the use of fluorescence detection in conjunction SAR-AD is evidence that fluorescence methods can be used to differentiate between asphaltenes of different solubility classes. By precipitating asphaltenes using different pentane to toluene ratios and analyzing the sample by fluorescence, it has been shown that less soluble asphaltenes become more red-shifted, and correlations with other methods showed that this was due to larger fused aromatic ring systems. (Groenzin, Mullins and Eser, et al. 2003) Other solvents such as acetone have distinguished different solubility and size classes of asphaltenes by fluorescence emission spectroscopy. (Buch, et al. 2003)

Figure 21:
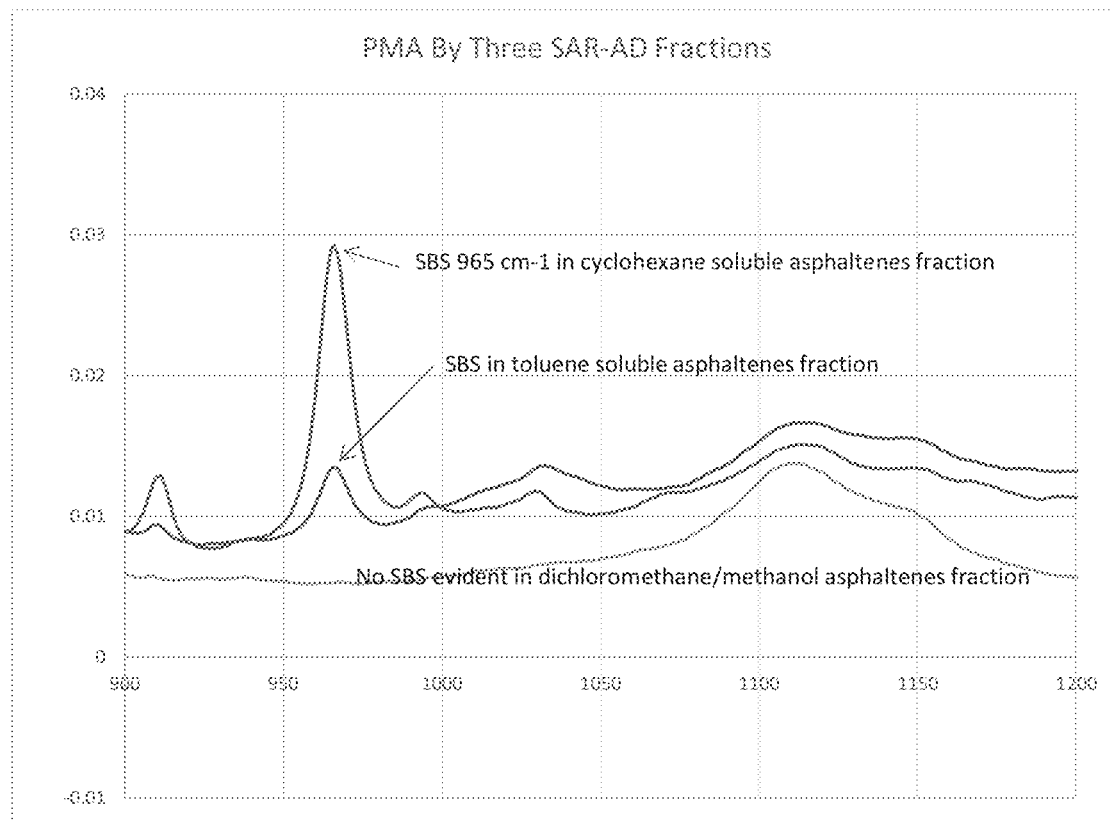
FIG. 21 shows a graph representing SBS in PMA by SAR-AD Fractionation with FTIR Detection.

By collecting fluorescence data in synchronous mode, a clear shift in the synchronous spectra to red is clear with higher apparent molecular weight fractions. (Al-Muhareb, et al. 2007) Similar results have been obtained from coal tars showing a linear correlation between the molecular weights for the SEC fractions and the peak maximum of the emission spectra (FIG. 21). (M. Zander 1990) (FIGS. 16A and 16B). Synchronous mode can also be used to show the distribution of the sizes of aromatic cores from different asphaltenes sources and can distinguish between one ring (260-300 nm), two ring (300-330), three ring (340-400), four ring (380-500), five ring (480-560 nm) and six ring (500-600 nm). (Scotti and Montanan 1998)

Other applications for fluorescence spectroscopy of crude oils can be achieved by comparing ratios of intensities at different wavelengths. For instance intensities of various emission wavelengths ((I(650)/I(450), I(650)/I(500), and I650/Imax)) have been shown to correlate with API gravity of oils. (Ryder 2002) This way of dealing with the data has been extended to calculate the density, cetane number, pour point, cloud point, aniline point, aromaticity and octane number from crude oils as published patent WO 2016/111956. (Al-hajji and Koseoglu 2016) Others have patented mapping of crude oils and crude oil components. (Alfano and Liu 1997) (Reyes and Pyeatt 1995)

Figure 17:
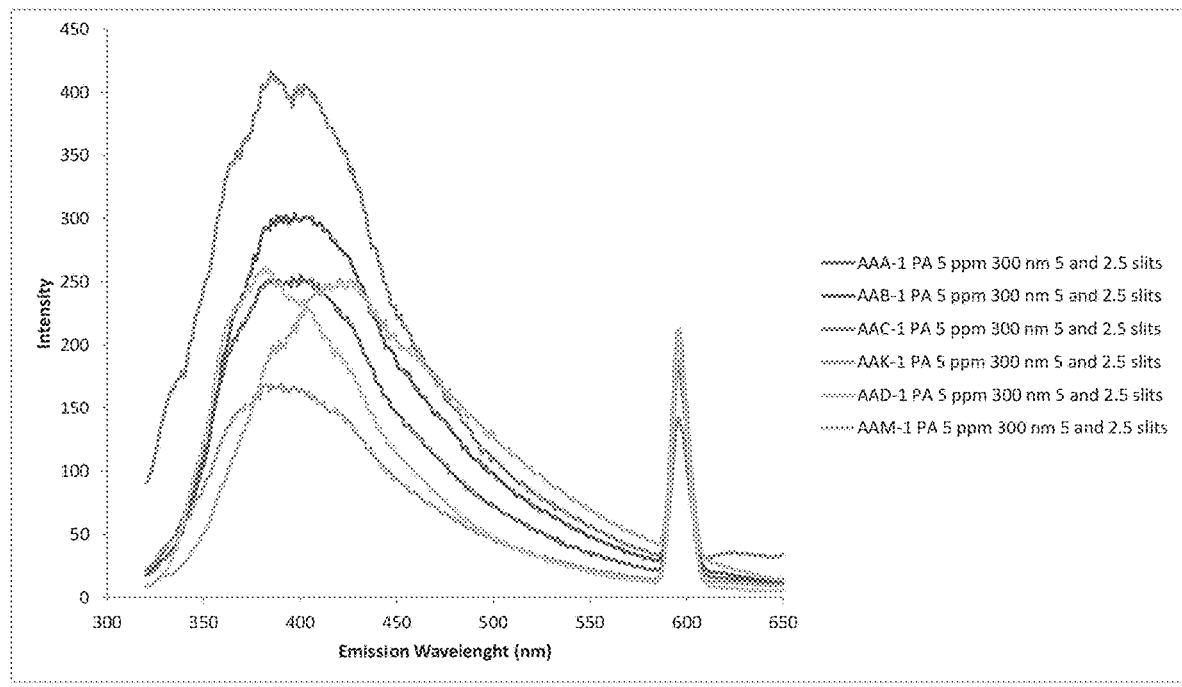
FIG. 17 shows a graph representing Fluorescence Data for a Resins Fraction for Six SHRP asphalt samples.
Figure 18:
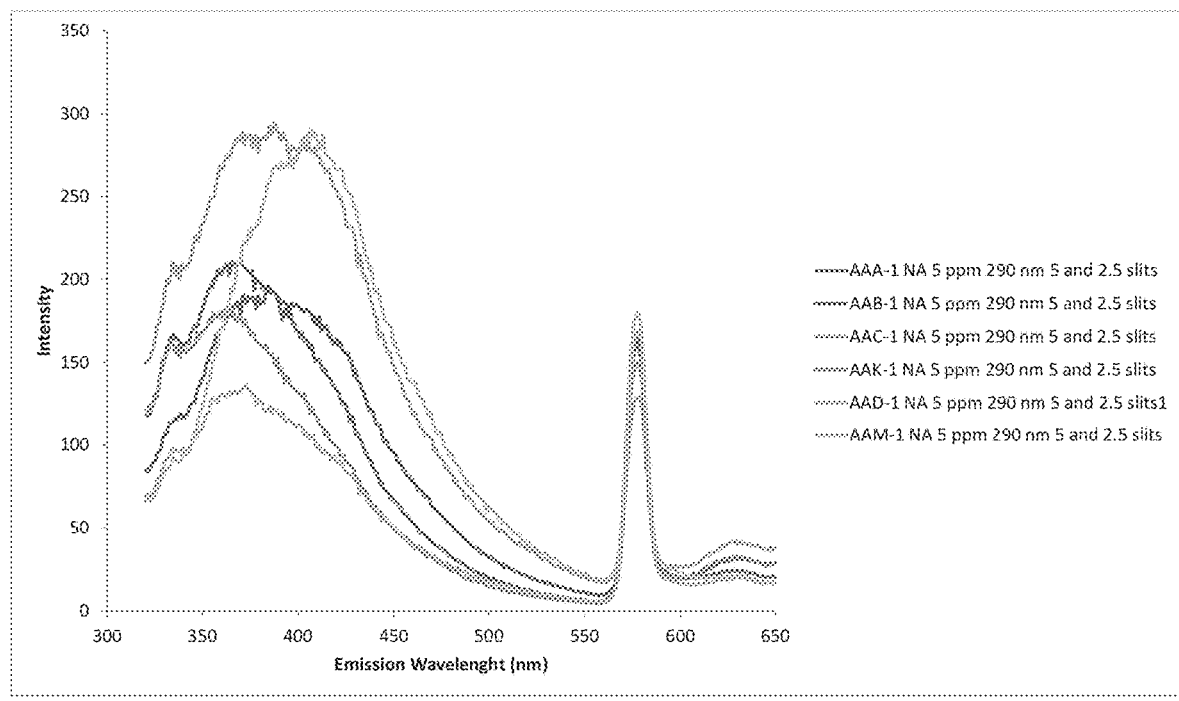
FIG. 18 shows a graph representing Fluorescence Data for an Aromatics Fraction for Six SHRP asphalt samples.

Finger printing of crude oils with SARA analysis is discussed in (Reyes and Pyeatt, Interpretation of Fluorescnece Fingerprints of Crude Oils and Other Hydrocarbon Mixtures Using Neural Networks 1995). SARA analysis and fluorescence is addressed in (Indo, et al. 2008), Data and results generated at the Western Research Institute to support the novel SAR-AD+FD technique are provided in FIGS. 17 and 18. The data were obtained for a series of six Strategic Highway Research Program (SHRP) asphalt samples from a wide variety of geologic sources. SHRP AAA is Lloydminster, SHRP AAB is Wyoming Sour, AAC is Redwater, AAD is California Coastal, AAK is Boscan, and AAM is West Texas Intermediate. The ability to—capture fluorescence spectra as a novel detection in conjunction with existing SAR-AD technology has clear merits for identification, fingerprinting, and chemical characterization applications. The advantage to using a spectral-based fluorescence spectroscopy detector is that spectral scans of various excitation and emission wavelengths including synchronous fluorescence may be generated and studied to reveal meaningful chemical insights into not only the asphalt or petroleum-based products, but also chemicals including but not limited to additives, polymers, and recycled products including but not limited to recycled asphalt pavement (RAP), recycled asphalt shingles (RAS), refined engine oil bottoms (REOB), rejuvenators, softeners, and bio-based oils.

3. SAR-AD+SEC

The microstructure and colloidal models of asphalt structuring have gained general acceptance in recent years due to a preponderance of data (Lesueur 2009, Le Guern 2010). Size exclusion chromatography separations (SEC) performed at WRI that separated asphalt into one fraction of associated components and a second fraction of non-associating components were among early evidence supporting these models (Branthaver et al. 1993). Several permutations of SEC separations of asphalt involving a variety of separation conditions exist in the literature (Altgelt and Hirsch 1970; Haley 1975; Brule 1983, Pribanic 1989, Jennings 1992, Kim 1993; Bishara and McReynolds 1992; Schabron et al. 2001; Wahhab et al. 1999), including methods for quantification of polymer and monitoring polymer degradation with oxidative aging (McCann et al. 2008, Dreessen et al. 2010). These methods either rely on the manual collection and weighing of the elution material at designated times or a detector, typically differential refractive index (RI), to correlate specific asphalt material with hydrodynamic volume and, consequently, molecular weight. The former method is typically used if further analysis of the material is needed. The latter type of separation, often referred to as analytical scale SEC, is more rapid for higher throughput and is generally more precise.

A major drawback in using an RI detector for quantification of asphalt molecular weights from SEC separations is that different types of molecules give different changes in RI for a particular solvent. For example, waxes within a binder show a negative change in RI, and more polar asphaltene type molecules give a very positive change in RI. Aromatics and weakly polar molecules are somewhere in the middle of this polarity spectrum and show a moderately positive change in RI. As an alternative, an evaporative light scattering (ELS) detector can be used that responds more uniformly across sample types (Carbognani, 1997).

The molecular weight of the unassociated non-polar fractions can have an important effect on asphalt viscosity (Redelius 2015). Traditionally, using a column/solvent strength combination to separate asphalt into a polar/associated fraction and nonpolar/unassociated fraction has been effective at obtaining the average molecular weight of the non-polar asphalt portion (Le Guern 2010). An alternative approach to the above separation, and proposed herein, is to separate the asphaltenes from the maltenes prior to running an SEC separation. This novel approach is proposed as an analytical-scale separation using a multidimensional column combination to provide more accurate information on the molecular weight of the unassociated species.

In U.S. Pat. No. 9,353,317, in at least one embodiment, a series of four columns is used with an initial starting configuration of inert PTFE (first), then glass beads (second), then aminopropyl-bonded silica gel (third), then activated silica gel (fourth). After injection of the sample into an n-heptane mobile phase, the asphaltenes precipitate onto the PTFE column, and the maltenes proceed with the mobile phase to the remaining columns, where a variety of solvents in forward and reverse flow cause adsorption and subsequent desorption of the saturates, aromatics, and resins fractions.

A novel improvement addressed in this patent application is the addition of a fifth column to provide measurement of the molecular weight of the maltenes (the heptane soluble compounds that elute from the PTFE column). A configuration that places a SEC (size exclusion chromatography column (such as a GPC column) at a point after the PTFE column is addressed in this application to measure the molecular weight or molecular size profiles of the maltenes.

Gel permeation chromatography separates the components of asphalt by molecular size or volume. In GPC, the large components elute from the column first, while the smaller components elute later. Conventional GPC of whole-sample asphalt, bitumen, and heavy oil samples that include asphaltenes has inherent problems due to the chemical tendencies of the asphaltenes to associate or agglomerate upon dilution as a function of solvent strength and sample concentration. False high molecular weights of asphaltenes are often reported due to chemical associations that are induced upon GPC analysis. The presence of the associated asphaltenes in the SEC profile adversely affects the ability of the chromatographic technique to accurately measure the molecular size or weight distributions of the sample.

Figure 25:
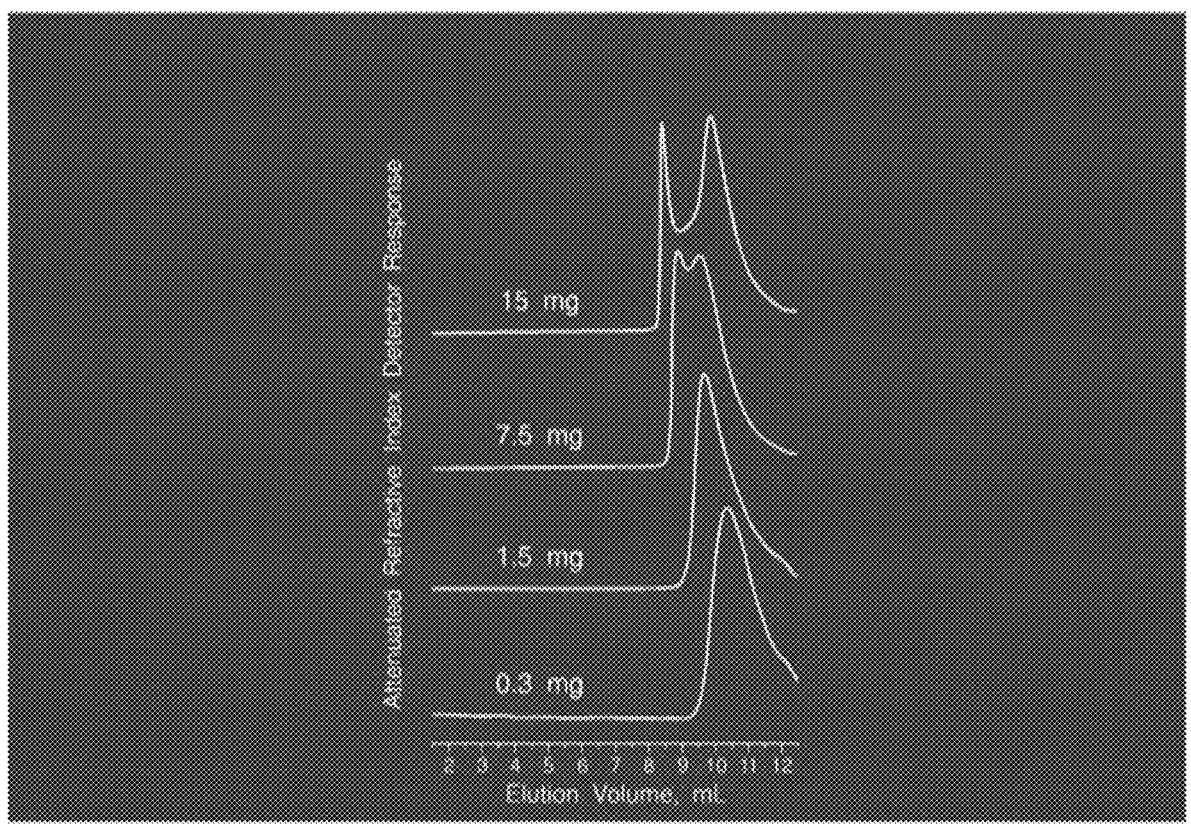
FIG. 25 shows a graph representing how different concentrations of the same asphaltenes injected using conventional SEC can change the molecular size profiles and results that are obtained.

Since the presence and intensity of associated asphaltene species are induced artifacts or effects of the SEC parameters and separation conditions itself, it does not always provide an accurate measurement of the molecular weight distribution of the whole sample. FIG. 25 shows four comparisons of the same sample of asphaltenes that were analyzed using conventional SEC separation. As the concentration of the asphaltenes sample is increased, greater amounts of associations are induced and displayed by the refractive index detector response. The increased associations are evident as apparent increased molecular weights or sizes (i.e., a shift to lower elution volumes). The resulting molecular weight distribution is forced higher and higher, in spite of the fact that the asphaltenes are in fact the same sample for each analysis condition. Because these effects are an induced artifact or result of the separation parameters itself, the resulting molecular size measurements are not dependable. It is shown that at highest concentrations, multiple molecular sizes are evident, which cause interference issues with obtaining a true molecular size measurement of the sample.

The present invention, in embodiments, overcomes the asphaltene association problem by first precipitating out the asphaltenes using the PTFE column. In this fashion, the maltenes without the asphaltenes may be directed by elution into a SEC (e.g., GPC) column with detection including, but not limited to, IR, FTIR, NIR, MWD, VWD, DAD/PDA, FD, RID, ELSD and intrinsic viscosity detection.

The molecular weight ranges of an asphalt or bitumen play a significant role in the physical behavior of asphalts at low through high temperatures, as well as high to low frequencies under application conditions. Therefore the ability to determine an asphalt's, heavy oil's, bitumen's, or blend's molecular weight ranges through an improvement of the SAR-AD would add significant applicability of the SAR-AD Second Generation to more fully characterize asphalt, troubleshoot problematic misbehaved asphalts, predict how an asphalt will perform in mixing operation with mineral aggregates in a plant, in asphalt mix laying and compaction during construction, and in the field under traffic or without traffic at a variety of temperatures, and investigate asphalt chemistries.

The ability to include GPC/SEC may prove to be an especially reliable technique to discern the presence of relatively lower molecular weight materials such as additives, re-refined engine oil bottoms (REOB), and bio-based additives and rejuvenators which can be added to offset or restore the softening properties of stiff, recycled asphalt materials. Some mostly-lower-molecular weight softeners, bio-additives, re-refined engine oil bottoms, rejuvenators might possibly be of sufficiently low molecular weight to prevent their detection using evaporative light scattering detection (ELSD). Therefore, having the lower molecular weight material detected as a measurable peak (that can be integrated electronically and compared to the asphalt portion) of a GPC separation would be an advancement in detection and measurement capability.

Examples of the distinct advantage of the improved PTFE column-produced maltenes SEC technique are provided below.

Figure 26:
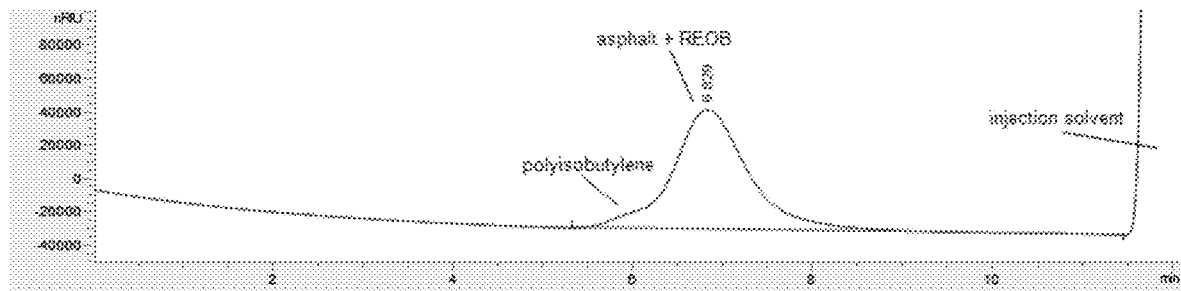
FIG. 26 shows a graph representing polyisobutylene, asphalt+REOB, and injection solvent.

FIG. 26 shows an SEC profile in which an asphalt sample containing an additive or modifier known as REOB (re-refined engine oil bottoms) was analyzed using a fifth column (an SEC column) at a point after the PTFE column as described above. In this example, the asphaltenes were first precipitated on the PTFE column, and therefore excluded from subsequent SEC analysis. The maltenes (the unprecipitated portion of the sample) were eluted with the mobile phase from the PTFE column, and directed to the SEC column (the fifth column of the separation scheme) as a novel multidimensional analytical scale separation. The resulting separation profile in FIG. 26 shows, in order of SEC elution, a relatively high molecular weight polyisobutylene component which is often found in REOB, followed by the asphalt peak, followed by the injection solvent peak. This example demonstrates that REOB (either intentionally or nonintentionally) added to an asphalt may be detected by the new technique using its polyisobutylene fingerprint identifier. It is doubtful that the separation results would be conclusive if associated asphaltenes were present in this analysis, because the associated asphaltenes would interfere with the detection of the polyisobutylene. Associated species are found in the molecular size region of polyisobutylene, thus preventing the identification and quantitation of polyisobutylene. The detector used in the FIG. 26 example is refractive index detection (RID). Evaporative light scattering detection provides results that are consistent with RID.

Figure 27:
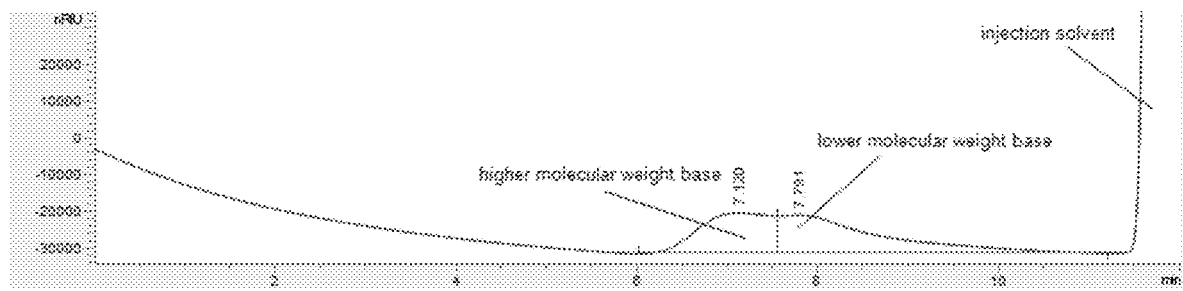
FIG. 27 shows a graph representing higher molecular weight base, lower molecular weight base, injection solvent.

FIG. 27 shows that the novel SEC technique in which asphaltenes are precipitated from the maltenes, and the maltenes are analyzed by SEC, can be used for assessing whether or not an asphalt sample is comprised of a blend. FIG. 27 shows the fifth-column SEC analysis of an asphalt sample that is comprised of a California Valley base asphalt that has a lower molecular weight and an Alaska North Slope base asphalt that has a higher molecular weight. A bimodal separation has been achieved. The detector used in this example is also the RID. ELSD provides results consistent with RID.

Figure 28:
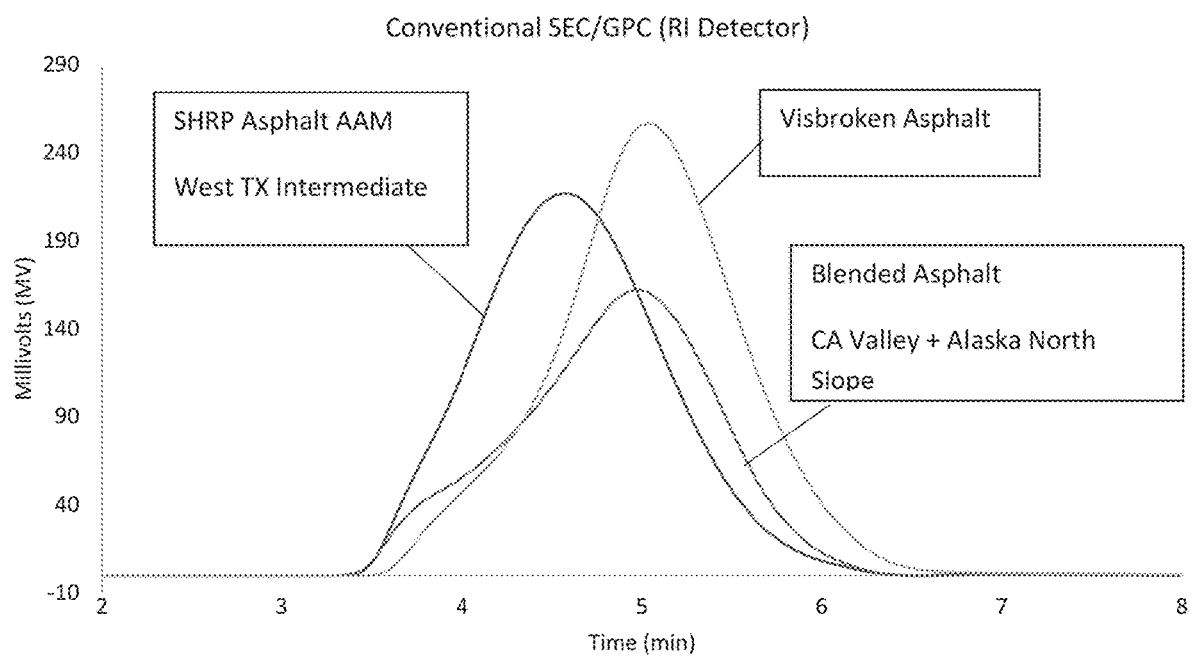
FIG. 28 shows a graph representing Conventional SEC/GPC (RI Detector), including SHRP Asphalt AAM, West Texas Intermediate, Visbroken Asphalt, Blended Asphalt, California Valley+Alaska North Slope

The advantage of the new multi-dimensional SEC technique is evident when a conventional SEC separation of this asphalt is performed without first precipitating the asphaltenes. FIG. 28 shows the same asphalt blend analyzed by SEC in which the asphaltenes have not been removed from the sample's SEC analysis. The association effects of the asphaltenes present in the separation can be misleading, leading an analyst to believe that the asphalt sample is a single binder showing asphaltenes associated at the higher molecular weight shoulder of an asphalt peak.

Figure 29:
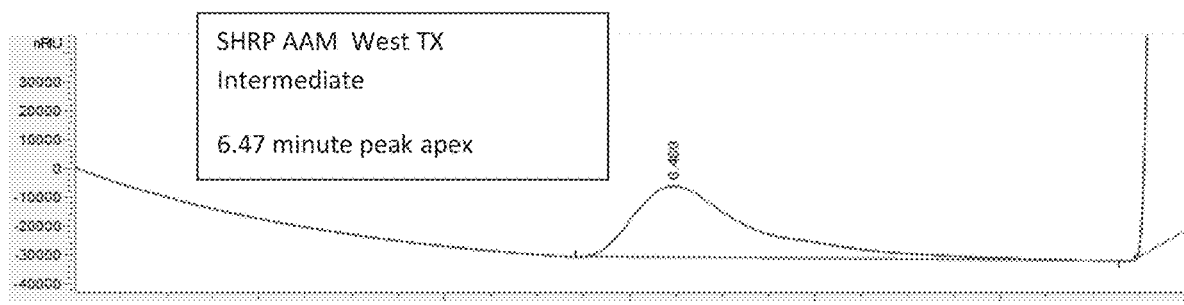
FIG. 29 shows a graph representing SHRP AAM (West Texas Intermediate or WTI), 6.47-minute peak apex.
Figure 30:
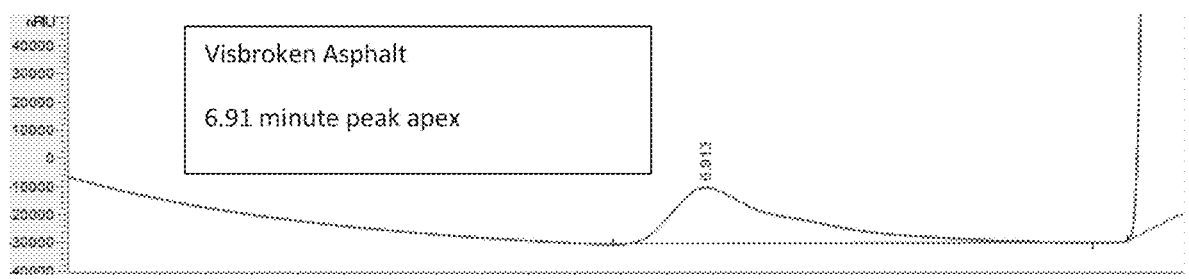
FIG. 30 shows a graph representing a Visbroken residue Asphalt, 6.91-minute peak apex.

FIGS. 29 and 30 are provided in this application to show that the novel SEC separation performed on de-asphaltened samples does not significantly change the performance of the resulting molecular weight measurement. FIG. 29 shows same SHRP (Strategic Highway Research Program) AAM West Texas Intermediate sample shown in FIG. 28, except the asphaltenes have been removed by the prior precipitation event. Additionally, FIG. 30 shows a de-asphaltened SEC analysis of the same visbroken sample shown in FIG. 28. In the whole-sample conventional SEC-RID analysis provide in FIG. 28 the higher molecular weight AAM asphalt elutes before the visbroken asphalt. This result is portrayed to show that the SEC of the maltenes without the asphaltenes does not have an unexpected conclusion (i.e., the higher molecular weight sample does in fact elute with a lower elution volume than the visbroken lower-molecular weight sample). Therefore, it is shown that precipitation of the asphaltenes from the portion analyzed by SEC does not adversely affect the performance of the SEC separation to provide suitable molecular weight results.

Figure 31:
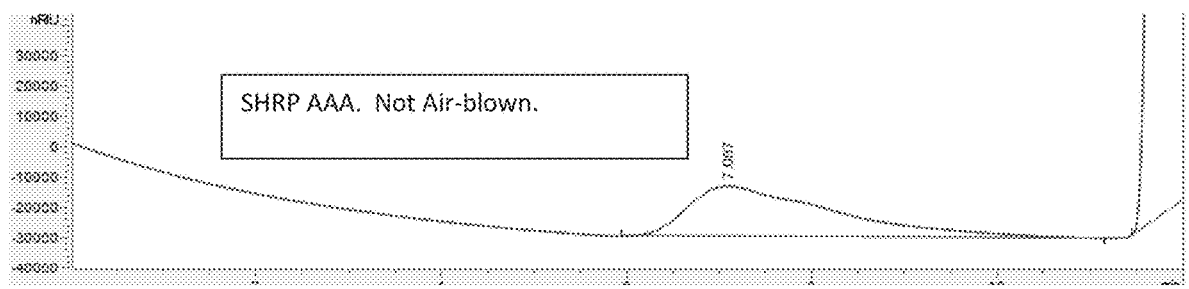
FIG. 31 shows a graph representing SHRP AAA, Not Air-blown.
Figure 32:
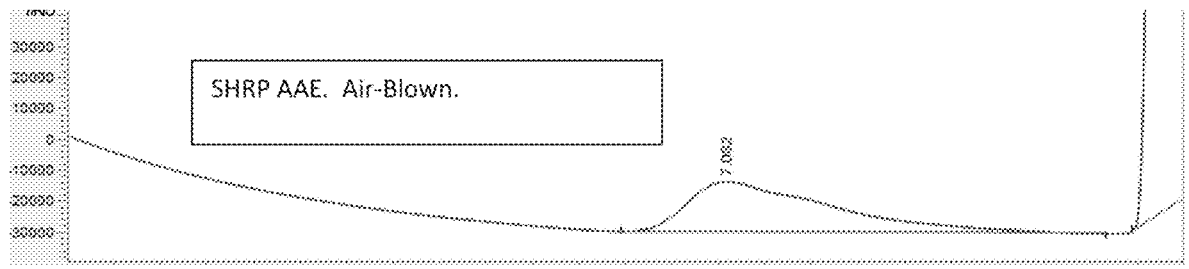
FIG. 32 shows a graph representing SHRP AAE, Air-blown.
Figure 33:
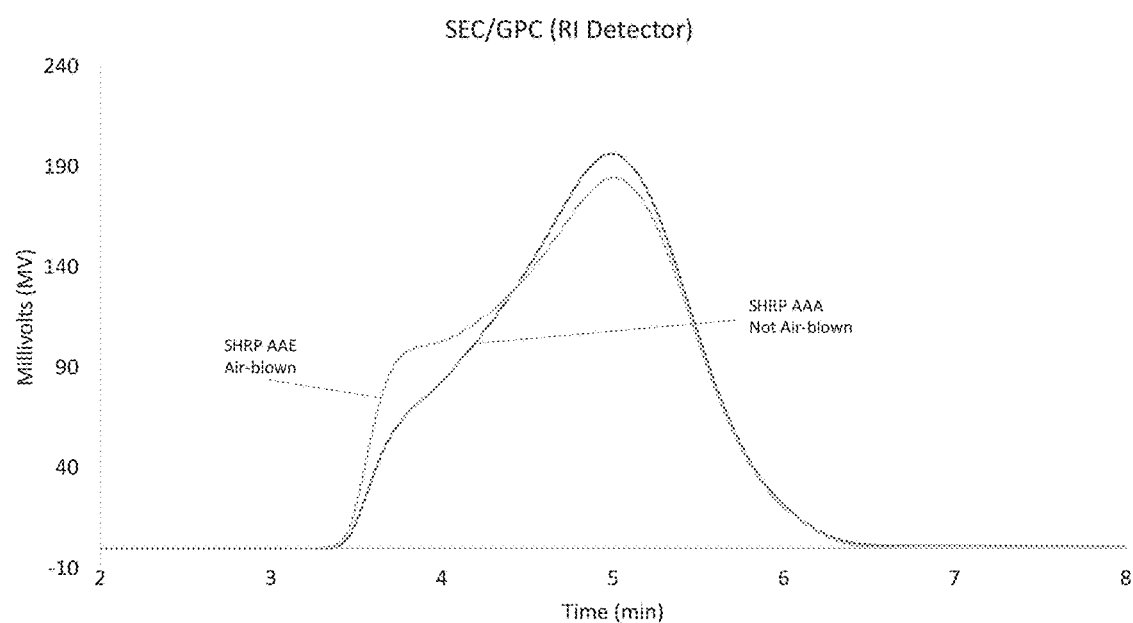
FIG. 33 shows a graph representing SEC/GPC (RI Detector), including SHRP AAE, air-blown and SHRP AAA, not air-blown.

The final example provided for the novel multidimensional precipitation+SEC technique shows the utility of the new separation scheme to be used in addition to (and not exclusive of) conventional SEC analysis of the whole sample. FIG. 31 shows a Canadian asphalt (SHRP AAA). FIG. 32 shows SHRP AAE which is an air-blown version of SHRP AAA. Although air-blowing an asphalt is known to increase asphaltene concentration, a comparison of the air-blown version to the one that has not been air-blown shows that the deasphaltened maltenes do not show any significant differences in their molecular weight profiles. FIG. 33 shows the same two asphalts—before and after air blowing—by conventional SEC and how very different the asphalte contents are. Analyzing samples by both the conventional and novel techniques can therefore be used to help elucidate whether an asphalt is air blown or simply a blend. Evidence is therefore provided that the novel deasphaltened maltenes SEC technique can be used not only as an alternative to conventional SEC, but also as a complementary technique.

4. SAR-AD+FTIR

Presently, most HPLC manufacturers do not commercially offer a Fourier-transform infrared (FTIR) detector unit for HPLC applications. Conventional thought is that most HPLC analytical applications are reversed-phase, and the relatively large amounts of water and other mobile phases in the eluent compared to the relatively small amounts of analyte greatly diminishes the usefulness of FTIR to measure molecular and vibrational spectra. For normal-phase separations, the overwhelming spectral contributions of the mobile-phase solvents will obscure detection of an analyte's functional groups in most instances.

SAR-AD is a technique using normal phase solvents to elute (on an analytical scale) relatively large amounts of fractions, each containing perhaps thousands of chemically-similar compounds. Therefore the utility of using FTIR as a detector for SAR-AD becomes a distinct option.

WRI is particularly skilled at using transmission-mode FTIR to measure precise molecular and vibrational spectra of asphalts, heavy oils, blends, polymer modified asphalts, petroleum products etc. particularly, but not limited to, quantities of additives, polymers, and the extent of oxidation that these products have undergone. Solvent choice in transmission mode is critical to the solvent not obscuring the wavenumber regions where these spectra exist for measurement purposes. Often, more than one solvent must be used so that a spectral region obscured by one solvent can be observed in a second solvent where that same region is free of solvent interferences. When it is taken into consideration that SAR-AD, in particular embodiments, employs four solvent mobile phases and that the instrument is capable of producing infinite blend ratios thereof, it becomes apparent that the pairing of SAR-AD with FTIR becomes an analytical option that can provide some limited, but very useful FTIR spectra. The fractionation as a result of the SAR-AD separation, in combination with on-the-fly FTIR Spectroscopy will greatly increase the amount of meaningful chemical information that can be obtained as a result of SAR-AD analysis.

Asphalt binders undergo oxidation with oxygen from air during aging which occurs at several stages, particularly in the hot mixing process with aggregates in the hot mix plant, during construction, laying and compaction, and in the long run during the pavement life. The oxidation reaction products are mainly oxygenated functions such as carbonyls and sulfoxides, and many others (Petersen). Other changes can occur as well in aromatics, whereas saturates or aliphatic structures are usually fairly stable (Petersen). They can all be easily tracked by infrared (IR) spectroscopy, following the absorbance of the characteristic bands for each of them, and using stable aliphatic structures as references. Some of the most characteristic bands include:

Aromatic structures centered around 1600 $cm^{-1}$

Aliphatic structures centered around various wavelengths, depending of their degree of branching: 1460 $cm^{-1}$, 1376 $cm^{-1}$, and 724 $cm^{-1}$, Oxygenated functions: carbonyl at 1700 $cm^{-1}$, and sulfoxide at 1030 $cm^{-1}$.

Figure 19:
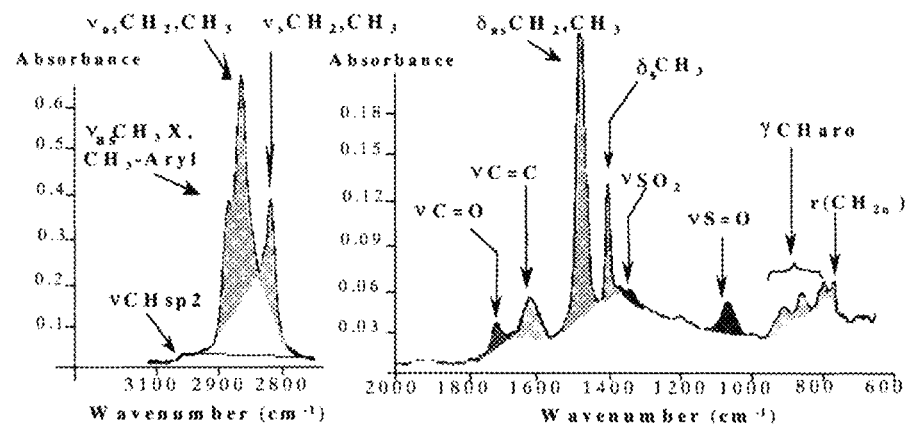
FIG. 19 shows graphs representing FTIR spectrum of a 4000-400 $cm^{-1}$ original bitumen.

FIG. 19 shows a description of the IR spectra for a base asphalt with the assignment of the main characteristic IR absorption bands (Lamontagne et al).

Polymer modification is a very common way to improve asphalt binder physical properties, and ultimately the performance of the pavement or the shingles or membranes, in the case of roofing applications. Several types of polymers can be used to make polymer modified asphalts (PMA's). The most common ones are the copolymers of styrene and butadiene (SBS), and the copolymers or terpolymers of ethylene with various co- or ter-monomers, such as but not limited to, vinyl acetate (VA), methyl acrylate, (MA), butyl acrylate (BA), and glycidyl methacrylate (GMA). This list is by no means limitative. Most polymers can be easily tracked in PMA's by using infrared spectroscopy, following their characteristic absorption bands, comparing the different IR spectra of the polymers with the base asphalt, and selecting their specific IR bands not interfering with the base asphalt. Here are some examples (Mouillet et al):

- SBS modified asphalt: out of plan bending vibration $\gamma CH$ of trans-butadiene 1-4 centered around 965 cm$^{-1}$ and styrene centered around 700 cm$^{-1}$ both from the SBS copolymer.
- EVA modified asphalt: stretching vibrations $\gamma C—O$ of vinyl acetate units centered around 1240 cm$^{-1}$ and $CH_2$ of ethylene units centered around 724 cm$^{-1}$ both from the EVA copolymer.

There are many additives that can be used to modify asphalts beside polymers such as acids like polyphosphoric acids or fatty acids, paraffins like Fisher Tropsch paraffins, fatty amines or amides, fatty esters, ethers, etc. Most additives feature functional groups that have characteristic absorption bands traceable by IR spectroscopy and sufficiently distinct from asphalt IR bands, and therefore allow the same IR characterization as above described for polymers.

In addition, PMA's and all additive modified asphalts also undergo oxidation at various stages of their application life, and the reactions occurring are similar in nature of the base asphalts, and therefore can also be followed by IR, meaning all above considerations on base asphalts are valid for PMA's and additive modified asphalts.

Examples are provided below to show the utility of SAR-AD+FTIR to characterize asphalt, diagnose problematic issues, track the extent of oxidative aging, and determine polymer or additive modifications to an asphalt or asphalt blend.

Figure 20:
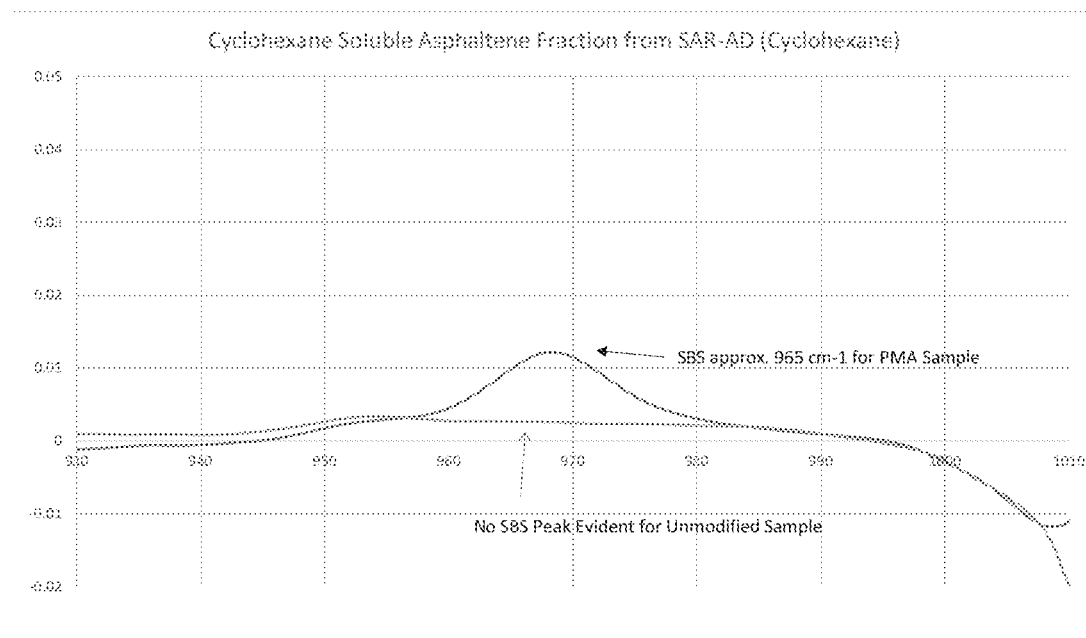
FIG. 20 shows a graph representing SBS in Modified and Unmodified Cyclohexane-Soluble Fraction by SAR-AD+ FTIR.

Work performed at WRI shows that when SBS (styrene-butadiene-styrene triblock copolymer)-modified asphalt is analyzed using WRI's SAR-AD (U.S. Pat. No. 9,353,317), the SBS component of the polymer-modified asphalt can be observed to significantly elute with the fraction defined as the cyclohexane-soluble portion of the n-heptane precipitated asphaltenes. Therefore, at least a significant portion of the SBS precipitates in n-heptane with the asphaltenes on the inert-stationary PTFE phase column, and is substantially redissolved with the mobile phase switch to cyclohexane, with elution of the SBS with the cyclohexane-soluble portion of the n-heptane precipitated asphaltenes. FIG. 20 shows the detection of SBS in the cyclohexane elution solvent using the characteristic absorption band at 965 cm$^{-1}$. FIG. 20 shows how an SBS polymer modified asphalt (PMA) can be distinguished from an unmodified asphalt using SAR-AD+FTIR. FIG. 21 shows another instance of SBS FTIR measurement with cyclohexane, but also shows that an additional amount of the precipitated SBS is subsequently eluted with toluene. The redissolution of the precipitated SBS is shown to be completed with toluene, as no additional SBS is apparent with the third redissolution solvent, which is dichloromethane/methanol.

Figure 22:
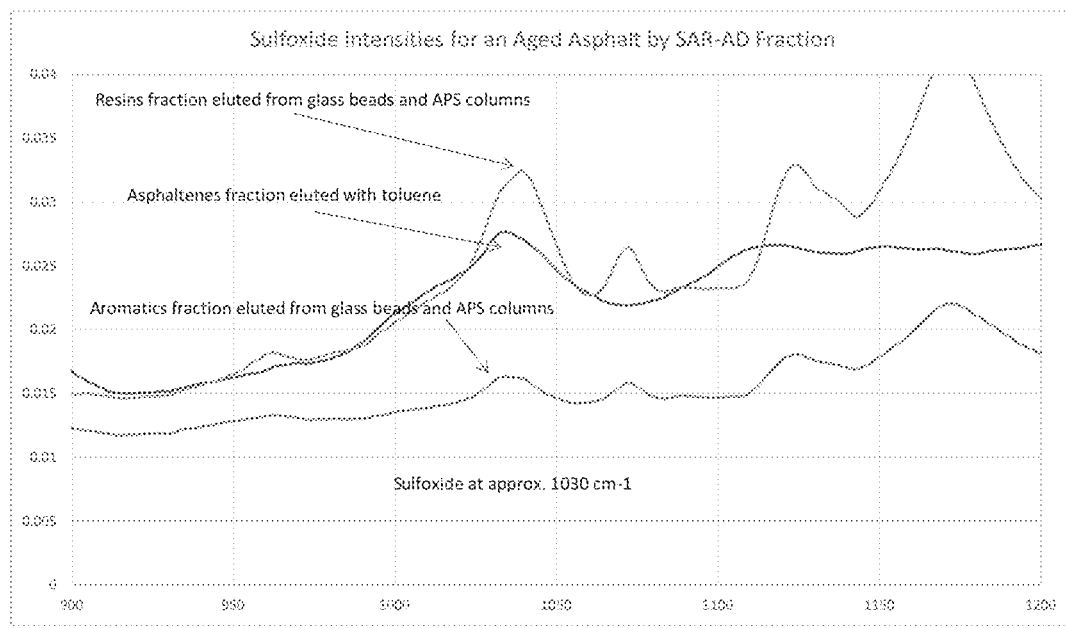
FIG. 22 shows a graph representing Sulfoxide Band Intensity of SAR-AD Fractions for an Aged Asphalt.

FIG. 22 shows the amounts of sulfoxide absorption by FTIR for three SAR-AD fractions for an aged asphalt sample. The relative and net amounts of sulfoxide present in each fraction may be a unique identifier for asphalt binders that may age differently depending on their chemistries. SAR-AD used in conjunction with FTIR detection may ultimately provide new evidence for the reaction mechanisms of oxidative aging.

Figure 23:
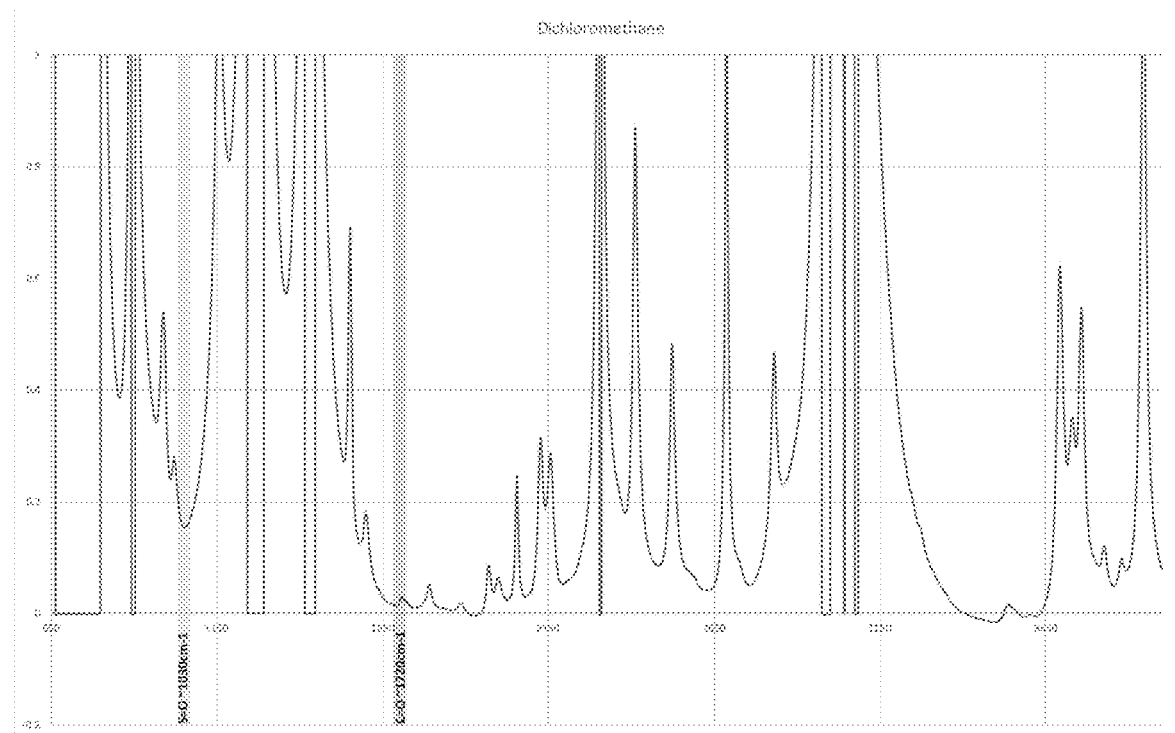
FIG. 23 shows a graph representing Utility of Dichloromethane for Carbonyl and Sulfoxide Bands.
Figure 24:
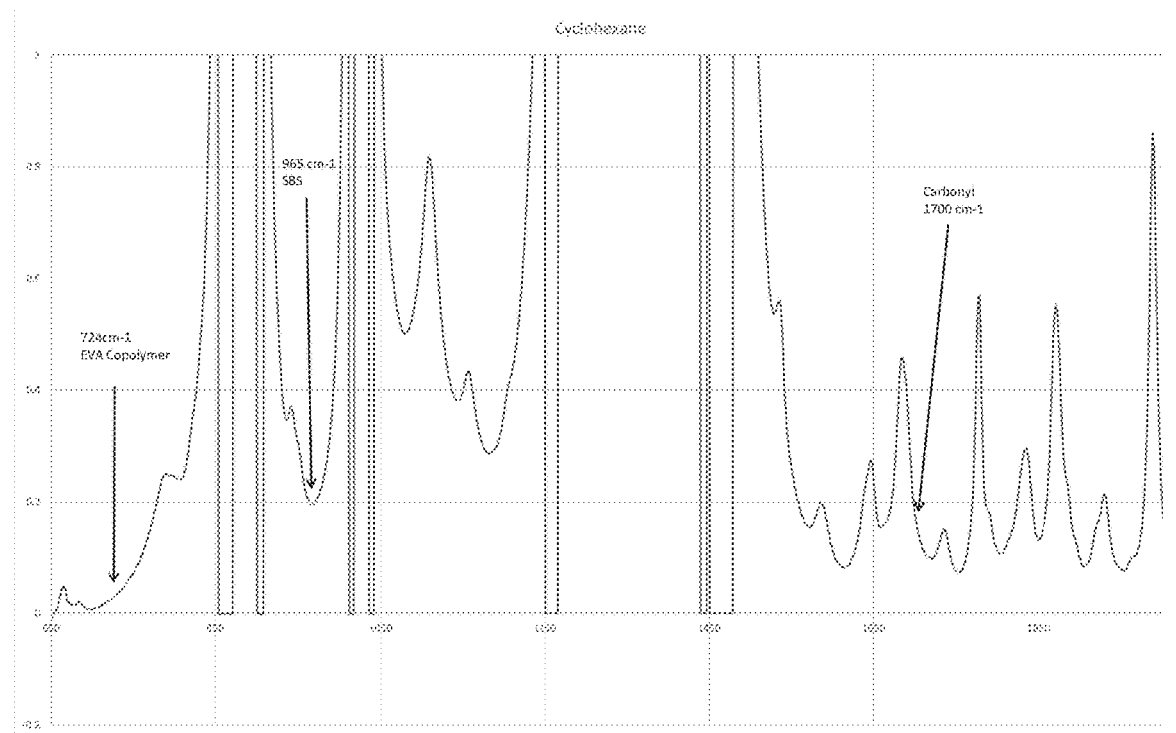
FIG. 24 shows a graph representing Utility of Cyclohexane for FTIR Absorbance Bands.

Some elution solvents (both mobile phases and redissolution solvents) used in future SAR-AD applications and investigations will undoubtedly prove more useful than others for particular applications. As shown in FIG. 23, the relatively strong solvent dichloromethane is very useful for determining sulfoxide and carbonyl band intensities because it does not interfere with those absorption peaks. As shown in FIG. 24, cyclohexane is particularly useful because it not only is it the first solvent used to redissolve a precipitated species such as a polymer, but spectrally it is well-suited for detection of both SBS and EVA. It is also well-suited for analysis of compounds, additives, or modifiers containing a carbonyl functional group. PET (polyethylene terephthalate) is a chemical used to make disposable drinking water and beverage bottles, and is presently being considered worldwide as a recycled material in asphalt paving. Due to its carbonyl functional groups, PET is ideally suited for measurement by SAR-AD fractionation followed by FTIR detection.

APPLICATIONS OF THE INVENTION

Embodiments of the present invention generally relate to the improvement of the specialized WRI fully-automated saturates, aromatics resins—Asphaltene Determinator™ (SAR-AD) analysis through coupling the precipitation and solvent solubility-based redis solution, and solvent based chromatographic adsorption and desorption separation with varieties of non-destructive and destructive method detectors, and the application of this improvement to analyze extremely complex hydrocarbon mixtures and blends.

The SAR-AD separation can now be coupled with non-destructive detectors such as:
  Various spectroscopic techniques like Infrared, including FTIR and NIR, UV-visible detectors including MWD, VWD, DAD, FD.
  RID The SAR-AD separation can be coupled with destructive detectors such as:
  Light scattering techniques such as ELSD and Viscosity LS The results of the detection can be then analyzed using any chemometrics software and particularly these based on neural networks, partial least squares, principal component analysis or the ExpliFit multi linear regression software from WRI which is especially useful for applications where insufficient observations are available compared to the number of independent measurement variables available. Chemometric software can be used for the determination of mathematical relationships of the analytical results of the chemical measurements coming from the SAR-AD second generation, and further for the determination of mathematical relationships between these analytical results and other chemical or physical measurements obtained independently.

Applications: the SAR-AD Second Generation can be used to analyze all kinds of hydrocarbons mixtures and more particularly asphalt binder blends which are commonly used by the industry or currently under development. It is particularly appropriate for characterizing the chemical properties of oil (petroleum or non-petroleum derived), asphalts, polymers, and additives including biomass origin materials, and blends.

Asphalt blends can include but are not limited to any type of asphalt binder used for roofing, paving, sealing of any type of applications. The blends include but are not limited to:

Blends from refining bases (residues from straight run distillation, solvent deasphalting, airblowing, visbreaking, hydrotreating, and cracking or coking units).

Any of above blends further modified with any semi-compatible additives, including but not restricted to polymers and/or additives possibly used in combinations. Polymers can include, but with no restriction all kinds of polymers compatible in asphalt to some degree, including polybutadiene and hydroxy and car-boxy-polybutadiene, rubbers, styrene copolymers such as SBS, SB, SBR, SEBS, SIS, polyolefins such as PE, PP, polyisobutylene, EPDM, oxidized polyolefins, polyethylene copolymers such EVA, EBA, EMA, EGMA and terpolymers of the later ones. Additives comprise acids including phosphonic, phosphoric and polyphosphoric acids, carboxylic and sulfonic acids, including polycarboxylic acids, bases, amphoterics, esters, anhydrides, waxes, amines, amides, sulfur, sulfur derivatives, peroxides, phenols, antioxidants, peroxides, surfactants and salt derivatives, functionalized additives from biomass origins, functionalized additives with fatty, naphthenic or aromatic chains or substituents, organometallic salts. Any polymer can be combined with any additive.

Blends of any of the above with aged asphalts from recycled paving materials or recycled roofing materials with or without rejuvenators with chemical properties included in the description of above additives.

Blends of any of the above with oils from petroleum, coal or biomass origin, including lubricant oils, waste engine oils, refined engine oil bottoms, vegetable oils and waste vegetable oils.

Blends of any of the above at various degrees of aging, processing, reaction, or catalysis.

Blends of any of the above with recycled plastics such as PET, PP, PE, HDPE, PVC.

The knowledge obtained from this invention can be the full or partial, qualitative or semi quantitative composition of the blends. This can be particularly desirable for unknown blends.

This type of knowledge is particularly desirable in forensic applications such as the identification of the nature of pollutants in case of environmental events like oil spillage (catastrophic or not), or the nature of defective products in case of early asphalt pavement failures, as but a few examples.

Certain embodiments of the inventive technology may be described by the following clauses:

I. A method comprising the steps of:
  i. establishing a hydrocarbon into and as part of a first solvent mobile phase, said hydrocarbon including asphaltenes, saturates, a resins fraction that includes highly polar aromatic components and additional resins components, and an aromatics fraction that includes aromatics that are not highly polar;
  ii. passing said first solvent mobile phase over an inert stationary phase;
  iii. precipitating substantially all of said asphaltenes within said inert stationary phase to generate precipitated asphaltenes and a first eluate, said first eluate free of said precipitated asphaltenes;
  iv. subsequently, after performing said step of passing said first solvent mobile phase over said inert stationary phase, passing said first eluate over a non-porous, high surface energy, adsorptive stationary phase to reversibly adsorb substantially all of said highly polar aromatic components of said resins fraction of said first eluate onto said non-porous, high surface energy, adsorptive stationary phase, thereby generating a second eluate and preventing irreversible adsorption of said substantially all of said highly polar aromatic components onto a porous, active stationary phase established downflow of said non-porous, high surface energy, adsorptive stationary phase;
  wherein said second eluate is free of said substantially all of said highly polar aromatic components,
  v. subsequently passing said second eluate over said porous, active stationary phase;
  vi. reversibly adsorbing substantially all of said aromatics fraction onto said porous, active stationary phase to generate a third eluate, said third eluate free of said substantially all of said aromatics fraction;
  vii. eluting substantially all of said saturates as part of said third eluate;
  viii. passing at least one asphaltene solvent over said inert stationary phase to generate at least one asphaltenic eluate; and
  ix. eluting at least a portion of said precipitated asphaltenes as part of said at least one asphaltenic eluate; and said method further comprises the steps of:
  x. measuring at least one response for at least one of said eluates using at least one detector.

2. A method as described in clause 1 wherein said at least one detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

3. A method as described in clause 1 wherein said steps are performed in order in which they appear.

4. A method as described in clause 1 wherein a performance order of said steps is different from that order in which they appear.

5. A method as described in clause 1 wherein said second eluate is the next eluate to occur after said first eluate.

6. A method as described in clause 1 wherein said third eluate is the next eluate to occur after said second eluate.

7. A method as described in clause 1 wherein said at least one asphaltenic eluate is the next eluate to occur after said third eluate.

8. A method as described in clause 1 and further comprising the step of determining the amount of at least one analyte of said at least one eluate based on said at least one response.

9. A method as described in clause 1 wherein said step of measuring at least one response for at least one of said eluates comprises the step of measuring at least one response for said first eluate.

10. A method as described in clause 9 wherein said step of measuring at least one response for said first eluate comprises the step of measuring said at least one response with a shared detector.

11. A method as described in clause 9 wherein said step of measuring at least one response for at least one of said eluates comprises the step of measuring at least one response for said second eluate.

12. A method as described in clause 11 wherein said step of measuring at least one response for said second eluate comprises the step of measuring said at least one response with a shared detector.

13. A method as described in clause 9 wherein said step of measuring at least one response for at least one of said eluates comprises the step of measuring at least one response for said third eluate 14. A method as described in clause 13 wherein said step of measuring at least one response for said third eluate comprises the step of measuring said at least one response with a shared detector.

15. A method as described in clause 9 wherein said step of measuring at least one response for at least one of said eluates comprises the step of measuring at least one response for said at least one asphaltenic eluate.

16. A method as described in clause 15 wherein said step of measuring at least one response for said at least one asphaltenic eluate comprises the step of measuring said at least one response with a shared detector.

17. A method as described in clause 9 wherein said step of measuring at least one response for at least one of said eluates using at least one detector comprises the step of measuring at least two responses for at least one of said eluates using at least two detectors.

18. A method as described in clause 17 wherein said at least two detectors are of different type or are of the same type.

19. A method as described in clause 9 wherein said step of measuring at least one response for at least one of said eluates using at least one detector comprises the step of measuring at least two responses for at least two of said eluates using at least two detectors.

20. A method as described in clause 19 wherein said at least two detectors are of different type or are of the same type.

21. A method as described in clause 1 wherein said step of subsequently passing said first eluate over a non-porous, high surface energy, adsorptive stationary phase comprises the step of passing said first solvent mobile phase over glass beads.

22. A method as described in clause 1 wherein said step of subsequently passing said first eluate over said porous, active stationary phase comprises the step of passing said first solvent mobile phase over a weakly adsorbing stationary phase.

23. A method as described in clause 22 wherein said weakly adsorbing stationary phase comprises activity reduced silica.

24. A method as described in clause 1 wherein said first solvent mobile phase is a low polarity solvent mobile phase.

25. A method as described in clause 1 wherein said step of establishing a hydrocarbon into and as part of a first solvent mobile phase comprises the step of establishing a bitumen in solvent solution into said first solvent mobile phase.

26. A method as described in clause 25 wherein said step of establishing a bitumen in solvent solution into and as part of said first solvent mobile phase comprises the step of establishing a bitumen in a solvent that is strong enough to keep asphaltenes in solution and dissolve said bitumen.

27. A method as described in clause 1 wherein said step of passing said first solvent mobile phase over an inert stationary phase comprises the step of passing said first solvent mobile phase over polytetrafluoroethylene.

28. A method as described in clause 1 wherein said steps are performed in the order in which they appear.

29. A method as described in clause 1 further comprising the step of analyzing said saturates using at least one detector.

30. A method as described in clause 1 further comprising the step of flowing an aromatic desorbing mobile phase over said porous, active stationary phase, said aromatic desorbing mobile phase able to desorb said aromatics fraction from said porous, active stationary phase.

31. A method as described in clause 30 further comprising the step of desorbing said aromatics fraction.

32. A method as described in clause 1 further comprising the step of flowing an aromatics desorbing mobile phase over said porous, active stationary phase but not over said non-porous, high surface energy, adsorptive stationary phase.

33. A method as described in clause 32 further comprising the step of eluting substantially all of said aromatics fraction.

34. A method as described in clause 33 further comprising the step of analyzing said aromatics fraction using at least one detector.

35. A method as described in clause 1 further comprising the step of flowing a resins material desorbing mobile phase over said non-porous, high surface energy, adsorptive stationary phase, said resins material desorbing mobile phase able to desorb resins adsorbed onto said non-porous, high surface energy, adsorptive stationary phase.

36. A method as described in claim 35 further comprising the step of desorbing said resins adsorbed onto said non-porous, high surface energy, adsorptive stationary phase.

37. A method as described in clause 36 further comprising the step of analyzing said resins desorbed from said non-porous, high surface energy, adsorptive stationary phase using at least one detector.

38. A method as described in clause 35 further comprising the step of flowing said resins desorbing mobile phase over an activity reduced stationary phase but not over a highly active stationary phase.

39. A method as described in clause 38 further comprising the step of desorbing resins adsorbed onto said activity reduced stationary phase.

40. A method as described in clause 39 further comprising the step of analyzing said resins using at least one detector.

41. A method as described in clause 1 wherein said step of passing at least one asphaltene solvent over said inert stationary phase comprises the step of passing a first asphaltene solvent over said inert stationary phase, thereby dissolving at least a first portion of said precipitated asphaltenes.

42. A method as described in clause 41 wherein said step of dissolving at least a first portion of said precipitated asphaltenes comprises the step of dissolving a highly alkyl substituted pericondensed aromatic material fraction.

43. A method as described in clause 42 further comprising the step of analyzing said highly alkyl substituted pericondensed aromatic material fraction using at least one detector.

44. A method as described in clause 41 further comprising the step of dissolving at least a second portion of said precipitated asphaltenes with a second asphaltene solvent, said second asphaltene solvent being stronger than said first asphaltene solvent.

45. A method as described in clause 44 wherein said step of dissolving at least a second portion of said precipitated asphaltenes comprises the step of dissolving a pericondensed aromatic material fraction.

46. A method as described in clause 45 further comprising the step of analyzing said pericondensed aromatic material fraction using at least one detector.

47. A method as described in clause 44 wherein said step of dissolving at least a second portion of said precipitated asphaltenes with a second asphaltene solvent comprises the step of dissolving at least a second portion of said precipitated asphaltenes with toluene.

48. A method as described in clause 44 further comprising the step of dissolving at least a third portion of said precipitated asphaltenes with a third asphaltene solvent, said third solvent stronger than said second asphaltene solvent.

49. A method as described in clause 48 wherein said step of dissolving at least a third portion of said precipitated asphaltenes comprises the step of dissolving a pre-coke aromatic material fraction.

50. A method as described in clause 49 further comprising the step of analyzing said pre-coke aromatic fraction using at least one detector.

51. A method as described in clause 1 further comprising the step of passing said first solvent mobile phase over a weakly adsorbing stationary phase established downflow of said non-porous, high surface energy, adsorptive stationary phase.

52. A method as described in clause 51 wherein said step of passing said first solvent mobile phase over a weakly adsorbing stationary phase comprises the step of passing said solvent mobile phase over a weakly adsorbing stationary phase established upflow of said porous, active stationary phase.

53. A method comprising the steps of:
  performing a solubility-based analysis (SBA) of an SBA portion of a hydrocarbon by:
  i. establishing said SBA portion of said hydrocarbon into and as part of an SBA run of a first solvent mobile phase, said SBA portion of said hydrocarbon including SBA portion asphaltenes, saturates, a resins fraction that includes highly polar aromatic components and additional resins components, and an aromatics fraction that includes aromatics that are not highly polar;
  ii. passing said SBA run of said first solvent mobile phase over an asphaltene-free inert stationary phase;
  iii. precipitating substantially all of said SBA portion asphaltenes within said inert stationary phase to generate SBA portion precipitated asphaltenes and a first SBA eluate, said first SBA eluate free of said precipitated asphaltenes;
  iv. subsequently passing said first SBA eluate over a non-porous, high surface energy, adsorptive stationary phase to reversibly adsorb substantially all of said highly polar aromatic components of said resins fraction from said first solvent mobile phase onto said non-porous, high surface energy, adsorptive stationary phase, thereby generating a second SBA eluate and preventing irreversible adsorption of said substantially all of said highly polar aromatic components onto a porous, active stationary phase established downflow of said non-porous, high surface energy, adsorptive stationary phase;
  v. subsequently passing said second SBA eluate over said porous, active stationary phase;
  vi. reversibly adsorbing substantially all of said aromatics fraction onto said porous, active stationary phase to generate a third SBA eluate, said third SBA eluate free of said substantially all of said aromatics fraction;
  vii. eluting substantially all of said saturates as part of said third SBA eluate;
  viii. passing at least one asphaltene solvent over said inert stationary phase to generate at least one SBA portion asphaltenic eluate; and
  ix. eluting substantially all of said SBA portion precipitated asphaltenes as part of said at least one SBA portion asphaltenic eluate;
  performing a size exclusion analysis (SEA) of a SEA portion of said hydrocarbon by:
  x. establishing a SEA portion of said hydrocarbon into and as part of a SEA run of said first solvent mobile phase, said SEA portion of said hydrocarbon including SEA portion asphaltenes and SEA portion maltenes;
  xi. passing said SEA run of said first solvent mobile phase over said asphaltene-free inert stationary phase;
  xii. precipitating substantially all of said SEA portion asphaltenes within said inert stationary phase to generate SEA portion precipitated asphaltenes and a first SEA eluate;
  xiii. passing said first SEA eluate through a size exclusion chromatography stationary phase to generate a second SEA eluate;
  xiv. measuring at least one response for said second SEA eluate using at least one detector; and
  xv. passing at least one asphaltene solvent over said inert stationary phase to generate at least one SEA portion asphaltenic eluate; and
  xvi. eluting substantially all of said SEA portion precipitated asphaltenes as part of said at least one SEA portion asphaltenic eluate.

54. A method as described in clause 53 wherein said steps of performing a solubility-based analysis (SBA) of an SBA portion of said hydrocarbon (said steps i-ix) are performed before said steps of performing a size exclusion analysis (SEA) of a SEA portion of said hydrocarbon (said steps x-xvi) are performed.

55. A method as described in clause 53 wherein said steps of performing a size exclusion analysis (SEA) of a SEA portion of said hydrocarbon (said steps x-xvi) are performed before said steps performing a solubility-based analysis (SBA) of an SBA portion of said hydrocarbon (said steps i-ix) are performed.

56. A method as described in clause 53 wherein said step of measuring at least one response for said second SEA eluate using at least one detector comprises the step of measuring said at least one response for said second SEA eluate using at least one refractive index detector.

57. A method as described in clause 53 wherein said step of measuring at least one response for said second SEA eluate using at least one detector comprises the step of measuring said at least one response for said second SEA eluate using at least one detector comprises the step of measuring at least one response using at least one detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

58. A method as described in clause 53 wherein said step of passing at least one asphaltene solvent over said inert stationary phase to generate at least one SBA portion asphaltenic eluate comprises the step of passing at least two solvents of increasing polarity to generate at least two SBA portion asphaltenic eluates.

59. A method as described in clause 58 wherein said step of passing at least two solvents is part of a successive dissolution procedure.

60. A method as described in clause 1 wherein said step of measuring at least one response for at least one of said eluates comprises the step of measuring at least one response for said first eluate.

61. A method as described in clause 53 wherein said step of passing at least one asphaltene solvent over said inert stationary phase to generate at least one SBA portion asphaltenic eluate comprises the step of passing at least three solvents of increasing polarity to generate at least three SBA portion asphaltenic eluates.

62. A method as described in clause 61 wherein said step of passing at least three solvents is part of a successive dissolution procedure.

63. A method as described in clause 53 wherein said size exclusion chromatography stationary phase comprises a permeable gel.

64. A method as described in clause 53 wherein said steps of i. through ix. are performed before the performance of said step x. is initiated.

65. A method as described in clause 53 and further comprising the step of determining the amount of at least one analyte of hydrocarbon maltenes of based on said at least one response for said second SEA eluate.

66. A method as described in clause 53 further comprising the step of measuring at least one additional response for any one or more of said SBA eluates and said at least one SBA portion asphaltenic eluate using at least one detector.

67. A method as described in clause 66 wherein said at least one detector comprises a detector selected from the group consisting of ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

68. A method as described in clause 53 wherein said step of subsequently passing said first SBA eluate over a non-porous, high surface energy, adsorptive stationary phase comprises the step of passing said first SBA eluate over glass beads.

69. A method as described in clause 53 wherein said step of subsequently passing said first SBA eluate over said porous, active stationary phase comprises the step of passing said first SBA eluate over a weakly adsorbing stationary phase.

70. A method as described in clause 69 wherein said weakly adsorbing stationary phase comprises activity reduced silica.

71. A method as described in clause 53 wherein said first solvent mobile phase is a low polarity solvent mobile phase.

72. A method as described in clause 53 wherein said step of establishing a hydrocarbon into and as part of a first solvent mobile phase comprises the step of establishing a bitumen in solvent solution into said first solvent mobile phase.

73. A method as described in clause 72 wherein said step of establishing a bitumen in solvent solution into and as part of said first solvent mobile phase comprises the step of establishing a bitumen in a solvent that is strong enough to keep asphaltenes in solution and dissolve said bitumen.

74. A method as described in clause 53 wherein said step of passing said SBA run of said first solvent mobile phase and said SEA run of said first solvent mobile phase over an inert stationary phase comprises the step of passing said first solvent mobile phase over polytetrafluoroethylene.

75. A method as described in clause 53 wherein said steps are performed in the order in which they appear.

76. A method as described in clause 53 further comprising the step of analyzing said saturates using at least one detector.

77. A method as described in clause 53 further comprising the step of flowing an aromatic desorbing mobile phase over said porous, active stationary phase, said aromatic desorbing mobile phase able to desorb said aromatics fraction from said porous, active stationary phase.

78. A method as described in clause 77 further comprising the step of desorbing said aromatics fraction.

79. A method as described in clause 53 further comprising the step of flowing an aromatics desorbing mobile phase over said porous, active stationary phase but not over said non-porous, high surface energy, adsorptive stationary phase.

80. A method as described in clause 53 further comprising the step of eluting substantially all of said aromatics fraction.

81. A method as described in clause 59 further comprising the step of analyzing said aromatics fraction using at least one detector.

82. A method as described in clause 53 further comprising the step of flowing a resins material desorbing mobile phase over said non-porous, high surface energy, adsorptive stationary phase, said resins material desorbing mobile phase able to desorb resins adsorbed onto said non-porous, high surface energy, adsorptive stationary phase.

83. A method as described in clause 82 further comprising the step of desorbing said resins adsorbed onto said non-porous, high surface energy, adsorptive stationary phase.

84. A method as described in clause 83 further comprising the step of analyzing said resins desorbed from said non-porous, high surface energy, adsorptive stationary phase using at least one detector.

85. A method as described in clause 82 further comprising the step of flowing said resins desorbing mobile phase over an activity reduced stationary phase but not over a highly active stationary phase.

86. A method as described in clause 85 further comprising the step of desorbing resins adsorbed onto said activity reduced stationary phase.

87. A method as described in clause 86 further comprising the step of analyzing said resins using at least one detector.

88. A method as described in clause 53 wherein said step of passing at least one asphaltene solvent over said inert stationary phase comprises the step of passing a first asphaltene solvent over said inert stationary phase, thereby dissolving at least a first portion of said precipitated asphaltenes.

89. A method as described in clause 88 wherein said step of dissolving at least a first portion of said precipitated asphaltenes comprises the step of dissolving a highly alkyl substituted pericondensed aromatic material fraction.

90. A method as described in clause 89 further comprising the step of analyzing said highly alkyl substituted pericondensed aromatic material fraction using at least one detector.

91. A method as described in clause 88 further comprising the step of dissolving at least a second portion of said precipitated asphaltenes with a second asphaltene solvent, said second asphaltene solvent being stronger than said first asphaltene solvent.

92. A method as described in clause 91 wherein said step of dissolving at least a second portion of said precipitated asphaltenes comprises the step of dissolving a pericondensed aromatic material fraction.

93. A method as described in clause 92 further comprising the step of analyzing said pericondensed aromatic material fraction using at least one detector.

94. A method as described in clause 79 wherein said step of dissolving at least a second portion of said precipitated asphaltenes with a second asphaltene solvent comprises the step of dissolving at least a second portion of said precipitated asphaltenes with toluene.

95. A method as described in clause 91 further comprising the step of dissolving at least a third portion of said precipitated asphaltenes with a third asphaltene solvent, said third solvent stronger than said second asphaltene solvent.

96. A method as described in clause 95 wherein said step of dissolving at least a third portion of said precipitated asphaltenes comprises the step of dissolving a pre-coke aromatic material fraction.

97. A method as described in clause 96 further comprising the step of analyzing said pre-coke aromatic fraction using at least one detector.

97. A method as described in clause 53 further comprising the step of passing said first solvent mobile phase over a weakly adsorbing stationary phase established downflow of said non-porous, high surface energy, adsorptive stationary phase.

99. A method as described in clause 98 wherein said step of passing said first solvent mobile phase over a weakly adsorbing stationary phase comprises the step of passing said solvent mobile phase over a weakly adsorbing stationary phase established upflow of said porous, active stationary phase.

100. A method comprising the steps of:
  i. establishing a hydrocarbon into and as part of a first solvent mobile phase, said hydrocarbon including asphaltenes, saturates, a resins fraction that includes highly polar aromatic components and additional resins components, and an aromatics fraction that includes aromatics that are not highly polar;
  ii. passing said first solvent mobile phase over an inert stationary phase;
  iii. precipitating substantially all of said asphaltenes within said inert stationary phase to generate precipitated asphaltenes and a first eluate, said first eluate free of said precipitated asphaltenes;
  iv. splitting said first eluate into a first flow and a second flow;
  v. subsequently, after performing said step of splitting said first eluate into a first flow and a second flow, passing said first flow over a non-porous, high surface energy, adsorptive stationary phase to reversibly adsorb substantially all of said highly polar aromatic components of said resins fraction of said first flow onto said non-porous, high surface energy, adsorptive stationary phase, thereby generating a first flow, second eluate that is free of said substantially all of said highly polar aromatic components of said first flow, and preventing irreversible adsorption of said substantially all of said highly polar aromatic components of said first flow onto a porous, active stationary phase established downflow of said non-porous, high surface energy, adsorptive stationary phase;
  vi. subsequently passing said first flow, second eluate over said porous, active stationary phase;
  vii. reversibly adsorbing substantially all of said aromatics fraction of said first flow onto said porous, active stationary phase to generate a first flow, third eluate, said first flow, third eluate free of said substantially all of said aromatics fraction of said first flow;
  viii. eluting substantially all of said saturates of said first flow as part of said first flow, third eluate;
  ix. after performing said step of splitting said first eluate into a first flow and a second flow, passing said second flow through a size exclusion chromatography stationary phase to generate a second flow, second eluate
  x. measuring at least one response for said second flow, second eluate using at least one detector.

101. A method as described in clause 100 wherein said steps v and ix start substantially at the same time.

102. A method as described in clause 100 wherein said steps v and ix start substantially immediately after said step iv is performed.

103. A method as described in clause 100 wherein said step of measuring said at least one response for said second flow, second eluate using at least one detector comprises the step of measuring said at least one response using a refractive index detector.

104. A method as described in clause 100 wherein said step of splitting said first eluate into a first flow and a second flow comprises the step of splitting said first eluate into a first flow and a second flow that are of different mass flow rates or equal mass flow rates.

105. A method as described in clause 100 further comprising the step of measuring at least one response for said first flow, second eluate using at least one detector.

106. A method as described in clause 105 wherein said at least one detector comprises a detector selected from the group consisting of ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

107. A method as described in clause 100 further comprising the step of measuring at least one response for said first flow, third eluate using at least one detector.

108. A method as described in clause 107 wherein said at least one detector comprises a detector selected from the group consisting of ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

109. A method as described in clause 100 wherein said step of measuring at least one response for at least one of said eluates comprises the step of measuring at least one response for said first eluate.

110. A method as described in clause 100 wherein said size exclusion chromatography stationary phase comprises a permeable gel.

111. A method as described in clause 100 and further comprising the step of determining the amount of at least one analyte of said second flow, second eluate based on said at least one response.

112. A method as described in clause 100 and further comprising the step of passing at least one asphaltene solvent over said inert stationary phase to generate an asphaltenic eluate that includes at least a portion of said precipitated asphaltenes.

113. A method as described in clause 112 further comprising the step of measuring at least one response for said asphaltenic eluate using at least one detector capable of determining at least one asphaltenic analyte.

114. A method as described in clause 100 wherein said step of subsequently passing said first flow over a non-porous, high surface energy, adsorptive stationary phase comprises the step of passing said first solvent mobile phase over glass beads.

115. A method as described in clause 100 wherein said step of subsequently passing said first flow over said porous, active stationary phase comprises the step of passing said first solvent mobile phase over a weakly adsorbing stationary phase.

116. A method as described in clause 115 wherein said weakly adsorbing stationary phase comprises activity reduced silica.

117. A method as described in clause 100 wherein said first solvent mobile phase is a low polarity solvent mobile phase.
118. A method as described in clause 100 wherein said step of establishing a hydrocarbon into and as part of a first solvent mobile phase comprises the step of establishing a bitumen in solvent solution into said first solvent mobile phase.
119. A method as described in clause 118 wherein said step of establishing a bitumen in solvent solution into and as part of said first solvent mobile phase comprises the step of establishing a bitumen in a solvent that is strong enough to keep asphaltenes in solution and dissolve said bitumen.
120. A method as described in clause 100 wherein said step of passing said first solvent mobile phase over an inert stationary phase comprises the step of passing said first solvent mobile phase over polytetrafluoroethylene.
121. A method as described in clause 100 further comprising the step of analyzing said saturates using at least one detector.
122. A method as described in clause 100 further comprising the step of flowing an aromatic desorbing mobile phase over said porous, active stationary phase, said aromatic desorbing mobile phase able to desorb said aromatics fraction from said porous, active stationary phase.
123. A method as described in clause 122 further comprising the step of desorbing said aromatics fraction.
124. A method as described in clause 100 further comprising the step of flowing an aromatics desorbing mobile phase over said porous, active stationary phase but not over said non-porous, high surface energy, adsorptive stationary phase.
125. A method as described in clause 122 further comprising the step of eluting substantially all of said aromatics fraction.
126. A method as described in clause 123 further comprising the step of analyzing said aromatics fraction using at least one detector.
127. A method as described in clause 100 further comprising the step of flowing a resins material desorbing mobile phase over said non-porous, high surface energy, adsorptive stationary phase, said resins material desorbing mobile phase able to desorb resins adsorbed onto said non-porous, high surface energy, adsorptive stationary phase.
128. A method as described in clause 125 further comprising the step of desorbing said resins adsorbed onto said non-porous, high surface energy, adsorptive stationary phase.
129. A method as described in clause 126 further comprising the step of analyzing said resins desorbed from said non-porous, high surface energy, adsorptive stationary phase using at least one detector.
130. A method as described in clause 125 further comprising the step of flowing said resins desorbing mobile phase over an activity reduced stationary phase but not over a highly active stationary phase.
131. A method as described in clause 128 further comprising the step of desorbing resins adsorbed onto said activity reduced stationary phase.
132. A method as described in clause 129 further comprising the step of analyzing said resins using at least one detector.
133. A method as described in clause 100 wherein said step of passing at least one asphaltene solvent over said inert stationary phase comprises the step of passing a first asphaltene solvent over said inert stationary phase, thereby dissolving at least a first portion of said precipitated asphaltenes.
134. A method as described in clause 133 wherein said step of dissolving at least a first portion of said precipitated asphaltenes comprises the step of dissolving a highly alkyl substituted pericondensed aromatic material fraction.
135. A method as described in clause 134 further comprising the step of analyzing said highly alkyl substituted pericondensed aromatic material fraction using at least one detector.
136. A method as described in clause 133 further comprising the step of dissolving at least a second portion of said precipitated asphaltenes with a second asphaltene solvent, said second asphaltene solvent being stronger than said first asphaltene solvent.
137. A method as described in clause 136 wherein said step of dissolving at least a second portion of said precipitated asphaltenes comprises the step of dissolving a pericondensed aromatic material fraction.
138. A method as described in clause 137 further comprising the step of analyzing said pericondensed aromatic material fraction using at least one detector.
139. A method as described in clause 136 wherein said step of dissolving at least a second portion of said precipitated asphaltenes with a second asphaltene solvent comprises the step of dissolving at least a second portion of said precipitated asphaltenes with toluene.
140. A method as described in clause 136 further comprising the step of dissolving at least a third portion of said precipitated asphaltenes with a third asphaltene solvent, said third solvent stronger than said second asphaltene solvent.
141. A method as described in clause 140 wherein said step of dissolving at least a third portion of said precipitated asphaltenes comprises the step of dissolving a pre-coke aromatic material fraction.
142. A method as described in clause 141 further comprising the step of analyzing said pre-coke aromatic fraction using at least one detector.
143. A method as described in clause 100 further comprising the step of passing said first solvent mobile phase over a weakly adsorbing stationary phase established downflow of said non-porous, high surface energy, adsorptive stationary phase.
144. A method as described in clause 143 wherein said step of passing said first solvent mobile phase over a weakly adsorbing stationary phase comprises the step of passing said solvent mobile phase over a weakly adsorbing stationary phase established upflow of said porous, active stationary phase.

This knowledge obtained from this invention can be then used to formulate, blend and mix more cost efficiently long term performing asphalt materials, lubricants, greases, crude oils or any petroleum products, or more generally chemical products, including additives and polymers, making them easier and more cost effective to produce to analyze/detect/quantify and survey in their long-term service life. This invention is more particularly suited to analyze asphalt blends with polymer and/or additives.

As can be easily understood from the foregoing, the basic concepts of the present invention may be embodied in a variety of ways. It involves both analyzing techniques as well as devices to accomplish the appropriate analysis. In this application, the analyzing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any acts of law, statutes, regulations, or rules mentioned in this application for patent; patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the analysis devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method comprising the steps of:
   i. establishing a hydrocarbon into and as part of a first solvent mobile phase, said hydrocarbon including asphaltenes, saturates, a resins fraction that includes highly polar aromatic components and additional resins components, and an aromatics fraction that includes aromatics that are not highly polar;
   ii. passing said first solvent mobile phase over an inert stationary phase;
   iii. precipitating substantially all of said asphaltenes within said inert stationary phase to generate precipitated asphaltenes and a first eluate, said first eluate free of said precipitated asphaltenes;
   iv. subsequently, after performing said step of passing said first solvent mobile phase over said inert stationary phase, passing said first eluate over a non-porous, high surface energy, adsorptive stationary phase to reversibly adsorb substantially all of said highly polar aromatic components of said resins fraction of said first eluate onto said non-porous, high surface energy, adsorptive stationary phase, thereby generating a second eluate and preventing irreversible adsorption of said substantially all of said highly polar aromatic components onto a porous, active stationary phase established downflow of said non-porous, high surface energy, adsorptive stationary phase;
   wherein said second eluate is free of said substantially all of said highly polar aromatic components,
   v. subsequently passing said second eluate over said porous, active stationary phase;
   vi. reversibly adsorbing substantially all of said aromatics fraction onto said porous, active stationary phase to generate a third eluate, said third eluate free of said substantially all of said aromatics fraction;
   vii. eluting substantially all of said saturates as part of said third eluate;
   viii. passing at least one asphaltene solvent over said inert stationary phase to generate at least one asphaltenic eluate; and
   ix. eluting at least a portion of said precipitated asphaltenes as part of said at least one asphaltenic eluate; and
   said method further comprises the steps of:
   x. measuring at least one response for at least one of said eluates using at least one detector.

2. A method as described in claim 1 wherein said at least one detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FTIR, and fluorescence detector.

3. A method as described in claim 1 wherein said steps are performed in order in which they appear.

4. A method as described in claim 1 wherein a performance order of said steps is different from that order in which they appear.

5. A method as described in claim 1 wherein said second eluate is the next eluate to occur after said first eluate.

6. A method as described in claim 1 wherein said third eluate is the next eluate to occur after said second eluate.

7. A method as described in claim 1 wherein said at least one asphaltenic eluate is the next eluate to occur after said third eluate.

8. A method as described in claim 1 and further comprising the step of determining the amount of at least one analyte of said at least one eluate based on said at least one response.

9. A method as described in claim 1 wherein said step of measuring at least one response for at least one of said eluates comprises the step of measuring at least one response for said first eluate.

10. A method as described in claim 9 wherein said step of measuring at least one response for said first eluate comprises the step of measuring said at least one response with a shared detector.

11. A method as described in claim 9 wherein said step of measuring at least one response for at least one of said eluates further comprises the step of measuring at least one response for said second eluate.

12. A method as described in claim 11 wherein said step of measuring at least one response for said second eluate comprises the step of measuring said at least one response with a shared detector.

13. A method as described in claim 9 wherein said step of measuring at least one response for at least one of said eluates further comprises the step of measuring at least one response for said third eluate.

14. A method as described in claim 13 wherein said step of measuring at least one response for said third eluate comprises the step of measuring said at least one response with a shared detector.

15. A method as described in claim 9 wherein said step of measuring at least one response for at least one of said eluates further comprises the step of measuring at least one response for said at least one asphaltenic eluate.

16. A method as described in claim 15 wherein said step of measuring at least one response for said at least one asphaltenic eluate comprises the step of measuring said at least one response with a shared detector.

17. A method as described in claim 9 wherein said step of measuring at least one response for at least one of said eluates using at least one detector further comprises the step of measuring at least two responses for at least one of said eluates using at least two detectors.

18. A method as described in claim 17 wherein said at least two detectors are of different type or are of the same type.

19. A method as described in claim 9 wherein said step of measuring at least one response for at least one of said eluates using at least one detector comprises the step of measuring at least two responses for at least two of said eluates using at least two detectors.

20. A method as described in claim 19 wherein said at least two detectors are of different type or are of the same type.

21. A method as described in claim 1 wherein said step of subsequently passing said first eluate over a non-porous, high surface energy, adsorptive stationary phase comprises the step of passing said first solvent mobile phase over glass beads.

22. A method as described in claim 1 wherein said step of subsequently passing said first eluate over said porous, active stationary phase comprises the step of passing said first solvent mobile phase over a weakly adsorbing stationary phase.

23. A method as described in claim 22 wherein said weakly adsorbing stationary phase comprises activity reduced silica.

24. A method as described in claim 1 wherein said first solvent mobile phase is a low polarity solvent mobile phase.

25. A method as described in claim 1 wherein said step of establishing a hydrocarbon into and as part of a first solvent mobile phase comprises the step of establishing a bitumen in solvent solution into said first solvent mobile phase.

26. A method as described in claim 25 wherein said step of establishing a bitumen in solvent solution into and as part of said first solvent mobile phase comprises the step of establishing a bitumen in a solvent that is strong enough to keep asphaltenes in solution and dissolve said bitumen.

27. A method as described in claim 1 wherein said step of passing said first solvent mobile phase over an inert stationary phase comprises the step of passing said first solvent mobile phase over polytetrafluoroethylene.

28. A method as described in claim 1 wherein said steps i-ix, are performed in the order in which they appear.

29. A method as described in claim 1 further comprising the step of analyzing said saturates from said at least one response.

30. A method as described in claim 1 further comprising the step of flowing an aromatic desorbing mobile phase over said porous, active stationary phase, said aromatic desorbing mobile phase able to desorb said aromatics fraction from said porous, active stationary phase.

31. A method as described in claim 30 further comprising the step of desorbing said aromatics fraction.

32. A method as described in claim 1 further comprising the step of flowing an aromatics desorbing mobile phase over said porous, active stationary phase but not over said non-porous, high surface energy, adsorptive stationary phase.

33. A method as described in claim 32 further comprising the step of eluting substantially all of said aromatics fraction.

34. A method as described in claim 33 further comprising the step of analyzing said aromatics fraction using at least one detector from said at least one response.

35. A method as described in claim 1 further comprising the step of flowing a resins material desorbing mobile phase over said non-porous, high surface energy, adsorptive stationary phase, said resins material desorbing mobile phase able to desorb resins adsorbed onto said non-porous, high surface energy, adsorptive stationary phase.

36. A method as described in claim 35 further comprising the step of desorbing said resins adsorbed onto said non-porous, high surface energy, adsorptive stationary phase.

37. A method as described in claim 36 further comprising the step of analyzing said resins desorbed from said non-porous, high surface energy, adsorptive stationary phase from said at least one response.

38. A method as described in claim 35 further comprising the step of flowing said resins desorbing mobile phase over an activity reduced stationary phase but not over a highly active stationary phase.

39. A method as described in claim 38 further comprising the step of desorbing resins adsorbed onto said activity reduced stationary phase.

40. A method as described in claim 39 further comprising the step of analyzing said resins from said at least one response.

41. A method as described in claim 1 wherein said step of passing at least one asphaltene solvent over said inert stationary phase comprises the step of passing a first asphaltene solvent over said inert stationary phase, thereby dissolving at least a first portion of said precipitated asphaltenes.

42. A method as described in claim 41 wherein said step of dissolving at least a first portion of said precipitated asphaltenes comprises the step of dissolving a highly alkyl substituted pericondensed aromatic material fraction.

43. A method as described in claim 42 further comprising the step of analyzing said highly alkyl substituted pericondensed aromatic material fraction from said at least one response.

44. A method as described in claim 41 further comprising the step of dissolving at least a second portion of said precipitated asphaltenes with a second asphaltene solvent, said second asphaltene solvent being stronger than said first asphaltene solvent.

45. A method as described in claim 44 wherein said step of dissolving at least a second portion of said precipitated asphaltenes comprises the step of dissolving a pericondensed aromatic material fraction.

46. A method as described in claim 45 further comprising the step of analyzing said pericondensed aromatic material fraction using at least one detector from said at least one response.

47. A method as described in claim 44 wherein said step of dissolving at least a second portion of said precipitated asphaltenes with a second asphaltene solvent comprises the step of dissolving at least a second portion of said precipitated asphaltenes with toluene.

48. A method as described in claim 44 further comprising the step of dissolving at least a third portion of said precipitated asphaltenes with a third asphaltene solvent, said third solvent stronger than said second asphaltene solvent.

49. A method as described in claim 48 wherein said step of dissolving at least a third portion of said precipitated asphaltenes comprises the step of dissolving a pre-coke aromatic material fraction.

50. A method as described in claim 49 further comprising the step of analyzing said pre-coke aromatic fraction from said at least one response.

51. A method as described in claim 1 further comprising the step of passing said first solvent mobile phase over a weakly adsorbing stationary phase established downflow of said non-porous, high surface energy, adsorptive stationary phase.

52. A method as described in claim 51 wherein said step of passing said first solvent mobile phase over a weakly adsorbing stationary phase comprises the step of passing said solvent mobile phase over a weakly adsorbing stationary phase established upflow of said porous, active stationary phase.

53. A method as described in claim 1 wherein said step of measuring at least one response for at least one of said eluates comprises the step of measuring at least two responses for at least one of said eluates using at least one shared detector.

54. A method as described in claim 53 wherein said step of measuring at least two responses for at least one of said eluates comprises the step of measuring at least two responses for at least two of said eluates using at least one shared detector.

55. A method comprising the steps of:
performing a solubility-based analysis (SBA) of an SBA portion of a hydrocarbon by:
i. establishing said SBA portion of said hydrocarbon into and as part of an SBA run of a first solvent mobile phase, said SBA portion of said hydrocarbon including SBA portion asphaltenes, saturates, a resins fraction that includes highly polar aromatic components and additional resins components, and an aromatics fraction that includes aromatics that are not highly polar;
ii. passing said SBA run of said first solvent mobile phase over an asphaltene-free inert stationary phase;
iii. precipitating substantially all of said SBA portion asphaltenes within said inert stationary phase to generate SBA portion precipitated asphaltenes and a first SBA eluate, said first SBA eluate free of said precipitated asphaltenes;
iv. subsequently passing said first SBA eluate over a non-porous, high surface energy, adsorptive stationary phase to reversibly adsorb substantially all of said highly polar aromatic components of said resins fraction from said first solvent mobile phase onto said non-porous, high surface energy, adsorptive stationary phase, thereby generating a second SBA eluate and preventing irreversible adsorption of said substantially all of said highly polar aromatic components onto a porous, active stationary phase established downflow of said non-porous, high surface energy, adsorptive stationary phase;
v. subsequently passing said second SBA eluate over said porous, active stationary phase;
vi. reversibly adsorbing substantially all of said aromatics fraction onto said porous, active stationary phase to generate a third SBA eluate, said third SBA eluate free of said substantially all of said aromatics fraction;
vii. eluting substantially all of said saturates as part of said third SBA eluate;
viii. passing at least one asphaltene solvent over said inert stationary phase to generate at least one SBA portion asphaltenic eluate; and
ix. eluting substantially all of said SBA portion precipitated asphaltenes as part of said at least one SBA portion asphaltenic eluate;
performing a size exclusion analysis (SEA) of a SEA portion of said hydrocarbon by:
x. establishing said SEA portion of said hydrocarbon into and as part of a SEA run of said first solvent mobile phase, said SEA portion of said hydrocarbon including SEA portion asphaltenes and SEA portion maltenes;
xi. passing said SEA run of said first solvent mobile phase over said asphaltene-free inert stationary phase;
xii. precipitating substantially all of said SEA portion asphaltenes within said inert stationary phase to generate SEA portion precipitated asphaltenes and a first SEA eluate;
xiii. passing said first SEA eluate through a size exclusion chromatography stationary phase to generate a second SEA eluate;
xiv. measuring at least one response for said second SEA eluate using at least one detector; and xv. passing at least one asphaltene solvent over said inert stationary phase to generate at least one SEA portion asphaltenic eluate; and
xvi. eluting substantially all of said SEA portion precipitated asphaltenes as part of said at least one SEA portion asphaltenic eluate.

* * * * *